(12) United States Patent
Yliperttula et al.

(10) Patent No.: US 10,976,308 B2
(45) Date of Patent: Apr. 13, 2021

(54) PLANT-DERIVED NANOFIBRILLAR CELLULOSE HYDROGEL FOR CELL CULTURE AND CHEMICAL TESTING

(71) Applicant: UPM-KYMMENE CORPORATION, Helsinki (FI)

(72) Inventors: Marjo Yliperttula, Espoo (FI); Arto Urtti, Kuopio (FI); Yan-Ru Lou, Helsinki (FI); Melina Malinen, Helsinki (FI); Patrick Laurén, Espoo (FI); Liisa Kanninen, Helsinki (FI); Kirsti Johanna Niklander, Espoo (FI); Petter Somersalo, Helsinki (FI); Riina Harjumäki, Helsinki (FI)

(73) Assignee: UPM-KYMMENE CORPORATION, Helsinki (FI)

(*) Notice: Subject to any disclaimer, the term of this patent is extended or adjusted under 35 U.S.C. 154(b) by 0 days.

(21) Appl. No.: 15/536,558

(22) PCT Filed: Dec. 18, 2015

(86) PCT No.: PCT/FI2015/050910
§ 371 (c)(1),
(2) Date: Jun. 15, 2017

(87) PCT Pub. No.: WO2016/097490
PCT Pub. Date: Jun. 23, 2016

(65) Prior Publication Data
US 2018/0024121 A1 Jan. 25, 2018

(30) Foreign Application Priority Data
Dec. 18, 2014 (FI) ...................... 20146115

(51) Int. Cl.
*G01N 33/50* (2006.01)
*G01N 33/543* (2006.01)
*C12N 5/00* (2006.01)
*C12N 5/0735* (2010.01)

(52) U.S. Cl.
CPC ....... *G01N 33/5082* (2013.01); *C12N 5/0062* (2013.01); *C12N 5/0068* (2013.01); *C12N 5/0606* (2013.01); *G01N 33/5008* (2013.01); *G01N 33/5014* (2013.01); *G01N 33/5023* (2013.01); *G01N 33/5026* (2013.01); *G01N 33/5436* (2013.01); *C12N 2533/78* (2013.01); *C12N 2539/10* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 7,449,180 B2 | 11/2008 | Kisiday et al. | |
| 2005/0095695 A1 | 5/2005 | Shindler et al. | |
| 2010/0056390 A1 | 3/2010 | Fischbach | |
| 2012/0244567 A1 | 9/2012 | Zeng | |
| 2013/0344036 A1* | 12/2013 | Yliperttula | ............... A61K 9/06 424/93.7 |
| 2015/0056390 A1 | 2/2015 | Miyai et al. | |

FOREIGN PATENT DOCUMENTS

| | | | | |
|---|---|---|---|---|
| WO | 2004/007683 A2 | 1/2004 | | |
| WO | 2012/056109 A2 | 5/2012 | | |
| WO | WO-2012056109 A2 * | 5/2012 | ............... A61K 9/06 | |
| WO | 2013/117823 A1 | 8/2013 | | |
| WO | 2014/049204 A1 | 4/2014 | | |
| WO | 2014/071137 A1 | 5/2014 | | |
| WO | 2014/091086 A1 | 6/2014 | | |
| WO | 2014/128354 A1 | 8/2014 | | |
| WO | 2014/186430 A1 | 11/2014 | | |

OTHER PUBLICATIONS

Rimann et al. "Automation of 3D Cell Culture Using Chemically Defined Hydrogels" J of Laboratory Automation, 2014, vol. 19 (2), 191-197 (Year: 2014).*

Desbordes, et al., "High-Throughput Screening Assay for the Identification of Compounds Regulating Self-Renewal and Differentiation in Human Embryonic Stem Cells", Cell Stem Cell 2, 602-612, Jun. 2008.

Kameoka, et al., "A High-Throughput Screen for Teratogens Using Human Pluripotent Stem Cells", Toxicological Sciences, 137(1), 76-90, 2014.

Yan-Ru Lou, et al., "The Use of Nanofibrillar Cellulose Hydrogel As a Flexible Three-Dimensional Model to Culture Human Pluripotent Stem Cells", Stem Cells and Development, vol. 23, No. 4, 2014.

(Continued)

*Primary Examiner* — Allison M Fox
(74) *Attorney, Agent, or Firm* — Nixon Peabody LLP

(57) ABSTRACT

The present invention relates a method for chemical testing, comprising culturing cells in a first plant-derived nanofibrillar cellulose (NFC) hydrogel to obtain in vivo like cells; exposing the in vivo like cells to a test chemical; optionally within another plant-derived NFC hydrogel; incubating the exposed in vivo like cells; detecting during or after incubating, the impact of the test chemical on the in vivo like cells by at least one detection; and removing the plant-derived NFC hydrogel at least once at any stage after obtaining the in vivo like cells and before at least one detection used for detecting the impact of the test chemical on the in vivo like cells. The invention further relates to the use of plant-derived NFC hydrogel in a method for chemical testing, the use of in vivo like cells obtained by culturing cells in plant-derived NFC hydrogel for chemical testing and to a kit for chemical testing comprising plant-derived NFC hydrogel, instructions and a cell or test chemical library.

29 Claims, 27 Drawing Sheets

(56) References Cited

OTHER PUBLICATIONS

Madhushree Bhattacharya, et al., "Nanofibrillar cellulose hydrogel promotes three-dimensional liver cell culture", Journal of Controlled Release, 164, 2012, 291-298.
Yan-Ru Lou, et al., "Silica bioreplication preserves three-dimensional spheroid structures of human pluripotent stem cells and HepG2 cells", Scientific Reports, Published Sep. 1, 2015.
Vesa Hongisto, et al., "High Throughput 3D Screening Reveals Differences in Drug Sensitivities between Culture Models of JIMT1 Breast Cancer Cells", PLOS ONE, Oct. 2013, vol. 8, Issue 10.
Salman R. Khetani, et al., "Microscale culture of human liver cells for drug development", vol. 26, No. 1, Jan. 2008, Nature Biotechnology.
Salman R. Khetani, et al., "Use of Micropatterned Cocultures to Detect Compounds That Cause Drug-Induced Liver Injury in Humans", Toxicological Sciences, 132(1), 107-117, 2013.
Search Report, Patent Application No. 20146115, dated Mar. 17, 2015.
Emer Fitzpatrick et al., "Coculture With Mesenchymal Stem Cells Results in Improved Viability and Function of Human Hepatocytes", Cell Transplantation, vol. 24, pp. 73-83, 2015.
Anastasia Bachmann et al., "3D Cultivation Techniques for Primary Human Hepatocytes", Microarrays, 2015, 4, 64-83.

\* cited by examiner

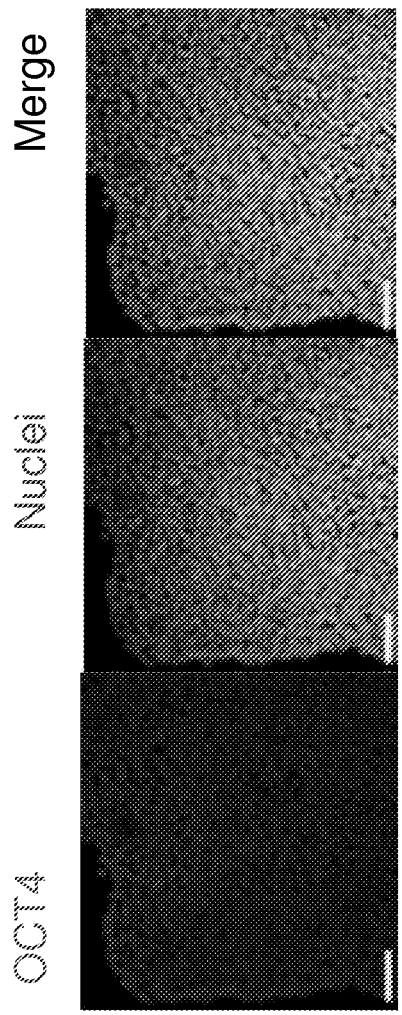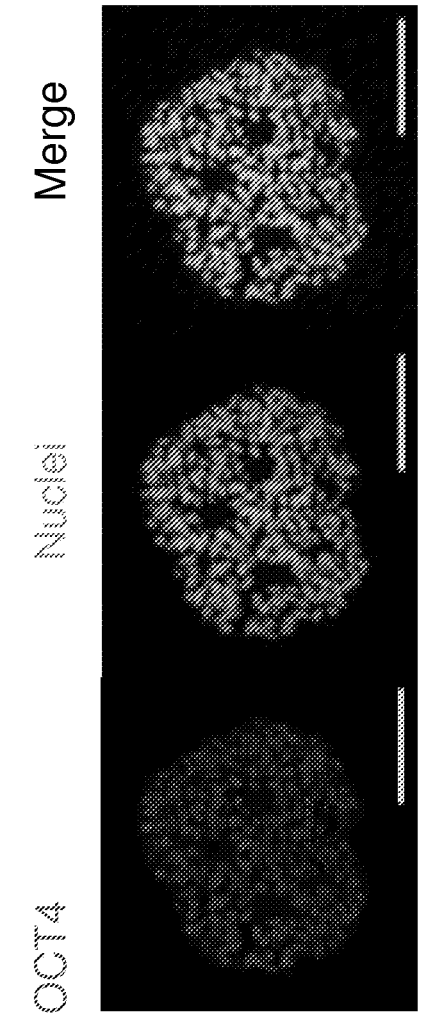
Fig. 2b
Fig. 2c

| IF | 0.5% NFC | | | 0.75% NFC | | | 1.0% NFC | |
|---|---|---|---|---|---|---|---|---|
| | Day 6 | Day 9 | | Day 6 | Day 9 | | Day 6 | Day 9 |
| HNF3B | ++ | + | HNF3B | - | - | HNF3B | ? | - |
| CXCR4 | + | + | CXCR4 | ++/- | + | CXCR4 | ++ | ++/+ |
| OCT4 | ++ | + | OCT4 | -/+ | +/- | OCT4 | ? | + |
| NANOG | ++ | + | NANOG | +/++ | + | NANOG | ? | - |
| AFP | - | +/- | AFP | +/- | - | AFP | ? | - |

Fig. 14

| IHC | 0.5% NFC Day 6 | | IHC | 0.75% NFC Day 6 | | IHC | 1.0% NFC Day 6 |
|---|---|---|---|---|---|---|---|
| HNF3B | + | | HNF3B | + | | HNF3B | + |
| CXCR4 | + | | CXCR4 | ++ | | CXCR4 | ++ |
| B-tub | - | | B-tub | - | | B-tub | + |
| MA | - | | MA | - | | MA | - |

Fig. 16

| IF | 0.5% NFC | 0.75% NFC | 1.0% NFC |
|---|---|---|---|
| HNF4A | +/- | +/- | +/- |
| CK19 | + | + | + |
| AFP | +/- | +/- | - |
| ALB | - | - | - |

Fig. 20

| IHC | 0.5% NFC | 0.75% NFC | 1.0% NFC |
|---|---|---|---|
| SSEA4 | - | +/- | - |
| HNF3B | + | - | + |
| CXCR4 | ++ | +++ | ++ |
| HNF4A | +/- | - | - |
| CK19 | +/+++/- | +++/- | ++/- |
| AFP | - | +++ | +/- |
| ALB | - | - | - |

Fig. 24

PLANT-DERIVED NANOFIBRILLAR CELLULOSE HYDROGEL FOR CELL CULTURE AND CHEMICAL TESTING

CROSS-REFERENCE TO RELATED APPLICATIONS

This application is a U.S. National Stage of International Application No. PCT/FI2015/050910, filed on Dec. 18, 2015, which claims priority to Finnish Patent No. 20146115, filed Dec. 18, 2014, the contents of each of which are incorporated herein by reference in their entireties.

FIELD

The present invention relates generally to a process where nanofibrillar cellulose hydrogel is used for culturing in vivo like cells which are then used in chemical testing, for example toxicity testing, safety testing, drug testing or screening. More particularly, the invention relates to a method for chemical testing, comprising culturing cells on or in a first plant-derived nanofibrillar cellulose (NFC) hydrogel; obtaining in vivo like cells; exposing the in vivo like cells to a test chemical; optionally within another plant-derived NFC hydrogel; incubating the exposed in vivo like cells; detecting during or after incubating, the impact of the test chemical on the in vivo like cells by at least one detection; and removing the plant-derived NFC hydrogel at least once at any stage after obtaining the in vivo like cells and before at least one detection used for detecting the impact of the test chemical on the in vivo like cells.

The invention further relates to the use of plant-derived NFC hydrogel in a method for chemical testing, the use of in vivo like cells obtained by culturing cells on or in plant-derived NFC hydrogel for chemical testing and to a kit for chemical testing comprising plant-derived NFC hydrogel.

BACKGROUND

There is an increasing interest in in vitro models for drug and chemical testing in order to reduce, refine and replace the use of animals. Although animal experiments are still an important part of pharmaceutical research, animal experiments may not mirror human due to the interspecies differences in drug biotransformation. Depending on the pharmacokinetic parameter the translation from animal (usually mouse, rat) to human may be impossible or feasible. It is known that the overall volume of drug distribution is governed by nonspecific drug binding and partitioning to the tissues and this is similar in man and animals, but prediction of drug distribution to individual cell types or tissues in humans is more challenging. Thus, animal experiments may fail to predict the safety or effectiveness problems. Poor translation of animal results to the humans (about 90% of the drug candidates fail in the clinical studies) has been addressed by FDA. Furthermore, animal experimentation has been criticized for decades on the basis of ethical and reliability problems.

Examples of current in vitro liver models for drug discovery and chemical testing comprises human liver slices (in vivo microenvironment), human primary hepatocytes, human based hepatic cell lines, stem cell derived hepatic cells, liver microsomes and recombinant drug-metabolizing enzymes. However, the dissatisfaction with current liver cell models has promoted the development of numerous new cell culture techniques for liver cells to retain hepatocyte phenotype and functions. The most widely adopted technologies are culture medium modifications, culture matrix modification, co-culturing with non-parenchymal cells, three-dimensional culture techniques and bioreactor and refusion techniques.

Culture experiments with human cells avoid the pitfalls of the species differences. However, although cell models are nowadays widely used in pharmaceutical research and development, their value is not always evident. Mostly cell culture experiments are carried out in 2D format using conditions that may be quite different from the real physiological situations. Taken the environmental factors in cell growth and differentiation, the differences of cell culture conditions may lead to erroneous conclusions in the experiments. Therefore, there is a continuing need for improved cell culture systems that would result in proper cellular phenotype, and more reliable cell based research in many fields of biomedicine. Artificial extracellular matrix (ECM) mimicking 3D matrices have emerged as a potential strategy towards more realistic in vivo like cell culture systems. The 3D matrices (i.e. cell culture scaffolds), are based on natural and/or synthetic biomaterials. In essence, the scaffold should lead to cellular functions that are identical to the native state of the particular cell type.

Recently, the interest has arisen to apply plant derived NFC in various areas, including biomedical and pharmaceutical applications as well as tissue engineering. In higher plants, cellulose is organized in morphologically complex structure consisting of $\beta(1\rightarrow4)$ D-glucopyranose chains. These chains are laterally bound by hydrogen bonds to form microfibrils with a diameter in nanoscale, which are further organized in microfibril bundles. Furthermore, cellulose molecules are associated with other polysaccharides (hemicelluloses) and lignin in plant cell walls, resulting in even more complex morphologies. The cellulose nanoscale fibers can be released from the highly ordered structure by various methods resulting in different grades of nanosized celluloses.

Despite the ongoing research and development in the area there is still a need for more reliable in-vitro models. For example optimized cell culture systems have enormous potential in basic biomedical research, drug development, and cell-based transplantations. Predictive cell models for preclinical drug discovery are needed to improve the current success rate of 10% in clinical drug testing.

Drug discovery and development is a complicated process that takes in average 10-15 years. The entire process is comprised of several stages from target identification through preclinical studies to clinical trials in humans. Only $\frac{1}{10}$ of compounds that enter clinical trials qualifies through the process and reaches the market. This means that preclinical studies are not able to properly predict the behavior of novel compounds in the human body. Especially predictive ability and reproducibility of preclinical tests need improvement.

There is also still a need for the development, harmonization and use of generally acceptable, scientifically sound methodologies for the evaluation of risks to human health from exposure to chemicals of different kind in order to provide improved methods for chemical testing.

SUMMARY OF THE INVENTION

It was surprisingly found that plant-derived NFC hydrogels have properties that are highly beneficial in culturing in vivo like cells for use in chemical testing, especially in testing chemical toxicity and safety, in drug and pre-drug testing and in drug screening.

One embodiment relates to a method for chemical testing, comprising;
a) culturing cells on or in a first plant-derived nanofibrillar cellulose (NFC) hydrogel to obtain in vivo like cells;
b) exposing the in vivo like cells to a test chemical; optionally within another plant-derived NFC hydrogel;
c) incubating the exposed in vivo like cells;
d) detecting, during or after incubating the impact of the test chemical on the in vivo like cells by at least one detection, and
e) removing the plant-derived NFC hydrogel at least once at any stage after stage a) and before at least one detection according to stage d).

Exposing the in vivo like cells to a test chemical, incubating the exposed in vivo like cells and detecting the impact of the test chemical on the in vivo like cells may partly take place at the same time.

It has now been found that suitable cells and methods for chemical testing are obtained when cells are cultured in plant-derived NFC hydrogel. Preferable features of the plant-derived NFC hydrogel, which benefits the invention, is that it is inert; non-toxic; non-pyrogenic; easy and inexpensive to manufacture. Moreover, the rheology of plant-derived NFC hydrogels show reversible gelation. At high stress levels, valid for injections, a fluid-like behavior is observed whereas at low stress level and quiescent conditions a step-wise transition to solid-like behavior. NFC hydrogel is a so-called physical or reversible gel, meaning that the network of hydrated and entangled cellulose nanofibrils in the NFC hydrogel is formed spontaneously without a need for further components such as cross-linkers. The interactions holding the networks together are reversible and can be disrupted e.g. by application of high stress. Upon removal of the stress the network is spontaneously formed again. In that regard the NFC hydrogel may be seen as a true one-component gel. The viscoelastic properties of the NFC hydrogels are similar to those of physiological ECMs. Thus, the plant-derived NFC hydrogel is easy to handle and dispense, since it can be handled at room temperature, using automation; it is immediately ready for use; it is flexible and possible to modify with cells inside, i.e. to dilute or to add NFC; and thereto it does not contain protein residues. The plant-derived NFC hydrogel used is preferably transparent, light stable, electricity stable, and particularly native NFC is free of chemical residue. The in vivo like cells within the hydrogel formed in cell culture media are possible to recover. The preferred NFC hydrogel is further highly stable, it may be stored at any desired temperature and it can be sterilized.

One embodiment relates to chemical testing of in vivo like cells cultured in NFC hydrogel. One aspect relates to a method of culturing in vivo like cells in NFC hydrogel, conducting safety testing, toxicity testing or drug screening by exposing the cultured in vivo like cells with one or more test chemicals to be tested and detecting qualitatively or quantitatively the impact of the test chemical(s) on the in vivo like cells e.g. by observing the cells, or by detecting presence or residual amounts of the test chemical(s) or the presence or amounts of formed metabolites.

A further embodiment relates to a process where plant-based NFC is used in chemical testing comprising culturing in vivo like cells on or in a NFC hydrogel; contacting the in vivo like cells with test chemical, for example a drug candidate or pro-drug candidate; incubating the in vivo like cells; and measuring the impact of the test chemical, for example the drug or pro-drug on the cells, for example by testing for cell viability or formed metabolites. One aspect relates to the use of plant-derived NFC hydrogel in a method for chemical testing, wherein a NFC hydrogel is used for culturing cells on or in said hydrogel to obtain in vivo like cells; said in vivo like cells are exposed to a test chemical; the exposed in vivo like cells are incubated; and the impact of the test chemical on the in vivo like cells is detected by at least one detection; wherein the plant-derived NFC hydrogel is removed at any stage between the in vivo like cells are obtained and before a last detection of the impact of the test chemical on the in vivo like cells.

One further aspect relates to the use of in vivo like cells obtained by culturing cells on or in plant-derived NFC hydrogel for chemical testing, which use comprises removing the plant-derived NFC hydrogel before detecting the impact of a test chemical on the in vivo like cells.

One further aspect is providing a kit for chemical testing comprising plant-derived NFC hydrogel; instructions for carrying out the described method for chemical testing; and at least one library chosen from a cell library and a test chemical library.

Particularly the embodiments relate to chemical testing which is of importance for humans, animals as well as for the environment.

Whilst the above considerations mainly apply to chemical testing in embodiments in relation to man and human applications, it will be appreciated that finding more accurate testing methods is important for applications relating to other animals as well, particularly in the veterinary field in the treatment of animals like domestic animals (e. g. horses, cattle, dogs, cats).

Characteristic features of the invention are provided in the appended claims.

Definitions

Unless defined otherwise, all technical and scientific terms used in the specification and claims have the same meaning as commonly understood by one of ordinary skill in the art in the field of nanocellulose technology, as well as in the field of cell culture and chemical testing. Specifically, the following terms have the meanings indicated below. As used herein, the term "nanofibrillar cellulose" or nanofibrillated cellulose or NFC is understood to encompass plant-derived nanofibrillar structures including fibrils and fibril bundles liberated from cellulose-based fiber material, or cellulose pulp. The nanofibrillar structures liberated from cellulose-based fiber raw material are characterized by a high aspect ratio (length/diameter): their length may exceed 1 µm, whereas the diameter typically remains smaller than 200 nm. The smallest nanofibrils are in the scale of elementary fibrils, the diameter being typically in the range of 2-12 nm. The dimensions and size distribution of the fibrils depend on the disintegration method and efficiency, and on pretreatment. Typically the median length of fibrils or fibril bundles in NFC is not greater than 100 µm, for example in the range of 1-50 µm, and the number average diameter of the fibrils or fibril bundles is smaller than 200 nm, suitably in the range of 2-100 nm. Intact, unfibrillated microfibril units may be present in the nanofibrillar cellulose but only in insignificant amounts. The nomenclature relating to nanofibrillar celluloses is not uniform and there is an inconsistent use of terms in the literature. For example the following terms have been used as synonyms for nanofibrillar cellulose: cellulose nanofiber, nanofibril cellulose (CNF), nanofibrillar cellulose, nano-scale fibrillated cellulose, microfibrillar cellulose, cellulose microfibrils, microfibrillated cellulose (MFC), and fibril cellulose. As used herein, the nanofibrillar cellulose is not meant to encompass non-fibrillar, rod-shaped cellulose nanocrystals or whiskers.

The term "cellulose pulp" refers to cellulose fibers, which are isolated from any plant based cellulose or lignocellulose raw material, using chemical, mechanical, thermo-mechanical, or chemi-thermo-mechanical pulping processes, for example kraft pulping, sulfate pulping, soda pulping, organosolv pulping. The cellulose pulp may be bleached using conventional bleaching processes. The cellulose pulp does not contain substantial amounts of lignin, or it contains only traces of lignin or non-detectable amounts of lignin. Thus also the NFC may be essentially lignin-free.

The term "native cellulose pulp" or "native cellulose" refers here to any cellulose pulp, which has not been chemically derivatized after the pulping process and the optional bleaching process, but may have been otherwise treated to make the material more susceptible to disintegration into nanofibrils for example by washing, ion-exchange of carboxyl groups with $Na^+$, or enzymatically. "Native nanofibrillar cellulose" refers to NFC manufactured by mechanical disintegration of the native cellulose pulp.

The term "anionically modified cellulose pulp" or "anionically modified cellulose" refers to cellulose pulp that has been modified chemically by adding anionic charges to the cellulose so as to make the cellulose pulp labile and thereby more susceptible to mechanical disintegration into nanofibrils. Anionically modified cellulose pulp may be manufactured from cellulose pulp e.g. by oxidation such as TEMPO-mediated oxidation, by sulphonation or by carboxymethylation, "Anionic nanofibrillar cellulose" refers to NFC manufactured by mechanical disintegration of the anionically modified cellulose pulp.

Nanofibrillar cellulose is characterized by a large specific surface area and a strong ability to form hydrogen bonds. Hydrophilicity of nanofibrillar cellulose is due to the presence of hydroxyl groups in the glucoside rings and partially charged hemicellulose moieties. In an aqueous environment, a dispersion of cellulose nanofibrils forms a viscoelastic hydrogel network by entanglement of nanofibrils and secondary forces such as hydrogen bonds and ionic interactions. The hydrogel is formed at relatively low nanofibril concentrations of for example 0.05-0.2% w/w. As used herein the term "hydrogel" in connection with nanofibrillar cellulose refers to a form where an aqueous dispersion of the nanofibrillar cellulose has a loss tangent less than 1. Loss tangent values measure the ratio of loss modulus $G''$ to storage modulus $G'$ ($G''/G'$).

The term "test chemical(s)" as used herein refer to a variety of materials, substances or compounds whose impact on the in vivo like cells is to be tested. Test chemical(s) may be chemical substances; organic or inorganic chemical compounds; or chemical mixtures containing more than one chemical substance or ingredient and not having a fixed composition; or biological agents or fragments thereof such as pathogens, antigens, epitopes, or antibodies; or any combinations thereof. Test chemical may be for example a drug candidate or a prodrug candidate, or a potentially hazardous agent whose safety or toxicity is being studied. As used herein, the term test chemical may refer also to a set of test chemicals applied to the in vivo like cells according to a test scheme or pattern.

The term "chemical testing" as used herein refers to a procedure for determining qualitatively or quantitatively e.g. the presence, absence, extent or amount of an impact a test chemical or certain pattern of test chemicals may have on the cells exposed thereto. The term chemical testing refers for example to safety testing, toxicity testing, pre-drug testing as well as drug screening.

The term "exposing" as used herein refers to subjecting the in vivo like cells to an action or influence of a test chemical. Exposing may be for example continuous or intermittent exposing, and of any duration such as temporary, short-term or long-term exposing. Exposing may also involve subjecting the in vivo like cells to a set of test chemicals following a specific test scheme or pattern.

The term "incubating" as used herein refers to maintaining the in vivo like cells under desired conditions either while being exposed to the test chemical i.e. in the presence of the test chemical, or after being exposed to the test chemical but in the absence thereof. Incubating may also involve e.g. providing fresh culture media.

The term "removing" as used herein in connection with NFC hydrogel refers to removing the NFC hydrogel by breaking down the structure of the NFC network to such an extent that the cells are not anymore encapsulated or supported by the hydrogel. Break-down products of the hydrogel, such as glucose in case of using cellulase for the removing, may remain in the system.

The term "detecting" as used herein refers to any qualitative or quantitative determination of the impact of a test chemical on the in vivo like cells, or a combination of qualitative and quantitative determinations. Typically detecting involves a plurality of detections using different techniques.

The term "cells" as used herein refer to any eukaryotic cells having their origin in multicellular organisms of the Metazoa, such as mammals, such as humans, and used for seeding, for example in co-cultures such as tissue culturing, as well as to the in vivo like cells obtained by 3D culturing.

The term "in vivo like cells" as used herein refer to cells cultured in vitro but having similar phenotype and morphology as in in vivo conditions. The in vivo like cells represent for example cell-cell and cell-extracellular matrix interactions. The in vivo like cells may be in the form of clusters, cell spheroids, other 3D cell formations or in vivo like 2D cells.

BRIEF DESCRIPTION OF THE DRAWINGS

FIG. 14. Summary of the protein expressions in differentiated spheroids studied by immunofluorescence (IF).

FIG. 16. Summary of the protein expressions in differentiated cells inside spheroids studied by immunohistochemistry (IHC).

FIG. 20. Summary of protein expressions in differentiated spheroids from pluripotent until hepatic progenitor (HP) stage studied by immunofluorescence (IF).

FIG. 24. Summary of the protein expressions in differentiated cells inside spheroids studied by immunohistochemistry (IHC).

DETAILED DESCRIPTION OF THE INVENTION

Figure 1:
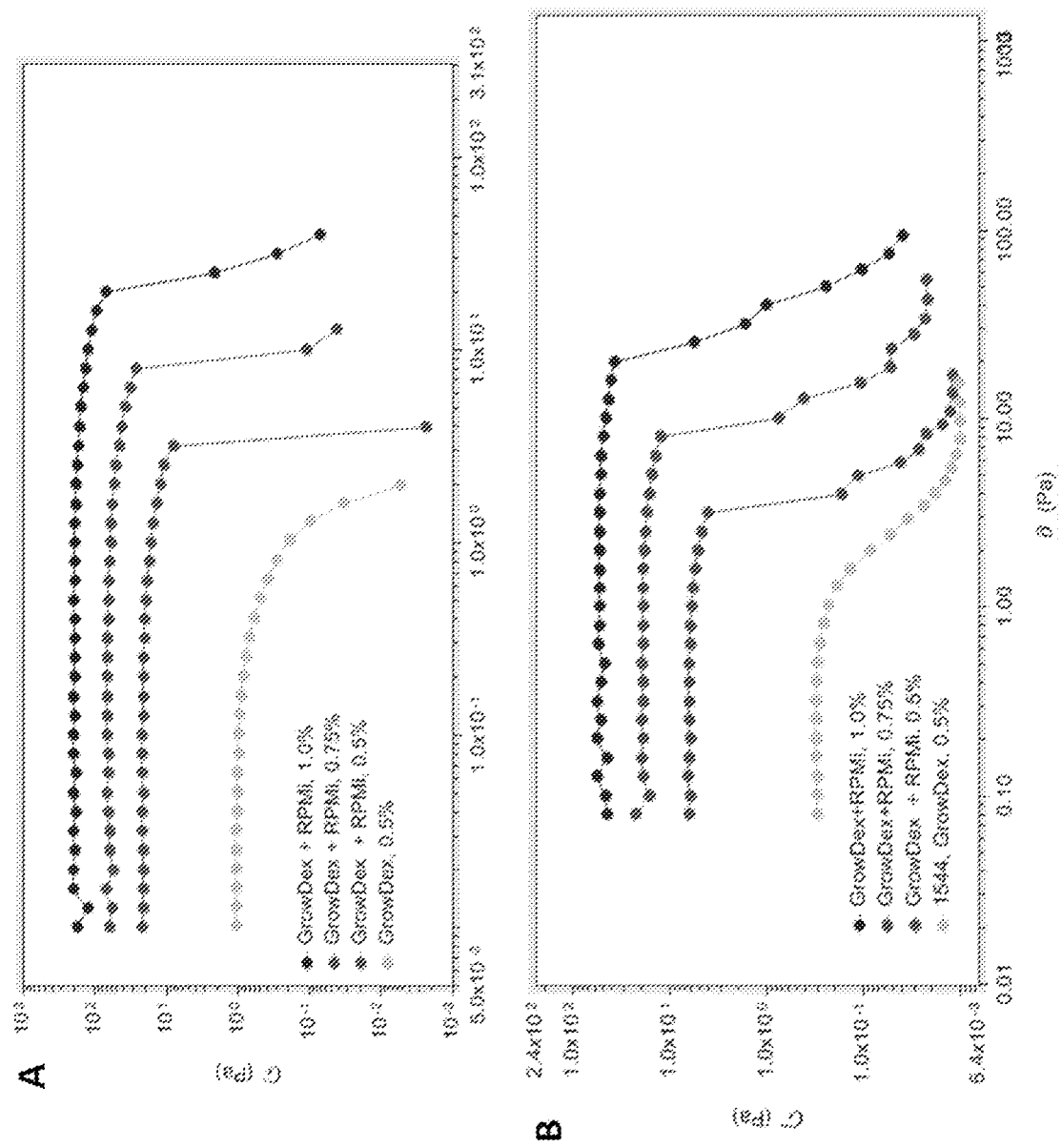
FIG. 1. Rheological properties of nanofibrillar cellulose (NFC) hydrogel (GrowDex) mixed with RPMI-1640 growth medium. Flow curves of measured hydrogels are presented as a function of shear stress of (A) storage modulus ($G'$) and (B) loss modulus ($G''$).

The invention on hand relates to the use of NFC hydrogel for culturing in vivo like cells and using these in vivo like cells for chemical testing. The chemical testing especially relates to toxicity testing; safety testing; drug candidate testing; drug screening; or pro-drug candidate testing.

The following aspects all relates to the different embodiments and aspects of the invention.

The chemical testing according to one embodiment relates to culturing in vivo like cells in NFC hydrogel. The cells can be maintained and optionally proliferated on or in the biomaterial media, i.e. in the hydrogel, without animal or human based components originating outside the cells. The cells may be evenly dispersed on or in the NFC hydrogel media/matrix. Cells divide on or in the media, start to proliferate and the cell clusters start to grow spontaneously without the accumulation of cells on the bottom of the cell culture platform. The homogenous dividing of the cells in the NFC hydrogel is a prerequisite for the biomaterial to function as 3D cell culture media.

The in vivo like cells are alternatively kept in the first NFC hydrogel during the chemical testing or then the in vivo like cells are removed from the first hydrogel and the cell clusters are tested for example in another hydrogel or another media, typically in a liquid. The in vivo like cells do not necessary need to be transferred from the plant-derived hydrogel during testing or detecting of the impact of the test chemical on the in vivo like cells.

The method is especially useful for testing new chemicals. The chemical, for example the drug testing typically comprises testing cell viability after incubating the in vivo like cells contacted with the chemical or drug, but the testing may also comprise testing metabolites formed or testing the processes (mechanisms) and production of metabolites of the used new chemical entities. The NFC hydrogel is inert and neutral with regard to its metabolite profile and therefore well suited for such chemical testing. Another preferred embodiment relates to pro-drug testing where the in vivo like cells, for example the cell spheroids, or co-cultures of different types of cells, are contacted with the pro-drug candidate to be tested. Typically testing pro-drug candidates comprises measuring whether the in vivo like cells have turned a pro-drug molecule into an active drug form. Screening drugs typically comprises detecting whether the in vivo like cells have metabolized the drug molecules to metabolites after incubating the cells contacted with the drug.

Hydrogel Composition

Hydrogels, both of synthetic and natural origin, have recently emerged as suitable scaffolds for 3D cell culture. However, commercial products for 3D cell culturing such as for example cell culture matrices PuraMatrix™ (3DM Inc.) and Matrigel (BD Biosciences) have certain disadvantages when it comes to cell culturing and which are disadvantages also what comes to chemical testing such as chemical toxicity and safety testing.

PuraMatrix™ is a hydrogel of self-assembled peptide nanofibers which resembles the structure of natural fibrillar collagen in ECM with fiber diameter 5-10 nm. It has also high water content, typically 99.5%. U.S. Pat. No. 7,449,180 and WO 2004/007683 disclose peptide hydrogels. Matrigel is gelatinous protein mixture secreted by mouse tumor cells. The mixture resembles the complex extracellular environment found in many tissues and is used by cell biologists as a substrate for cell culture. MaxGel™ ECM Matrix (Sigma-Aldrich), which includes a mixture of human ECM components, forms a gel in ambient temperature. Typically, in these systems the pluripotent cells are separated from the cell culture matrix by protease treatment which breaks extracellular protein network used by the cells to attach themselves to the cell culture matrix and to neighbouring cells.

Further, bacterial cellulose (BC) has also been used as a scaffold in cell culture. The limitation in the use of bacterial cellulose in stem cell culture is the inherent structure of the fermented material: Upon cultivation, BC is formed as very tight membranes in air-water interphase in the fermenter. The formed membranes are too tight for 3D cell culturing and various modifications. If used as cell culture matrix, the porosity of the BC matrix has to be increased for adequate cell penetration and formation of cell clusters. Furthermore, any bacterial residues present in the bacterial cellulose material may influence the cultured cells or may affect the results or give fault results in the detection stage of the chemical testing.

Present 2D and 3D cell culture systems for pluripotent cell cultures, such as stem cells, rely on animal based matrices. Animal based compounds in cell culture environment generate a risk of immunoreactions and different types of toxicity issues in cell culture and downstream applications. Further, harvesting cells from cell culture matrices composed of proteinaceous material requires treating the cell culture with protein degrading enzyme such as protease, which also hydrolyses extracellular structures of the cultured cells. Thereto such proteinaceous material may coagulate or denature if chemicals which cause coagulation are tested on the cells within the hydrogel.

The NFC hydrogel refers here to an aqueous dispersion comprising plant-derived NFC. The viscoelastic properties of plant-derived NFC hydrogel scaffold differ considerably from previously studied bacterial cellulose scaffolds. It is injectable due to fluid-like behavior at high stress due to reversible gelation and rheological characteristics allow mixing of cells into the gel. The spontaneously formed gel state after injection provides the required mechanical support for cell growth and differentiation. Beneficial properties of NFC are based on its unique nanofibrillar structure resembling closely the extracellular matrix. Thereto the NFC hydrogel is formed already at a low consistency in an aqueous medium and the gel is thereto preferably suitably transparent and the stiffness of the NFC hydrogels can be easily adjusted by dilution, even with cells cultured within the gel. The plant-derived native NFC hydrogel thus can be used as a cell culture scaffold and forms an environment for in vivo like cells for example induced spheroid formation of 3D HepaRG and HepG2 cells.

For example Matrigel, mentioned in Hongisto et al. (Hongisto et al., PLOS ONE, October 2013, Vol. 8 (10), High-Throughput 3D Screening Reveals Differences in Drug Sensitives between Culture Models of JIMT1 Breast Cancer Cells) for drug sensitivity testing and high-throughput screening, need to be prepared beforehand and it is not possible to dilute the hydrogel after preparation and change for example stiffness with cells inside. Thereto this type of hydrogel gels or polymerizes in room temperature and thus need to be prepared and worked with in a cold environment. If the cells are already cultured and the hydrogel polymerizes the cells may suffer if the hydrogel is cooled down. The cold gel may also stress the cells.

The NFCs particularly suitable for use in the hydrogel are selected from plant-derived native NFCs, anionic NFCs and any combinations thereof. Examples of suitable NFCs and their manufacturing methods have been described for example in WO2013/117823, WO2012/056109, WO2014/128354, or WO2014/091086.

The dimensions of the fibrils or fibril bundles of the NFC are dependent on the raw material and the fibrillation method. As the starting material, any plant-based cellulose or lignocellulose raw material may be used. The plant material may be wood. The wood may be from softwood trees such as spruce, pine, fir, larch, douglas fir or hemlock, or from hardwood trees such as birch, aspen, poplar, alder, eucalyptus or acasia, or from a mixture of softwood and hardwood. Nonwood material may be from for example agricultural residues, grasses or other plant substances, such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed. The cellulose fibers may be isolated from the plant based cellulose or lignocellulose raw material using chemical, mechanical, thermo-mechanical, or chemi-thermo-mechanical pulping processes, for example kraft pulping, sulfate pulping, soda pulping, organosolv pulping. The cellulose pulp may be bleached using conventional bleaching processes.

The term fibrillation may be used interchangeably with expression disintegration, and generally refers to disintegrating cellulose pulp mechanically by work applied to the fibers, where cellulose fibrils are liberated from the fibers or fiber fragments. The work may be based on various effects, like grinding, crushing or shearing, or a combination of these, or another corresponding action that delaminates the cell walls of the fibers and liberates fibrils. The energy taken by the refining work is normally expressed in terms of energy per processed raw material quantity, in units of e.g. kWh/kg, MWh/ton, or units proportional to these. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegration is performed at conditions wherein water is sufficiently present to prevent the formation of bonds between the fibers. Typically the NFC hydrogel is manufactured in consistency of from 0.05 to 10% w/w, such as from 0.1 to 4% w/w, such as from 0.12 to 1.2% w/w, said consistencies being convenient for the fibrillation and the handling of the NFC hydrogel.

It is also important to minimize the microbial contamination of the cellulose pulp before and during the mechanical disintegration, such as fibrillation. For example, prior to fibrillation/mechanical disintegration, it is advantageous to aseptically collect the cellulose pulp from the pulp mill immediately after bleaching stage when the pulp is still sterile. Depending on the use, also the microbial purity of the NFC hydrogel is important. Thus the aqueous medium used in the hydrogel may suitably be purified water or sterilized water, preferably purified pyrogen-free water. Typically the NFC hydrogel may be sterilized prior to use, suitably using any suitable sterilization method known in the art.

Different grades of NFC may be categorized based on three main properties: (i) size distribution, length and diameter (ii) chemical composition, and (iii) rheological properties. To fully describe a grade the properties may be used in parallel. Examples of different grades include native NFC, oxidized NFC and carboxymethylated NFC. Within these grades, also sub-grades exist, for example: extremely well fibrillated vs. moderately fibrillated, high degree of substitution vs. low, low viscosity vs. high viscosity etc.

The number average diameter of plant-derived NFC may vary from 1 to 100 nm, such as from 1 to 50 nm, or 2 to 15 nm. The smallest nanofibrils are similar to so called elementary fibrils. The dimensions of the nanofibrils or nanofibril bundles are dependent on raw material, pretreatment and disintegration method. Typically, native or non-derivatized grades have larger diameters and wider fibril size distribution while the derivatized grades have smaller diameters and narrower size distributions. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general AFM and TEM suit best for NFC grades with narrow fibril diameter distribution.

Optical properties of different types of NFC hydrogels can be evaluated by turbidity measurements of dilute NFC hydrogels. For example NFC having number average diameter of 1-40 nm provides transparency to the hydrogel. Generally the turbidity of the plant-derived NFC hydrogel may be 200 NTU or less, such as 150 NTU or less, or 100 NTU or less. The turbidity may vary from 200 to 1 NTU, such as from 150 to 4 NTU, or from 100 to 5 NTU in water at concentration of 0.1 w %. Typically, hydrogels made from the anionic NFC materials are more transparent when compared to native grades due to smaller fibril diameters. Turbidity may be measured quantitatively using optical turbidity measuring instruments. There are several commercial turbidometers available for measuring quantitatively turbidity. One method used is based on nephelometry. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample. In one turbidity measurement method, a NFC sample is diluted in water, to a concentration below the gel point of said NFC, and turbidity of the diluted sample is measured. Said concentration where the turbidity of the NFC samples is measured is 0.1 wt %. HACH P2100 Turbidometer with a 50 ml measuring vessel is used. The dry matter of the NFC sample is determined (e.g. according ISO 4119/1995 with the exception that t=16 h) and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. The mean value and standard deviation are calculated from the obtained results, and the final result is given as NTU units.

The number average diameters of the native NFCs may vary from 4 to 100 nm, such as 6-50 nm, such as 6-10 nm. Turbidity of the native NFC hydrogel may be 200 NTU or less, such as 150 NTU or less, or 130 NTU or less. The turbidity may vary from 200 to 50 NTU, such as from 150 to 80 NTU, such as from 130 to 100 NTU in water at concentration of 0.1 w %.

The anionic NFCs are typically thinner, the number average diameter may vary from 1 to 50 nm, such as 1-20 nm, such as 2-6 nm. Turbidity of the anionic NFC hydrogel may be 100 NTU or less, such as 80 NTU or less, or 30 NTU or less. The turbidity may vary from 100 to 4 NTU, such as from 80 to 4 NTU, such as from 30 to 5 NTU in water at concentration of 0.1 w %.

The length of NFC is somewhat challenging to measure accurately, but rough estimates for length of native NFC grade is between 1 to 100 micrometer, such as 1-50, or 5-20 micrometers. The anionic NFC are somewhat shorter; length may vary between 0.3-50 micrometers, such as 0.3-20 micrometers, or 0.5-10 micrometers. These values are estimated from CRYO-TEM, SEM or AFM images. The most accurate estimates are based on Cryo-TEM images.

The degree of fibrillation can be evaluated from fiber analysis where number of larger, only partially fibrillated entities, are evaluated. For the plant-derived NFC the number of those particles per mg of dry sample may vary from 0 to 5000, such as from 0 and 1000, or from 0 to 200. For non-derivatized native NFC the number of non-fibrillated particles/mg may be somewhat higher than for anionic NFC. The fiber analysis may suitably be carried out using Fiber-Lab method.

The chemical compositions of the grades also vary. Depending on the raw material source, e.g. HW vs. SW pulp, different polysaccharide composition exists in the final NFC product. The cellulose pulp may be bleached using conventional bleaching processes. Preferably the cellulose pulp does not contain substantial amounts of lignin, or it contains only traces of lignin or non-detectable amounts of lignin. Thus also the NFC may be essentially lignin-free. NFC may contain some hemicelluloses; the amount is dependent on the plant source and pulping conditions. The hemicellulose content may vary between and 30 w %, such as 18 and 28 w %. For example bleached birch pulp has high xylose content (25% by weight) and negligible lignin content. Detailed chemical analysis is not possible—the nanofibrillar celluloses are always complicated mixtures of different polysaccharide structures.

Anionic NFC may be blended with native NFC for enhancing binding of certain compounds to the gel or varying other properties etc. Anionically modified cellulose pulp may also be blended with native cellulose pulp followed by the mechanical disintegration.

It is also possible to obtain derivatized NFC by incorporation of desired chemistry, such as by labelling the cellulose pulp before mechanical disintegration of the NFC.

The degree of substitution in the process for anionic modification of the cellulose pulp can vary broadly. For example, TEMPO or N-oxyl mediated oxidation may be conducted to charge values from 300 to 1500 micromol/g, such as from 600 to 1200 micromol/g, such as from 700-1100 micromol/g. The oxidized NFC may contain also aldehyde functional groups. Anionic modification via carboxymethylation or sulphonation may be conducted for cellulose pulp to ds levels from 0.05 to 0.30, such as from 0.08-0.25, or 0.10-0.20 prior to fibrillation. Carboxylate content may be analyzed from washed pulp samples for example by conductometric titration after protonating the carboxyls with acid and washing.

The cellulose pulp comprises both crystalline and amorphous regions in the cellulose. The crystallinity of the cellulose pulp used as starting material may be at least 50%. Suitably the crystallinity of the cellulose pulp is at least 55%, such as at least 60%, or at least 65%, or at least 70%. Examples of suitable crystallinity values of the NFC include from 50 to 85%, such as from 60% to 80%, or from 65 to 75%. The NFC consists essentially of cellulose I. The native NFC is of cellulose I. NFCs manufactured from anionically modified, especially carboxymethylated, cellulose pulp may contain minute amounts of other cellulose types depending on the modifying conditions. CP/MAS 13C-NMR spectra may be used for determination the crystallinity and type of cellulose.

As regards rheology, the NFC hydrogels are shear-thinning materials, which means that their viscosity depends on the speed (or force) by which the material is deformed. When measuring the viscosity in a rotational rheometer, the shear-thinning behaviour is seen as a decrease in viscosity with increasing shear rate. The hydrogels show plastic behaviour, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to verify the success of fibrillation and to describe the suspending power of the materials. These two parameters separate the different grades quite clearly and thus enable e.g. classification of the grades. Rheological measurements of the samples in the form of NFC hydrogels may be carried out with a stress controlled rotational rheometer (ARG2, TA instruments, UK) equipped with four-bladed vane geometry. Samples are diluted with deionized water (200 g) to a concentration of 0.5 wt % and mixed with Waring Blender (LB20E*, 0.5 l) 3×10 sec (20 000 rpm) with short break between the mixing. Rheometer measurement is carried out for the sample at pH 7. The diameters of the cylindrical sample cup and the vane are 30 mm and 28 mm, respectively, and the length 42 mm. The steady state viscosity of the hydrogels is measured using a gradually increasing shear stress of 0.001-1000 Pa. After loading the samples to the rheometer they are allowed to rest for 5 min before the measurement is started, room temperature. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of 1000 s−1 is exceeded. The method is used for determining both zero-shear viscosity and yield stress. The zero-shear viscosity of plant-derived nanofibrillar celluloses may vary from 1000 to 100000 Pas, typically the zero-shear viscosity varies from 2000 to 50000 Pas, in water at 0.5 wt % concentration. Typically the zero-shear viscosity of native NFC varies from 100 to 8000 Pas, such as 200 to 2000 Pas or 300 to 1000 Pas, in water at 0.5 wt % concentration. The anionic NFC is characterized by somewhat higher zero-shear viscosity typically varying from 1000 to 50000 Pas, such as 5000 to 30000 Pas, in water at 0.5 wt % concentration. The yield stress of plant-derived nanofibrillar celluloses may vary from 0.5 to 50 Pa, typically 1 to 20 Pa, in water at 0.5 wt % concentration. Typically the yield stress of native NFC varies from 0.5 to 8 Pa, such as 1 to 4 Pa, in water at 0.5 wt % concentration. The anionic NFC is characterized by somewhat higher yield stress typically varying from 1 to 50 Pa, such as 2 to 20 Pa or 3 to 15 Pa, in water at 0.5 wt % concentration. In the present method and uses high zero-shear viscosity and yield stress of plant-derived NFC provide for example good suspending capacity so that cells may be suspended evenly in the hydrogel and e.g. sedimentation of the cells is avoided, and the cells are protected from disturbances caused by handling of the cell cultures for example when changing growth medium, detecting by microscope etc. Especially cell spheroids may be fragile and prone to disintegration.

The viscoelastic properties storage modulus G', loss modulus G" and loss tangent (G"/G') of the NFC hydrogels may be determined with the frequency sweep in dynamic oscillation mode of the rheometer (strain 1% and 10%, frequency 0.1-100, temperature 25° C.). The stress sweep is measured in a shear stress range of 0.001-100 Pa at the frequency 0.1 Hz, at 25° C., pH 7. For determining whether a certain material is a gel, i.e. whether its loss tangent is <1, the measurement is performed in material's prevailing concentration, 1% strain, frequency of 0.1 Hz. For characterizing the gel forming capacity of a nanofibrillar cellulose grade the measurement is performed dispersed in pure water in 0.5 wt %, 1% strain, frequency of 0.1 Hz. The storage modulus of plant-derived nanofibrillar celluloses may vary from 0.1 to 100 Pa, typically the storage modulus varies from 1 to 50 Pa, in water at 0.5 wt % concentration. Typically the storage modulus of native NFC varies from 0.3 to 20 Pa, such as 1 to 10 Pa or 1 to 5 Pa, in water at 0.5 wt % concentration. The anionic NFC is characterized by somewhat higher storage modulus typically varying from 1 to 100 Pa, such as 2 to 50 Pa or 5 to 20 Pa. The viscoelastic measurements may also be used for characterizing the stiffness of the NFC hydrogel. Herein storage modulus G' is used for representing the stiffness. The stiffness of the NFC hydrogels reflects e.g. ease of spreading of the hydrogels. Stiffness of the plant-derived NFC hydrogel may be adjusted by diluting the stock hydrogel with e.g. sterile aqueous solution such as physiological saline, or buffer etc. Suitable stiffness of the hydrogel may be selected e.g. based on the needs of the cells or the chemical test. The stiffness may be selected e.g. to simulate the resistance present in vivo in the tissue or environment wherefrom the cells originate, representing e.g. the healthy or pathological condition. The stiffness may be for example at least 4 Pa, such as from 40 to 50000 Pa. The higher range stiffness values are obtained for higher concentrations, such as concentrations above 3 wt % or 4 wt %.

The features of the hydrogel are usually measured for a 0.5 wt % sample concentration. When the NFC hydrogel concentration is higher, this need to be taken into account during measuring. For example the shear stress need to be higher than the 0.001-1000 Pa range mentioned for 0.5 wt % concentration.

Concentration of the plant-derived NFC in the aqueous dispersion may vary from 0.05 to 10% w/w, such as from 0.1 to 4% w/w, such as from 0.12 to 1.2% w/w. The dry matter of NFC hydrogel sample may be determined according to ISO 4119/1995 with the exception that t=16 h.

The plant-derived NFC hydrogel may have a continuous hydrogel structure or a discontinuous structure such as continuous hydrogel broken into gel pieces. Manufacture and uses of such discontinuous hydrogel is disclosed in detail in WO2014049204.

Typical for homogeneous and continuous gel structures is high yield stress even at low concentrations. Respectively, discontinuous gel structures have typically lower yield stress value when compared to well activated cases even at the same concentration.

Cellulose nanofibers are typically very hydrophilic objects due to hydroxyl groups in the glucoside rings and partially charged hemicellulose moieties. Thus, the fibrils form hydrogel structures with a desired viscosity when dispersed in an aqueous medium, such as water at concentrations higher than the overlapping concentration, i.e. typically 0.05-0.2% w/v. Any suitable mixing or blending apparatus may be used. However, the efficacy of the mixing may influence to fine structure of the gel, i.e. more homogeneous gels are obtained with more efficient mixing apparatus. Since the gel structure is highly dependent on shear history of the sample: either continuous or discontinuous structures can be achieved depending on the mixing method after dilution.

Typically the hydrogel may comprise from 0.01 to 30 wt %, suitably from 0.01 to 20 wt % of NFC. Suitably said composition comprises from 0.05 to 5 wt %, particularly suitably from 0.07 to 4 wt %, even more suitably 0.1 to 3 wt % of NFC. The NFC is typically native NFC or anionic NFC such as oxidized NFC.

Although not necessary, bioactive agents can be added to the hydrogel to affect various activities or properties of the cells during the culturing of the cells. Such agents can relate for example to cell growth and proliferation, differentiation, migration or maintenance of undifferentiated states and the like. In some embodiments, the hydrogel optionally comprises nutritional agents, such as vitamins, essential and non-essential amino acids, essential and non-essential fats and combinations thereof. Such agents described above are not test chemicals within the meaning of the embodiments of the invention when added to the hydrogel before the in vivo like cells to be tested are obtained.

Cells, Cell Spheroids, In Vivo Like Cells

The cells, cultured in the NFC hydrogel can be of any cell type. They can include or comprise stem cells, primary and secondary cells and any combinations thereof. In some embodiments, the cells are selected from the group consisting of connective tissue cells, epithelial cells, muscle cells, neuronal cells, endothelial cells, fibroblasts, keratinocytes, smooth muscle cells, stromal cells, mesenchymal cells, immune system cells, hematopoietic cells, dendritic cells, hair follicle cells and combinations thereof. The nanofibrillar cellulose hydrogel could also be used as a matrix for co cultures, such as tissue culture, or for example for culturing tumor cells originating from patients biopsies, or from other primary cells, cancer cell derived cell lines, or cancer stem cells derived cell lines. Those cells can be cultured either in 2D or 3D, mono- or co-cultures. In tissue culturing different types of cells are cultured together, like a mini-tissue, which is suitable for example for transplantation in vivo therapy testing. The in vivo like cells cultured are for example in vivo like 2D cells, such as cells for mucous membrane culturing, 3D cells or cell spheroids. 2D cells may be cultured on beads within the hydrogel.

For example human pluripotent stem cells (hPSCs), including human embryonic stem cells (hESCs) and induced pluripotent stem cells (hiPSCs), show great potency in drug research and regenerative medicine. Since the first hESC lines were established in 1998, a lot of research had focused on the development of in vitro culture systems to maintain the pluripotency and to minimize the differentiation of hPSCs. For clinical applications, the cells cannot be in contact with animal-derived components. Therefore, a number of synthetic biomaterials have been produced to replace traditionally used feeder cells and Matrigel as substrata in the hESC and hiPSC cultures. However, many of them are two-dimensional (2D) cell cultures, which do not mimic the in vivo three-dimensional (3D) stem cell niche. The unique feature of the NFC hydrogel-based 3D culture system is that the hPSCs form pluripotent 3D spheroids in the NFC hydrogel and intact 3D spheroids can be recovered from the hydrogel by a cellulase enzyme for downstream applications.

Any article or test plate suitable for cell culturing including single and multi-well plates, such as 6, 12, 96, 384, and 1536 well plates, multiwall culture plates, microtiter plates, high throughput plates, jars, petri dishes, flasks, multi-layered flasks, beakers, plates and dishes, roller bottles, cell culture bottles, paper based supports, slides, such as chambered and multichambered culture slides, tubes, cover slips, bags, membranes, hollow fibers, beads and microcarriers, cups, spinner bottles, perfusion chambers, syringes, bioreactors, and fermenters may be used as a support for the cell culturing and/or for the chemical testing. Typically the NFC hydrogel is either provided onto a support before cells are seeded onto/into the gel, or in another alternative the cells are seeded into the hydrogel and the seeded hydrogel is dispensed onto a support, or yet in another alternative cells are first cultured in a media on a support, the media is removed and the hydrogel is added onto the support thereby encapsulating or covering the cultured cells.

The in vivo like cells are alternatively kept in the NFC hydrogel during the chemical testing or then the in vivo like cells are removed from the NFC hydrogel and the cell clusters are tested in another media, typically in a liquid.

The structure, composition and function of a cell library may vary. A certain composition of a cell library may comprise for example; cells relating to the same internal organ or body part, such as cardiomyocytes, cardiac endothelial cells and cardiac fibroblasts used for testing cardiotoxicity, renal proximal tubule epithelial cells for testing nephrotoxicity or neurons for testing neurotoxicity; cells from different internal organs or body parts, to be used for toxicity testing when it is more unclear which organs the chemical affect; the same type of cells produced in different ways for example from different cell lines, different sources or with different techniques; cells affected with a certain disease such as some kind of cancer; or for example to co-cultures of different cells. The cell library may relate to stem cells, to liver, kidney, cardio, skin or lung related cells.

The cell library as used in the different embodiments of the invention contains two or more, preferably 3, 5, 10, 20, 40, 60, 90, 100, 200, 300, 400 or more different cells, most preferably 3, 6, 12, 24, 48 or 96 different cells in a 6, 12, 24 or 96 test plate, such as 96 well plate.

Removal of NFC Hydrogel

The removal of cellulose nanofibers hydrogel can be carried out by physical, mechanical or chemical removing or any combination thereof. The preferred method is chemical removing, more preferably treating the plant-derived NFC enzymatically with a cellulase for a time sufficient to at least partly release the cells. Typically the cellulase is a cellulolytic enzyme mixture, optionally comprising hemicellulases, a commercial cellulase, a partially purified cellulase, or a purified cellulase. The removal of NFC hydrogel is done for example with enzymes mixtures comprising all necessary enzymes for partial or total degradation of cellulose molecules as well as other wood derived components in it, such as hemicelluloses.

Proper enzymes are for example designed enzyme mixtures for the NFC in question and commercially available cellulase-hemicellulase preparations. The composition of the mixture can vary depending on the chemical composition of the raw material used for production of that NFC. For example when birch pulp is used for production of NFC the mixture includes at least intact endo- and exocellulases or parts of them, endo-xylanases and beta-D-glycosidases and beta-D-xylosidases. For hydrolysis of softwood derived NFC the mixture needs to be supplemented at least with endo-mannanases and beta-D-mannosidases. The benefit of designed mixtures pooled from purified enzyme components is that they do not contain additional proteins or other unwanted components, such as side activities, debris from the cultivation organism or residues from culture broth, which is often the case for commercial enzyme preparations. Especially harmful is, if the preparation contains proteases, which might attack on the cultured cell surfaces. Commercial enzyme mixtures designated for total hydrolysis of plant based materials can also be used in hydrolysis of NFC, but more preferably after at least crude purification step, such as gel filtration or dialysis. Regardless of the enzyme preparation, either a designed or commercial mixture, the components are selected so that they can optimally hydrolyse NFC for example in respect of pH, temperature and ionic strength.

Commercial preparations are available, which are acting either in the acidic pH values (pH 3.5-5) or in higher pH values (pH 6-8) and at temperatures from room temperature up to 60-80 degrees centigrade Very often the cells are grown at 37 degrees centigrade, which is an optimal temperature for the most cellulases and hemicellulases.

Removal of the NFC hydrogel may be conducted as disclosed e.g. in WO 2012/056109 or WO2014/049204. Typically there is no need to remove the degradation products such as glucose. Also the enzyme may remain in the system, or it may be inactivated or removed. The degradation products of NFC hydrogel do not decrease the pH of the system to a level that would harm the cells present in the system. This is not the case for some other enzymatically degradable cell culture matrices, such as hyaluronic acid or alginate based matrices.

According to one embodiment the in vivo like cells are separated from the plant-derived NFC by physical removal of the NFC hydrogel for example by diluting with an aqueous or non-aqueous liquid; and then removing the cellulose nanofibers by sedimentation facilitated e.g. by centrifugation, and decantation.

According to one embodiment removing the plant-derived NFC takes place at least once at any stage after obtaining in vivo like cells cultured in a first plant-derived NFC and before at least one last detection of the impact of the test chemical on the in vivo like cells. The NFC hydrogel is typically removed after exposing the in vivo like cells to a test chemical, but before incubating the exposed in vivo like cells or before detection of the impact of the test chemical on the in vivo like cells. Exposing the in vivo like cells to a test chemical may take place within the first hydrogel or alternatively within another hydrogel having the same or different properties than the first hydrogel. The first NFC hydrogel is typically removed after obtaining in vivo like cells but before exposing the in vivo like cells to a test chemical. In that case exposing the in vivo like cells to a test chemical is optionally taking place within another plant-derived NFC hydrogel. Thus the properties of this further NFC hydrogel may be different from the properties of the first hydrogel e.g. having different stiffness of NFC hydrogel, NFC concentration, shear-zero viscosity of NFC hydrogel, NFC hydrogel charge, and/or transparency.

The further NFC hydrogel can optionally also be removed in order to perform some further detecting of the impact of the test chemical on the in vivo like cells. In this case the method further comprises removing the plant-derived NFC hydrogel between obtaining in vivo like cells and exposing the in vivo like cells to a test chemical; and thereto removing the plant-derived NFC hydrogel at least once more at any stage after exposing the in vivo like cells to a test chemical and before at least one last detection the impact of the test chemical on the in vivo like cells.

Test Chemical

The test chemicals used for the chemical testing can be a variety of materials, substances or compounds whose impact on in vivo like cells is to be tested. Test chemical(s) may be chemical substances; organic or inorganic chemical compounds; or chemical mixtures containing more than one chemical substance or ingredient and not having a fixed composition; or biological agents or fragments thereof such as pathogens, antigens, epitopes, or antibodies; or any combinations thereof. Typically the test chemical is selected from the group consisting of drugs; drug candidates; pro-drugs; pro-drug candidates; nanoparticles; cell regulatory agents, such as differentiating agents; food or food additives, such as artificial sweeteners; household products, such as cleaning products; industrial chemicals, packing materials; air freshener, plant growth regulatory agents; environmental toxins; pesticides, such as insecticides, herbicides or fungicides; personal care products, such as cosmetics; or their chemical ingredients. The test chemicals can be tested in an undiluted or diluted form. The chemical testing may be for example for genotoxicity, for carcinogenicity, for neurotoxicity, for mitochondrial toxicity, for cardiotoxicity, for hepatotoxicity, for hematopoietic toxicity, for nephrotoxicity, for safety testing; for causing reproductive toxicity, for causing skin or eye irritation.

The structure, composition and function of a test chemical library may vary. A certain composition of a test chemical library may comprise for example; chemicals thought to have a certain effect, i.e. thought to affect cells in the same way, such as chemicals used for toxicity tests for endocrine disruption; drugs tested for toxicity or repeated-dose toxicity; chemicals tested to detect compounds that cause Drug-Induced Liver injury in Humans; drugs used for cardiotoxicity tests using for example cardiomyocytes, cardiac endothelial cells and/or cardiac fibroblasts; drugs tested for neurotoxicity or nephrotoxity. The test chemical library may also relate for example to drugs used to treat a certain disease such as cancer. Further the test chemical library may comprise the same chemicals in different concentrations. The concentrations of the chemicals can be chosen based on their Cmax values, as well as their solubility properties.

Further a composition of a test chemical library may relate for example to drug-induced liver injury (DILI) positive chemicals, preferably one or more chemical chosen from Benzbromarone, Clozapine, Diclofenac, Flurbiprofen, Mefenamic acid, Mebendazole, Phenacetin, Phenylbutazone, Quinine and Trazodone HCl; DILI negative chemicals, preferably one or more chemical chosen from Aspirin, Buspirone, Dexamethasone, Dextromethorphan HBr, Fluoxetine, Lidocaine, Miconazole, Prednisone, Propranolol and Warfarin; or compounds not identified correctly as DILI positive in short-term sandwich cultures of primary human hepatocytes, preferably one or more chemical chosen from Acetazolamide, Betahistine 2HCl, Captopril 24, Chloramphenicol palmitate, Ciprofloxacin HCl, Clomiphene citrate, Clomipramine, Cyclophosphamide, Cyproterone acetate, Danazol, Dapsone, Estrone, Hydroxyurea, Imipramine HCl, Isoniazid, Maleic acid, Methimazole, Nifedipine, Norgestrel, Nortriptyline HCl, Phentolamine mesylate, Piroxicam, Progesterone and Pyrazinamide, Tamoxifen.

Examples of test chemical libraries comprises a library for finding novel uses for known drugs, like FDA-Approved Drug Library; or a library of natural products; or a Library of Pharmacologically Active Compounds (LOPAC1280), or NIH Clinical Collection (NIHCC); or NCI DTP; or Microsource Spectrum; or toxicity libraries, like Enzo toxicity libraries; or ICCB Known Bioactives Library.

The test chemical library as used in the different embodiments of the invention contains two or more, preferably 3, 5, 10, 20, 40, 60, 90, 100, 200, 300, 400 or more different test chemicals, most preferably 3, 6, 12, 24, 48 or 96 different test chemicals in a 6, 12, 24 or 96 test plate, such as 96 well plate. Preferably the test chemical library comprises or contains two or more DILI negative chemicals, two or more DILI positive chemicals and/or two or more chemicals with known susceptibility to DILI such as compounds not identified correctly as DILI positive in short-term sandwich cultures, more preferably 3, 6, 12, 24, 48 or 96 different test chemicals in a 6, 12, 24 or 96 test plate, most preferably a 96 well plate.

Detecting

Aspects of the invention further relates to providing a process where plant-based NFC hydrogel is used in chemical testing. The process comprises culturing in vivo like cells, for example tissues, cell spheroids or alike on or in a NFC hydrogel and the in vivo like cells are contacted with a chemical, for example drug candidate or pro-drug candidate to be tested. Incubating the in vivo like cells contacted with the chemical allows the chemical to influence on the cells allowing the in vivo like cells to absorb, bind to, or otherwise react (or fail to react) with the chemical. A typical incubating time for chemical toxicity testing is 7 to 21 days, preferably around 14 days. Long term toxicity testing can be continued for between 1 and 12 months or even longer. Incubating comprises maintaining the in vivo like cells under desired conditions either while being exposed to the test chemical i.e. in the presence of the test chemical, or after being exposed to the test chemical but in the absence thereof. After incubating, measurements are done either manually or by a machine.

The detecting refers to qualitative or quantitative determination of the impact of a test chemical on the in vivo like cells, or to a combination of qualitative and quantitative determinations. The detection of the impact of the test chemical on the in vivo like cells may for example comprise qualitative detecting, quantitative detecting, or any combinations thereof, typically detecting involves a plurality of detections using different techniques eventually making use of miniaturized and enhanced detection technology. The measuring is performed with different tests known in the art such as tests based on chromatographic detection systems, optical detection systems and any combinations thereof. The chromatographic detection system is typically based on chromatography such as GC, HPLC, affinity, displacement, ion-exchange, size exclusion, gel-filtration, fast protein liquid, paper, or thin-layer chromatography; or on electrochromatography such as gel-electrophoresis, 2D gel-electrophoresis, or isoelectric focusing. The optical detection system is typically based on one or more of visual examination; spectroscopy such as nuclear magnetic resonance (NMR), Raman, IR, UV, visible light, fluorescence, mass spectrometry (MS); microscopy such as optical microscopy (phase contrast, reverse phase contrast, confocal, fluorescence) or electron microscopy (TEM, SEM) or scanning-probe microscopy (AFM); photometry; laser or flow-cytometry, optionally using high content screening and/or isotope labelling. Microscopy is the science of using microscopes to see things that are too small to see with the unaided eye. Spectroscopy is the science of using spectra to analyze electromagnetic radiation. The detection of the impact of the test chemical on the in vivo like cells may involve transplantation of the exposed in vivo like cells into test animals, optionally followed by preparation and detecting of histological samples. High-throughput screening (HTS) is a method for scientific experimentation especially used in drug discovery and relevant to the fields of biology and chemistry. Using robotics, data processing and control software, liquid handling devices, and sensitive detectors, High-throughput screening allows a researcher to quickly conduct millions of chemical, genetic, or pharmacological tests. Through this process one can rapidly identify active compounds, antibodies, or genes that modulate a particular biomolecular pathway. The results of these experiments provide starting points for drug design and for understanding the interaction or role of a particular biochemical process in biology.

Typically the effects on the features of the cells or the chemical tested are measured, such as the viability of the cells; if the drug is metabolized or if the pro-drug candidate is changed into the active drug form. Cell proliferation and viability is typically tested and monitored by AlamarBlue® assay. Metabolite(s) are typically tested by MS or HPLC. The detecting or testing may also comprise MTT assays, LDH assays and propidium iodide tests as well as imaging, isolating proteins, using test animals, tests relating to neurotoxicity and immunologic reactions.

A system according to an embodiment of the invention typically comprises NFC on a support such as 96 well plate, in vivo like cells, chemical libraries such as libraries of different drugs or pro-drugs, and reading apparatus. The system could be e.g. a kit for conducting the process of the invention comprising NFC hydrogel or material for producing it, a support such as a test plate for example a 6, 12, 24 or 96 well plate and instructions for cell selection and for chemical toxicity or safety testing or drug screening. The kit is typically used for toxicity testing, safety testing, drug testing or pro-drug testing. According to aspects of the invention on hand a kit for chemical testing comprises plant-derived NFC hydrogel; instructions for carrying out the method as defined in the claims; and at least one library chosen from a cell library and a test chemical library. Typically the hydrogel is ready for use but alternatively the NFC is provided for the hydrogel. Different kinds of cells may require NFC hydrogel of different stiffness or concentration. The kit further typically comprises a test chemical library ready for use within the kit and already added to the NFC hydrogel or a cell library added to the hydrogel. Adding the cell library comprises either adding in vivo like cells obtained by culturing cells in a plant-derived NFC hydrogel or seeding cells to be cultured to the NFC hydrogel, i.e. in or on the NFC hydrogel. If the added cell library comprises in vivo like cells, the instructions for carrying out the method as defined in the claims does not need to comprise instructions for culturing cells to obtain such in vivo like cells. Typically the instructions for carrying out the method comprises instructions to one or more of culturing cells on or in a first plant-derived nanofibrillar cellulose (NFC) hydrogel to obtain in vivo like cells; exposing the in vivo like cells to a test chemical; within said first plant-derived NFC hydrogel or another plant-derived NFC hydrogel; incubating the exposed in vivo like cells; detecting, during or after the incubating, the impact of a test chemical on the in vivo like cells by at least one detection; and removing the plant-derived NFC hydrogel at least once at any stage after obtaining in vivo like cells and before at least one detection of the impact of a test chemical on the in vivo like cells. In the kit the NFC hydrogel is typically provided in a form of an aqueous stock comprising from 0.5 to 25 w % of NFC, such as 1-5 w %, or 1.2-5 w % and the plant-derived NFC hydrogel may be on a support, preferably a 6, 12, 24 or 96 well plate. The support may also be a vial, a tube or a bottle, especially in case of the aqueous stock having higher concentration. The aqueous stock may be prepared into working concentration by applying high shearing forces e.g. using a blender, a fluidizer, a disperser or a homogenizer so that a homogeneous dispersion is formed. The kit may further comprise a vial of cellulase for removal of the hydrogel. Typically a kit comprises a cell culture plate to be used for three dimensional cell culture, which can form multi-cellular clusters (spheroids), just by seeding cells like on monolayer cell culture plates. Preferably the plate has a clear bottom film.

According to further embodiments the process, method and kits are used for anti-cancer drug screening, testing neuron cells for Alzheimer drug testing, testing pro-drug formed in liver on liver cells, testing pro-drug targeting tumor cells on tumor cells. The process, method and kit can be used in low, medium and high throughput screening as well as in extended toxicity screening. The embodiments of the invention can also be used for safety testing of nanoparticles, testing proteins and micro vesicles.

The following examples are illustrative of embodiments of the present invention, as described above, and they are not meant to limit the invention in any way. Thus, any of the embodiments and aspects discussed in this specification can be implemented with respect to a method, kit, reagent or composition. The invention is illustrated also with reference to the figures.

EXAMPLES

The following hydrogel materials were used in the chemical testing experiments:

Nanofibrillar cellulose (NFC) hydrogel was obtained from UPM Kymmene Corporation, Finland. The nanofibers were isolated from bleached birch pulp via a controlled homogenization process using an industrial fluidizer. The raw material was aseptically collected from a UPM pulp mill and thoroughly purified using ion-exchanging and washing prior to homogenization with sterilized machinery. Thus, the microbial purity was maintained through the whole production process. Purified pulp fibers were diluted with sterilized, ultra high quality water before the fibrillation. The NFC concentration of the resulting hydrogel is typically 1.7 wt-%. Prior to cell culturing the NFC hydrogels were autoclaved (121° C. 20 min).

Rheological Analysis of the NFC Hydrogel

NFC hydrogel stock was diluted with RPMI-1640 basal medium into three concentrations: 0.5, 0.75 and 1.0%. Rheological measurements of the NFC hydrogels were carried out with a stress controlled rotational rheometer (ARG2, TA instruments) equipped with four-bladed vane geometry. The diameters of the cylindrical sample cup and the vane were 30 mm and 28 mm, respectively, and the length was 42 mm. The storage modulus (G') and loss modulus (G") of GrowDex hydrogels was measured using a gradually increasing stress of 0.01-100 Pa. The steady state viscosity of the hydrogels is measured using a gradually increasing shear stress of 0.001-1000 Pa. After loading the samples to the rheometer they are allowed to rest for 5 min before the measurement is started, room temperature. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of 1000 s−1 is exceeded. The method is used for determining zero-shear viscosity and yield stress. The viscosity properties of the hydrogels were also determined with the frequency sweep in dynamic oscillation mode of the rheometer (strain 1% and 10%, frequency 0.1-100, temperature 25° C.). The stress sweep was measured in a shear stress range of 0.001-100 Pa at the frequency 0.1 Hz, at 25° C., pH 7.

Rheological Features of the NFC Hydrogel

NFC hydrogels at different concentrations prepared by pipetting in the same way as preparing hydrogel-cell mixture were measured with rotational rheometer. FIG. 1 shows rheological properties of NFC hydrogel (GrowDex) mixed with RPMI-1640 growth medium. Flow curves of measured hydrogels are presented as a function of shear stress of (A) storage modulus (G') and (B) loss modulus (G"). Measurements were made with 0.5%, 0.75% and 1.0% hydrogel concentrations. For comparison there are also data from 0.5% NFC hydrogel diluted with water. These measurements indicate homogenous viscoelastic properties of the hydrogels. There are clear differences between investigated NFC concentrations mixed with RPMI-1640 basal medium regarding storage modulus (G') and loss modulus (G"). The measurements revealed typical behavior of a NFC hydrogel, where the storage modulus (G') is much higher than the loss modulus (G") and basically independent of a given stress.

Storage modulus shows stiffness of the hydrogels being around 25 Pa for 0.5% NFC hydrogel, 70 Pa for 0.75% hydrogel and 200 Pa for 1.0% hydrogel, respectively. Thus a twofold increase in hydrogel concentration resulted in an 8-fold increase in material stiffness.

Comparative Example 1

Comparison of Plant-Derived Nanofibrillar Cellulose Hydrogel and Hyaluronan-Gelatin Based Hydrogel for Obtaining In Vivo Like Cells by Cell Culture and Releasing Said in Vivo Like Cells Cell Maintenance The hESC line WA07 and iPSC line iPS(IMR90)-4 were purchased from WiCell. Stem cells were maintained on Matrigel-coated 6-well plates in mTeSR™1 medium (05850, STEMCELL™ Technologies) which was changed daily. Matrigel coatings were produced by incubating Matrigel (Matrigel basement membrane matrix growth factor reduced, BD Biociences, 356230) dilution (0.5 mg per one 6-well plate) in wells for one hour at room temperature. Stem cells were passaged at a ratio of 1:6 every four days after removal of differentiated cells. Versene 1:5000 (Invitrogen, 15040033) was used to detach the stem cell colonies. The human hepatocellular carcinoma HepG2 cells from ATCC (HB-8065) were maintained in 75 $cm^7$ cell culture flasks in DMEM with high glucose, GlutaMAX™, and pyruvate (Gibco, 31966) supplemented with 10% fetal bovine serum, 100 U/ml penicillin, and 100 ug/ml streptomycin. The medium was renewed three times per week. HepG2 cells were passaged at a ratio of 1:6 every 3-4 days using TrypLE™ Express (Gibco, 12604-021). All cell cultures were maintained at 37° C. in a humid atmosphere with 5% $CO_2$.

2D and 3D cell cultures. All the cells were cultured in standard 2D culture and in 3D culture using either the NFC hydrogel (GrowDex™. UPM-Kymmene, Espoo, Finland) or a commercial ExtraCel™ (EC) hydrogel, a hyaluronan-gelatin based hydrogel (Glycosan biosystems, GS208). 2D cultures were performed in 35 mm glass bottom dishes (MatTek Corporation, P35G-1.510-C). For 2D cultures, stem cells were passaged at a ratio of 1:6 on Matrigel coating as described above. The seeding density for HepG2 cells was 40 000 cells/$cm^2$. 3D cultures were performed in 8-well Lab-Tek® Chamber Slide™ systems (Nunc, 177445). 3D cultures of stem cells and HepG2 cells in the NFC hydrogel were performed as follows. Detached stem cell colonies or HepG2 cells were mixed with 0.5 w.t % or 1.0 wt-% NFC hydrogel, respectively. The EC hydrogel formation and cell encapsulation were performed according to the manufacturer's protocol. An equal medium volume to hydrogel volume was added on top of the NFC and EC hydrogels. The stem cell colony density was five times higher than that in 2D cultures, and the HepG2 cell density in the hydrogels was 1×10$^6$ cells/ml. The media were renewed daily for all the stem cell cultures and every 3-4 days for all the HepG2 cell cultures. Both stem cells and HepG2 cells were fixed with 4% paraformaldehyde (PFA) for 10 min after four days in 2D cultures, 15 min (3D HepG2 spheroids), or 30 min (3D stem cell spheroids) after two, five, and eight days in 3D cultures for further analyses.

To count cell number in hPSC spheroids, spheroids were dissociated by Trypsin, and then the single cells were counted by trypan blue exclusion.

Enzymatic Removal of the Hydrogels

The NFC hydrogel was degraded with a cellulase enzyme (VTT, Turku, Finland) and the EC hydrogel with 1× collagenase/hyaluronidase (StemCell Technologies, 07912). The cellulase treatment was performed by adding 300 µg of cellulase per 1 mg NFC and incubating for 24 hours at 38° C. on a shaker. Spheroids were subsequently washed with 1×DPBS(−) to remove cellulase enzyme. The EC hydrogel was removed according to the manufacturer's instructions. However, intact spheroids could not be recovered from the EC hydrogel; instead, enzymatic digestion resulted in single cells.

Flow Cytometry

3D WA07 spheroids were first recovered from the NFC hydrogel with cellulase enzyme as described above. Next, the spheroids were disintegrated to single cells with a Cell Dissociation Buffer (Gibco, 13151-014) followed by Accutase (Merck Millipore, SCR005). The cells were first incubated with anti-SSEA-4 (Developmental Studies Hybridoma Bank, MC-813-70, 1:400 in 2% FBS) on ice for 60 min. After washing, the cells were incubated with goat anti-mouse IgG (H+L), conjugated with APC (SouthernBiotech, 1031-11S, 1:300 in 2% FBS) on ice for 40 min. The negative control sample was stained with only the secondary antibody. The cells were analyzed on a BD LSR II flow cytometer (633 nm laser, 660/20 BP filter detector) using BD FACSDiva software. The overlay histograms were created with Flowlogic software.

To analyze the cells inside the spheroids, histological paraffin sections were generated. After fixed in 4% PFA, the spheroids were embedded in HistoGel (Thermo Scientific) and thereafter in paraffin. Five-micrometer thick sections were cut at the Finnish Center for Laboratory Animal Pathology and used for immunohistochemistry.

Figure 2A:
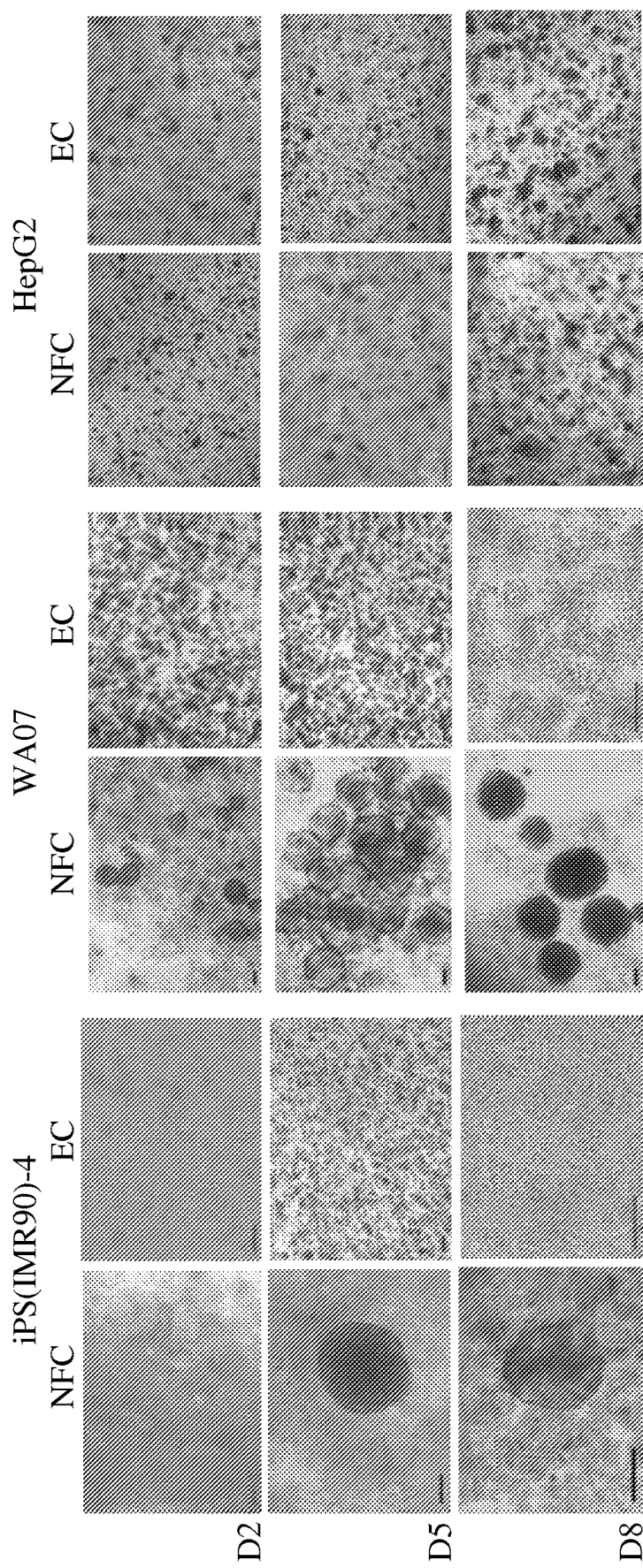
FIG. 2 a-d The hiPSCs iPS(IMR90)-4, hESCs WA07, and human hepatoma HepG2 cells cultured in 3D hydrogels.
Figure 2D:
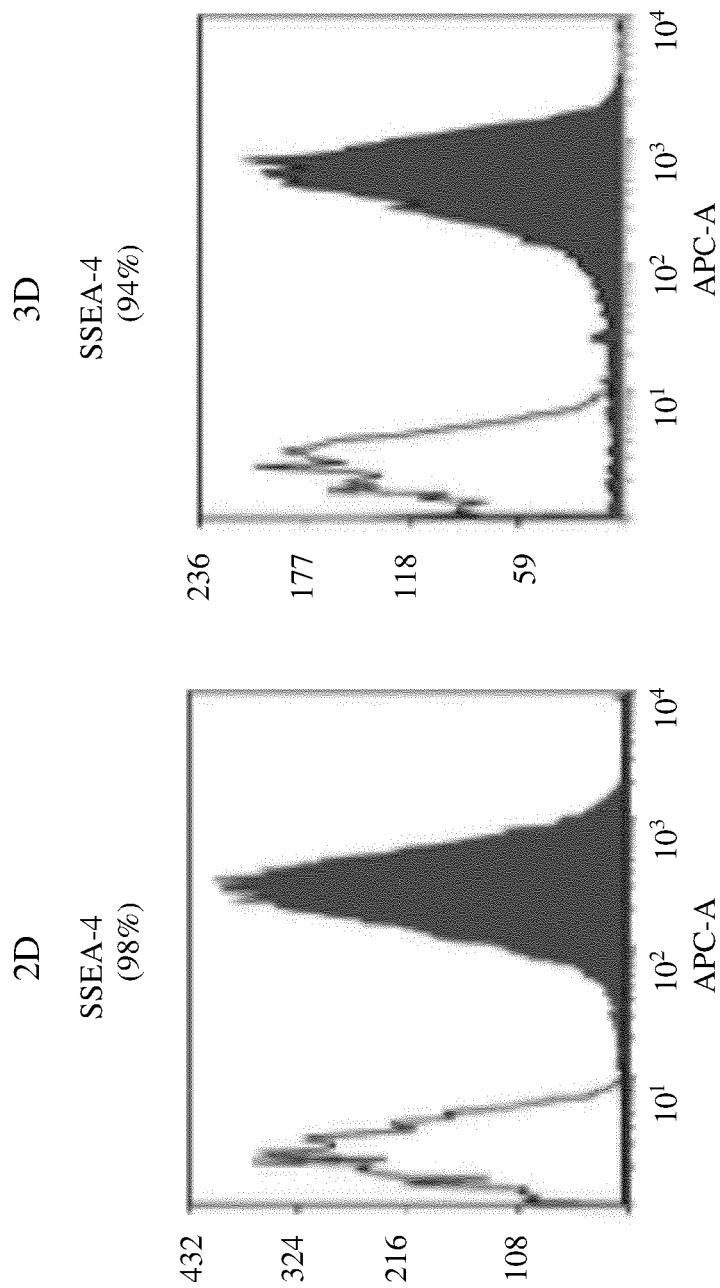

The Phenotypic Features of the Cells in 2D and 3D Cultures hPSCs and HepG2 cells were cultured in the NFC hydrogel and in the ExtraCel™ hydrogel, a hyaluronan-gelatin-based hydrogel. FIG. 2 shows the pluripotency marker OCT4 is expressed in WA07 cells cultured in standard 2D culture system (b) and in the NFC hydrogel for 7 days (5 µm paraffin section) (c). FIG. 2 (d) shows a flow cytometry analysis of pluripotency marker SSEA-4 in WA07 cells after being cultured in 2D and in 3D NFC hydrogel for 7 days. The scale bars are 100 rm. The phase contrast microscopy images reveal that both iPS (IMR90)-4 and WA07 cells form round 3D spheroids with diameters between 100 µm to 350 µm in the NFC hydrogel culture, but not in the ExtraCel™ hydrogel (FIG. 2a). The average cell number in each WA07 spheroid is 3730±2800. The cell viability estimated by trypan blue exclusion is over 97%. The pluripotent markers of hPSCs were studied by immunofluorescence and flow cytometry. WA07 cells expressed the pluripotent markers OCT4 and SSEA-4 at similar levels in both the standard 2D culture and 3D NFC hydrogel culture (FIG. 2b-d). HepG2 cells formed 3D spheroids with diameters between 200 m to 800 µm in both studied hydrogels.

The formation of 3D spheroids of hPSCs and HepG2 cells in the NFC hydrogel was shown and also that cells in the spheroids are more round than those in 2D cultures, and they develop tight cell-cell interaction and microvilli-coated membranes as seen in 2D cultures. Furthermore, the cells cultured in the NFC hydrogel produced a greater amount of extracellular matrix than those in 2D culture. Studying the cell morphology and spatial organization helps better understand and regulate the cell behavior for use in chemical testing, including cancer research, drug research, and tissue engineering.

Among the handful 3D culture systems for hPSCs, the NFC hydrogel-based 3D culture described above has a unique feature. It enables the recovery of intact 3D cell spheroids, and thus it is compatible with various downstream applications and analyses. In comparison, intact spheroids cannot be recovered from the ExtraCel™ hydrogel. Evidence from cell counting indicated that the hPSC spheroids are fully packed with cells.

Example 1

Formation of 3D Stem Cell Spheroids in NFC Hydrogel

Cells used for this study were human embryonic stem cell line WA07 with normal karyotype and blood type B (WiCell). Cells were cultured in aseptic conditions without antibiotics and incubated in HERACell® 150 CO2 incubator (Kendro laboratory) at 37° C. in 5% CO2.

Cells were thawed and seeded to the 2D conditions on Matrigel (BD Biosciences®; 356230) coated 6-well plate (Sarstedt; 83.1839). Matrigel coating was made at room temperature by adding cold DMEM/F-12 medium (Gibco®; 31330) to the cold Matrigel solution and incubating for one hour at room temperature. A feeder-free and serum-free stem cell culture medium mTeSR1™ basal medium (Stem Cell Technologies; 05851) supplemented with 5× mTeSR™1 (Stem Cell Technologies; 05852) was changed daily. Approximately on day four cells when the cell confluency was 60-80% they were passaged into a new Matrigel coated 6-well plate using a splitting ratio of 1:4 to 1:6. The detaching agent used was EDTA (Versene® 1:5000, Gibco®; 15040-033) and the differentiated cells were removed by pipette before splitting. Passaging was performed at least once on 2D culture conditions to make sure the used cells were viable and showed normal growth. The first stem cells characterized by IF were from passage 38.

After cultured long enough in 2D conditions in order to get required amount of cells the stem cells were transferred from 2D into 3D culture condition to form 3D stem cell spheroids. The detached cells were suspended with 0.5% NFC hydrogel and cultured into 96-well plate (Greiner bio-one; 655090). The amount of NFC hydrogel used was 300 µl/cm2 and the cell amount in the hydrogel was five times higher than used in 2D culturing. The same volume of mTeSR1 medium was added on top of cell-hydrogel mixture. 0.5% NFC hydrogel was prepared by diluting 1.47% NFC stock (GrowDex® UPM-Kymmene Corporation; 1544) in mTeSR1 medium. Medium from the top of the hydrogel was changed daily using double concentrated mTeSR1 since only half of the total well volume was changed in NFC culturing. This culture condition was kept for six days. After six days NFC hydrogel was removed using cellulase, an enzyme mixture for birch cellulose (VTT). Cellulase was incubated with spheroid-hydrogel mixture (300 µg cellulase/mg of NFC) for 24 hours at 37° C. At this time point the pluripotency of the stem cells were analyzed with flow cytometry, and cell viability together with the average cell number in the spheroids was counted with Trypan Blue exclusion, or the cells were used for further differentiation. Growth and morphology of the spheroids were monitored with phase contrast microscopy regularly during the experiments.

Cell Morphology and Viability

Figure 3:
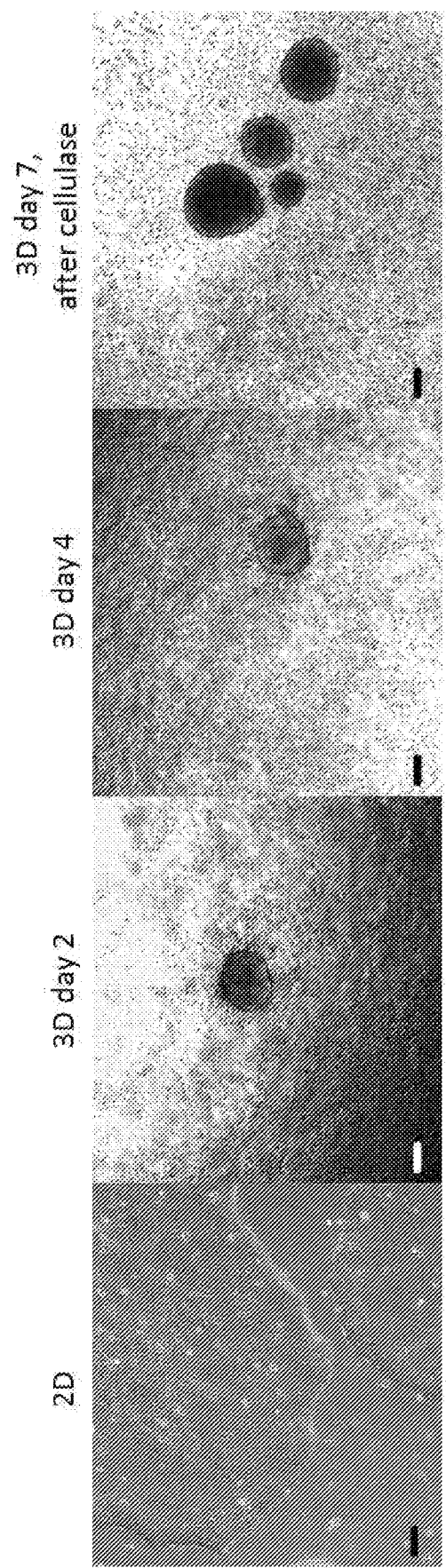
FIG. 3. Phase contrast microscope images from two-dimensional and from 3D pluripotent stem cell culturing.

At the 2D culturing stage cells showed good viability based on the growth seen by phase-contrast microscope and the colonies presented typical pluripotent morphology. After seeding the cells into 0.5% NFC hydrogel cells formed spheroids with diameters between 100-300 m. FIG. 3 shows phase contrast microscope images from two-dimensional pluripotent stem cell culturing and from three-dimensional pluripotent stem cell culturing 2, 4, 7 days after three-dimensional culture starting. The scale bars are 100 µm. The phase-contrast images showed cell density and spheroids diameter increased during 3D culturing stages and there were also forming of new spheroids. After the 3D culturing cells in the spheroids exhibited good viability with Trypan blue exclusion test, 93.4% of living cells per well and 97.1%±3.1% of living cells per spheroid. The average amount of the cells was 183000 per well, 100 µl of NFC, and 3729 2845 cells per spheroid. The formed spheroids presented round morphology with clear borders.

Protein Expression Analyses

Figure 4:
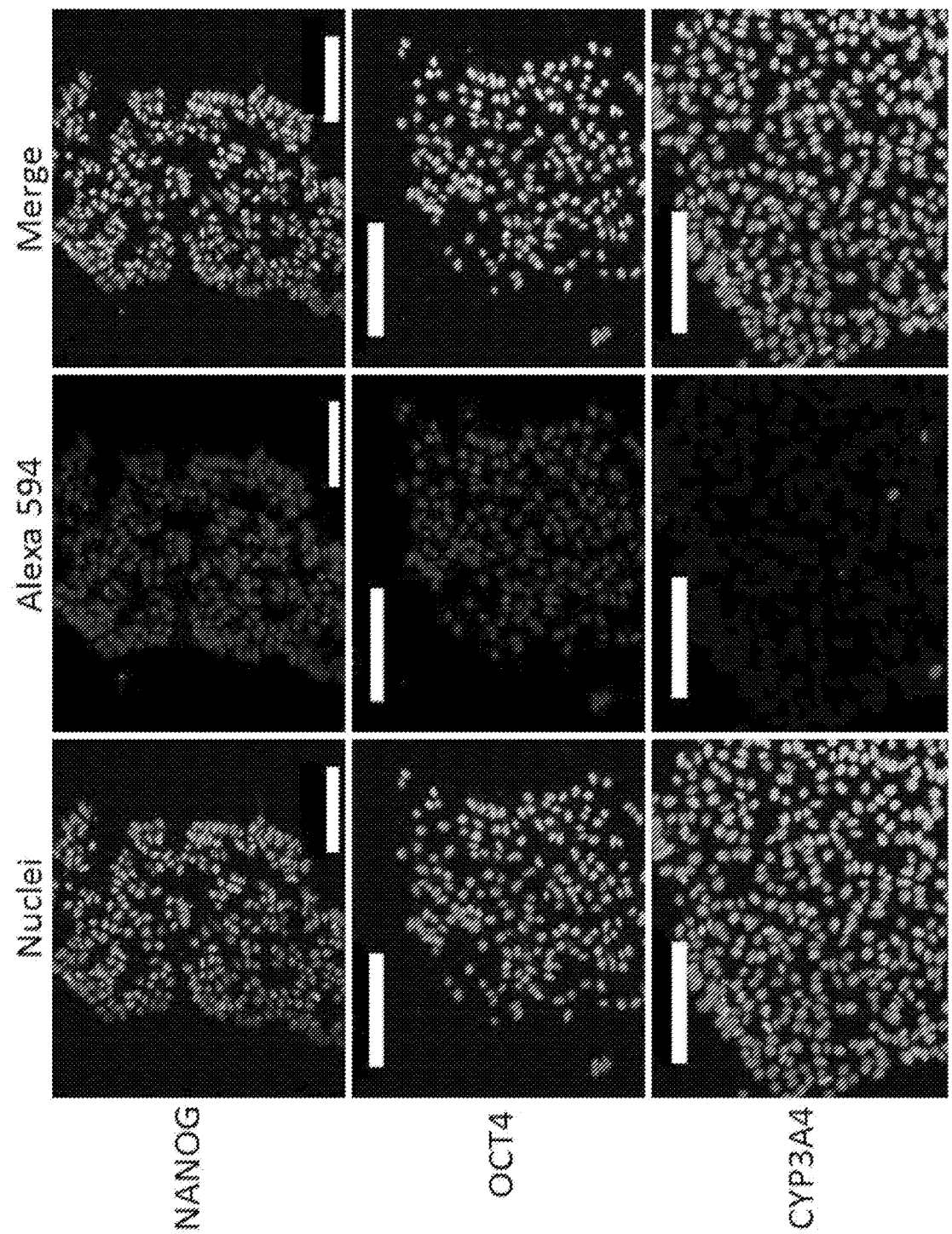
FIG. 4. Immunofluorescence images taken after 2D plurinpotent stem cell culturing stage.
Figure 5:
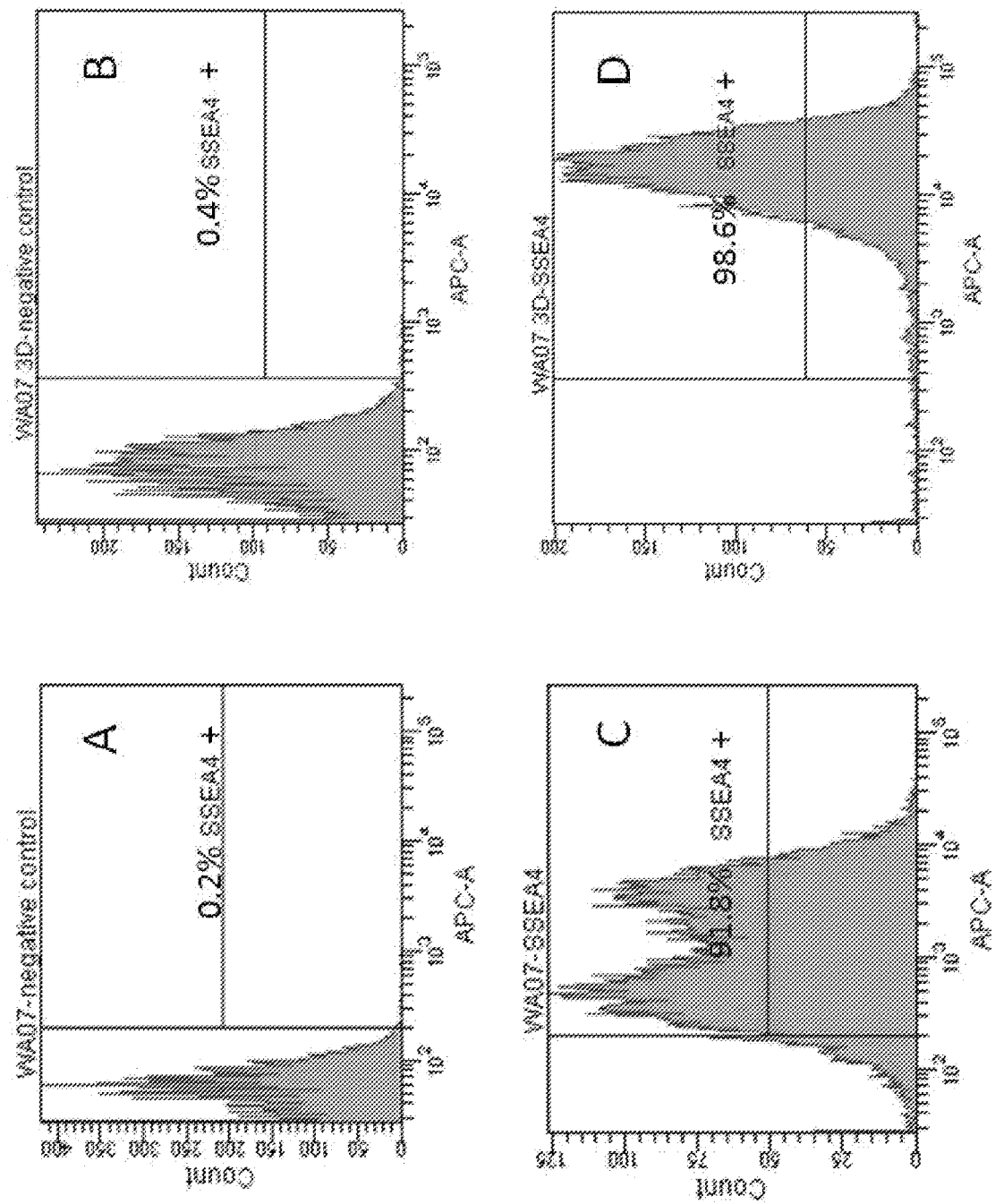
FIG. 5. Pluripotency marker SSEA4 analysis for pluripotent human embryotic stem cell line WA07 after 2D (A, C) and 3D (B, D) culturing by flow cytometry.

FIG. 4 shows immunofluorescence images taken after two-dimensional pluripotent stem cell culturing stage. NANOG and OCT4 are pluripotency markers and CYP3A4 is hepatocyte marker. The scale bars are 100 µm. The cells cultured in 2D conditions had strong expression of pluripotent stem cell markers NANOG and OCT4, but hepatocyte marker CYP3A4 was negative shown by immunofluorescence. FIG. 5 shows pluripotency marker SSEA4 analysis for pluripotent human embryotic stem cell line WA07 after two-dimensional (2D) (A, C) and three-dimensional (3D) (B, D) culturing by flow cytometry. Over 91% of the 2D cultured cells and nearly 99% of the 3D cultured cells presented pluripotent marker SSEA4 positivity with flow cytometry studies.

Example 2

Studying the Impact of Activin a on In Vivo Like Cells Obtained by Culturing in Plant-Derived NFC Hydrogel In short stem cells were cultured in NFC hydrogel to obtain 3D spheroids, which were released from the NFC hydrogel by enzymatic digestion. Then the 3D spheroids were washed and seeded into another NFC hydrogel, and a test chemical, here growth factor Activin A, was added and the 3D spheroid cultures were incubated. After incubation, the impact of the test chemical on spheroid morphology was detected before removing the second NFC hydrogel, while other detections were conducted after removing the NFC hydrogel.

Exposing 3D Stem Cell Spheroids to Test Chemical Growth Factor Activin a for Inducing Formation of Definitive Endoderms After growing stem cell spheroids and removing them from NFC hydrogel according to Example 1, spheroids were first washed once with RPMI-1640 basal medium (Table 1) supplemented with GlutaMax™ (Table 2). Next spheroids were resuspended with 3 different NFC hydrogel concentrations: 0.5%, 0.75% and 1%. To avoid mechanical disturbance the spheroids were not transferred into new plate and NFC hydrogel was added directly to the previous wells. NFC hydrogel was prepared by mixing NFC stock and differentiation medium M1. Differentiation medium (M1) consisted of RPMI-1640 basal medium supplemented with GlutaMax™, serum substitute B27 and growth factor Activin A (Table 2). The same amount of M1 was also put on top of hydrogel mixture. Double concentrated M1 medium was renewed daily during the experiment. Half of the cells were differentiated for six days, half for nine days before removing NFC hydrogel with cellulase similarly as earlier. On day seven after definitive endoderm (DE) induction the protein expression in DE cells were analyzed by immunofluorescence (IF) and immunohistochemistry (IHC), and viability was analyzed by live/dead cell staining. On day ten the differentiated cells were analyzed by IF. In the second experiment DE spheroids on day six were also analyzed by FACS. The later DE induction in the second experiment was performed with 0.5% NFC for six days based on the results obtained from the first experiment of the study (presented hereinafter).

TABLE 1

Composition of differentiation medium M1 used in stem cell spheroid differentiation into definitive endoderm.

| Medium M1 |
| --- |
| RPMI-1640 Gibco ® 31870-025 |
| GlutaMax 1% Gibco ® 35050-087 |
| B27 ® 1% Gibco ® 17504-044 |
| Activin-A 100 ng/ml PeproTech 20-14E |

Example 3

Studying the Impact of a Combination of Differentiating Agents on In Vivo Like Cells Obtained by Culturing in Plant-Derived NFC Hydrogel Another experiment started with new thawed WA07 cells. The cells were passaged twice on 2D environment and then grown to stem cell spheroids as described in Example 1. After cellulase treatment spheroids were differentiated into DE cells similarly to the previous experiment, this time only with 0.5% NFC hydrogel concentration and for six days. After releasing cells from NFC with cellulase, the experiment continued by the differentiation of DE cells into hepatic progenitor (HP) cells in the same 96 well plate. NFC hydrogel concentrations tested at this differentiation step were 0.5%, 0.75%, and 1.0%. NFC dilutions were made by diluting NFC stock with M2 medium. Differentiation medium (M2) consists of HBM™ basal medium supplemented with suitable HCM™ SingleQuots (Table 2), BMP2, BMP4 and FGF4 (Table 3). Double concentrated M2 medium was renewed daily during this part of the experiment. Spheroids were differentiated for four days and after that NFC hydrogel was removed with cellulase (300 µg/mg of NFC) similarly as before. HP cell characterization was performed by IF, FACS and IHC.

TABLE 2

HCM™ SingleQuots and concentrations used for M2 medium.

| BSA-FAF 2.00% |
| --- |
| Ascorbic Acid 0.10% |
| Hydrocortisone 0.10% |
| Transferrin 0.10% |
| Insulin 0.10% |

TABLE 3

Composition of differentiation medium M2 used in DE
cell spheroid differentiation into HP cells.

Medium M2
HBM + HCM Lonza cc-3199 and cc-4182
FGF-4 5 ng/ml PeproTech 100-31
BMP-2 10 ng/ml PeproTech 120-02
BMP-4 10 ng/ml PeproTech 120-05ET Results of Examples 2 and 3
Methods Used for Cell Morphology and Viability Analysis
Phase Contrast Microscopy and Trypan Blue Exclusion The growth of the spheroids was estimated with bare eyes and with Leica DMIL Led camera phase contrast microscope (11090, Leica Microsystems) with 5× and 10× magnifications. This microscope was also used to assess morphology of the spheroids. The images were captured using Leica EC3 Camera (Leica Microsystems) and processed with Leica Application Suite LAS EZ version 2.0.0. (Leica Microsystems). Sizes and the amount of the spheroids were estimated with phase contrast microscope and the average cell number in a spheroid was counted with Trypan Blue exclusion test (n=3). Also the average cell amount per well (n=5) was assessed similarly. At first spheroids were filtered through 100 μm filter (BD falcon; REF 352360) and collected in order to remove single dead cells and to get only spheroids to the study. Spheroids were washed in 1×DPBS (-) once. To get single cells for calculations spheroids were broken with cell dissociation buffer (Gibco®; 13151-014) which was incubated for 15 min at 37° C. and Accutase™ enzyme (cin DBBS/0.5 mM EDTA, Millipore; SCR005) 2 min at room temperature and filtered through 40 d filter (BD falcon; REF 352340). Cells were counted with Trypan blue in ratio of 1:5 (0.4%, Gibco®; 15250-061) by using hemocytometer.

Live/Dead Cell Viability Assay

Filtered samples were washed with 1% DPBS (-) and treated with LIVE/DEAD® Viability/Cytotoxicity kit (Invitrogen; L3224). Calcein AM used with concentration of 0.5 μM and Ethinidium homodimer-1 (EthD-1) 0.11M. Calcein AM produced green fluorescence in live cells (excitation wavelength ~495 nm and emission ~515 nm) and EthD-1 produced a red fluorescence in dead cells (excitation wavelength ~495 nm and emission ~635 nm). Dye was incubated for 30 minutes at room temperature in the dark. The staining was viewed with the same confocal microscope than used in immunofluorescence study. Cell viability in the spheroids was visualized under a high content screening microscope (Leica TCS SPII HCS A; Leica) at 37° C. with 5% CO2 using Argon 488 nm laser respectively, and 20×HCX PL APO 0.7 immersion corrected objective (Leica). Glycerol was used as immersion liquid. The confocal images were analyzed with Imaris Software version 7.6.5 (Bitplane AG). Cell viability was also estimated with Trypan Blue exclusion test while calculating spheroid size as presented in previous chapter.

Methods Used for Protein Expression Analysis
Immunofluorescence

Before immunofluorescence study cultured spheroids were collected. DE spheroids were filtered through 100 μm filter, washed in RPMI-1640 medium supplemented with GlutaMax, fixed in 4% PFA at room temperature for 10 minutes (2D) or 5 hours (3D) and then washed twice with 1×DPBS (-). Because of a big loss of spheroids caused by stickiness of the cells HP cells were fixed at first and after that filtered with 0.2% Tween (Sigma-Aldrich; T8787) in 1×DPBS (-). A part of the fixed and filtered spheroids were transferred into the new tubes for IHC and the rest of the cells were permeabilized with 0.1% Triton (x-100, Sigma-Aldrich; T8787) for 10 min (2D) or 30 min (3D). After washing two times and blocking with 10% normal donkey or goat serum (Millipore; NG1924057 and NG1928752, respectively) 1 h at room temperature (2D) or overnight at 4° C. (3D), cells were incubated with primary antibodies at 4° C. overnight in parallel.

To characterize 2D stem cells anti-Oct-3/4 and anti-NANOG were used along with negative controls rabbit immunoglobulin G (IgG) or goat IgG (Table 4). To assess DE stage antibodies chosen were anti-Oct-3/4, anti-CXCR4, anti-AFP, anti-HNF3B and anti-NANOG, and for negative controls rabbit IgG, mouse IgG or goat IgG (Table 4). For HP stage antibodies used were anti-AFP, anti-CK19, anti-HNF4A, and anti-albumin (ALB), and negative controls were mouse IgG or goat IgG (Table 4).

TABLE 4

The primary and secondary antibodies, and the blocking of non-specific
protein-protein interactions used in the immunofluorescence studies
(Ab = antibody, DE = definitive endoderm, HP = hepatic progenitor, GS = goat
serum, DS = donkey serum, g = goat, d = donkey, IgG = immunoglobulin).

| Antigen | Antigen type | Blocking | 1st Ab | 2nd Ab |
| --- | --- | --- | --- | --- |
| Oct 3/4 | Pluripotency marker | 10% GS | Santa Cruz Biotechnology sc-9081, 1:500 | g anti-rabbit IgG 594 |
| NANOG | Pluripotency marker | 10% DS | R&D Systems ® AF1997, 1:50 | d anti-goat IgG 594 |
| HNF3B | DE cell marker | 10% DS | Santa Cruz Biotechnology sc-6554, 1:50 | d anti-goat IgG 594 |
| CXCR4 | DE cell marker | 10% GS | R&D Systems ® MAB172, 1:50 | g anti-mouse IgG 594 |
| HNF4A | HP cell marker | 10% DS | Santa Cruz Biotechnology sc-6556, 1:200 | d anti-goat IgG 594 |
| CK19 | HP cell marker | 10% GS | Santa Cruz Biotechnology sc-6278, 1:50 | g anti-mouse IgG 594 |
| AFP | Early hepatocyte marker | 10% GS | Sigma-Aldrich ® A8452, 1:500 | g anti-mouse IgG 594 |
| CYP3A4 | Hepatocyte marker | 10% GS | Millipore AB1254, 1:500 | g anti-rabbit IgG 594 |
| ALB | Hepatocyte marker | 10% DS | Bethyl laboratories, inc. A80-229A, 1:500 | d anti-goat IgG 594 |
| m IgG | Negative control | 10% GS | Santa Cruz Biotechnology sc-2027, 1:40 | g anti-mouse IgG 594 |

TABLE 4-continued

The primary and secondary antibodies, and the blocking of non-specific
protein-protein interactions used in the immunofluorescence studies
(Ab = antibody, DE = definitive endoderm, HP = hepatic progenitor, GS = goat
serum, DS = donkey serum, g = goat, d = donkey, IgG = immunoglobulin).

| Antigen | Antigen type | Blocking | 1st Ab | 2nd Ab |
|---------|--------------|----------|--------|--------|
| rb IgG | Negative control | 10% GS | Santa Cruz Biotechnology sc-2027, 1:1000 | g anti-rabbit IgG 594 |
| g IgG | Negative control | 10% DS | Santa Cruz Biotechnology sc-2028, 1:100 | d anti-goat IgG 594 |

The secondary antibodies used were goat-anti-mouse Alexa Fluor 594 (Invitrogen; A11032, 1:400), goat-anti-rabbit Alexa Fluor 594 (Invitrogen; A11012, 1:400) or donkey-anti-goat Alexa Fluor 594 (Invitrogen; A11058, 1:400). All secondary antibodies have emission and excitation wavelengths 617 nm and 597 nm, respectively. After washing the samples three times, secondary antibodies were added and incubated at room temperature 60 min (2D) or 6 h (3D). All washings were performed with 0.2% Tween 20 in 1×DPBS (−). Samples were washed once with 0.2% Tween 20 in MilliQ water and nuclei stain DAPI (Sigma-Aldrich; D8417-MG, 1:200) was incubated 2 min (2D) or 10 min (3D). At last spheroids were transferred to the 96-well plate with glass bottom (Matrical Bioscience; 0509129L22) and mounted with SlowFade® Gold antifade reagent (Invitrogen; S36937). Cells from 2D culturing were mounted with ProLong® Gold antifade reagent (Invitrogen; P36934) and glasses were covered with 24×60 mm coverslips (#1.5).

The staining was viewed under the same high content screening microscope than used in viability testing. Lasers used were diode 405 nm for nuclei color with excitation and emission wavelengths 358 and 461 respectively, and DPSS 561 nm for Alexa Fluor 594 and as objective 20×HCX PL APO 0.7 immersion corrected objective with glycerol was used. The confocal images were analyzed with Imaris Software version 7.6.5.

Immunohistochemistry

For immunohistochemistry assays spheroids were collected, washed and filtered as mentioned earlier. The cells were dyed with a black dye (TMD Tissue Marking Dye Black TMD-131L, a sample from FC lab) and embedded in HistoGel (Thermo Scientific HG-4000-012) in order to make sample handling easier. Samples were sent to the Finnish Center for Laboratory Animal Pathology for the standard paraffin embedding and sectioning. Sections were 5 m thick. Actual immunohistochemistry study was performed by removing paraffin at first from objective glasses with Xylenes (Sigma-Aldrich; 534056-4L) and rehydrating slides with 99.5%, 94%, 70%, 50% ethanol (Altia) and MilliQ water stepwise. To unmask the antigenic sites from paraffin embedding, sections were boiled for 10 minutes in antigen retrieval buffer consisting of 10 mM Sodium Citrate tribasic hydrate (Sigma-Aldrich; 4641-5006) and 0.05% Tween 20 in 1×TBS and pH 6.0. After antigen retrieval the slides were cooled down with cold running water for 10 min and washed with washing buffer twice for 5 minutes. The washing buffer consisting of 0.1% saponin (Serva; 34655.01) in 1×TBS. Cells were permeated with 0.1% Triton or 0.5% saponin for 10 minutes if needed depending on the later used antibody (Tables 5 and 6). After permeation the slides were washed once with washing buffer and blocked with 10% donkey or goat serum for 2 hours at room temperature and then incubated with primary antibodies at +4° C. overnight. The used antibodies are presented in Table 5 for DE cells and in Table 6 for HP cells. On the next day the slides were washed three times with washing buffer and incubated with secondary antibodies for 1 hour at room temperature in dark. After incubation the slides were washed again three times with washing buffer and twice for 15 minutes with Hanks' Balanced Salt Solution (HBSS, Gibco®; 14025-050) and then nuclear staining was performed with 0.2 µM Sytox® Green nucleic acid stain (Invitrogen; 57020) for 30 minutes at room temperature in dark. Before mounting with Vectashield® Hard Set™ Mounting medium (Vector Laboratories, inc.; H-1400) the slides were washed again twice with HBSS. Paraffin pen (Sigma-Aldrich; Z672548) used during the staining to mark the sample area was spreading during the staining and disturbing the nuclear staining so the paraffin removal had to be performed again with ethanol and xylenes treatment and then the nuclear staining was repeated and the slides were mounted again with Vectashield® mounting medium. After mounting the glasses were covered with coverslips.

TABLE 5

The primary and secondary antibodies, permeation, and blocking of non-specific
protein-protein interactions used in the immunohistochemistry study of definitive
endoderm cells (Ab = antibody, GS = goat serum, DS = donkey serum,
g = goat, d = donkey, IgG = immunoglobulin).

| Antigen | Antigen type | Permeation | Blocking | 1st Ab | 2nd Ab |
|---------|--------------|------------|----------|--------|--------|
| CXCR4 | DE cell marker | None | 10% GS | 1:50, 1:200 | g anti-mouse IgG 594 |
| b-tub | Neural cell marker | 0.1% Triton | 10% GS | Sigma-Aldrich® T5076, 1:1000 | g anti-mouse IgG 595 |
| MA | Muscel cell marker | 0.1% Triton | 10% GS | Dako IR70061-2, ready | g anti-mouse IgG 596 |
| HNF3B | DE cell marker | 0.1% Triton | 10% DS | 1:50 | d anti-goat IgG 594 |
| m IgG | Negative control | 0.1% Triton | 10% GS | 1:40, 1:400 | g anti-mouse IgG 594 |
| g IgG | Negative control | 0.1% Triton | 10% DS | 1:100 | d anti-goat IgG 594 |

TABLE 6

The primary and secondary antibodies, permeation, and blocking of non-specific protein-protein interactions used in the immunohistochemistry study of definitive endoderm cells (Ab = antibody, SAP = saponin, GS = goat serum, DS = donkey serum, g = goat, d = donkey, IgG = immunoglobulin).

| Antigen | Antigen type | Permeation | Blocking | 1st Ab | 2nd Ab |
|---------|--------------|------------|----------|--------|--------|
| AFP | Early hepatocyte marker | 0.5% SAP | 10% GS | 1:500 | g anti-mouse IgG 594 |
| CK19 | HP cell marker | 0.5% SAP | 10% GS | 1:50 | g anti-mouse IgG 594 |
| ALB | Hepatocyte marker | 0.5% SAP | 10% DS | 1:500 | d anti-goat IgG 594 |
| SSEA-4 | Pluripotency marker | 0.5% SAP | 10% GS | 1:100 | g anti-mouse IgG 594 |
| HNF4A | HP cell marker | 0.1% Triton | 10% DS | 1:200 | d anti-goat IgG 594 |
| CXCR4 | DE cell marker | None | 10% GS | 1:50 | g anti-mouse IgG 594 |
| HNF3B | DE cell marker | 0.1% Triton | 10% DS | 1:50 | d anti-goat IgG 594 |
| m IgG | Negative control | 0.5% SAP | 10% GS | 1:100 | g anti-mouse IgG 594 |
| g IgG | Negative control | 0.1% Triton | 10% DS | 1:100 | d anti-goat IgG 594 |

The staining was viewed under a high content screening microscope similarly than immunofluorescence study, only for nuclei color there were used Argon 488 nm laser instead of diode 405 nm laser due to Sytox® Green having emission and excitation wavelengths 523 and 504 nm, respectively.

Flow Cytometry

For flow cytometry assay the cells in 2D culture were washed with 1×DPBS (−), detached with cell dissociation buffer (Enzyme-Free PBS-based, Gibco®; 13151-014) for 15 min at 37° C. and accutase (cin DPBS/0.5 mM EDTA, Millipore; SCR005) for 2 min at room temperature, collected, and finally washed with mTeSR1 medium. Spheroids for flow cytometry study were collected from culturing plate with 1% DPBS (−) and transferred into 15 ml tube. Spheroids were filtered through 100 m filter. After washing the cells twice with 1% DPBS (−) spheroids were broken by incubating with cell dissociation buffer for 15 min in 37° C. and with accutase for 2 min at room temperature and washed with mTeSR1 medium. For each assay the cell number was counted with Trypan Blue (Gibco®; 15250-061) and then the cells were stained. In staining procedure the cells were divided into unstained cells, cells stained with negative control mAPC (Goat anti-mouse IgG ads-APC, SouthernBiotech; 1031-11S, 1:300) and cells stained with both antibody and mAPC. Cells were incubated with primary antibody on ice for 60 minutes, washed with 2% FBS (PAA Laboratories GmbH, A15-151) and after that mAPC was incubated in dark on ice for 40 min and again added 2% FBS. For cells on pluripotent stage the antibody used was SSEA-4 (mouse anti-SSEA-4, Developmental Studies Hybridoma Bank, MC-813-70, 1:400) and DE cells were characterized with CXCR4 (R&D Systems®; MAB172, 1:50). The samples were analyzed on a BD CSR II Flow Cytometry (BD Biosciences; 26526) and the data was handled with BD FACSDiva™ software version 6.2. (BD Biosciences).

From Pluripotent Spheroids into Definitive Endoderm Spheroids According to Example 2

Cell Morphology and Viability

Figure 6:
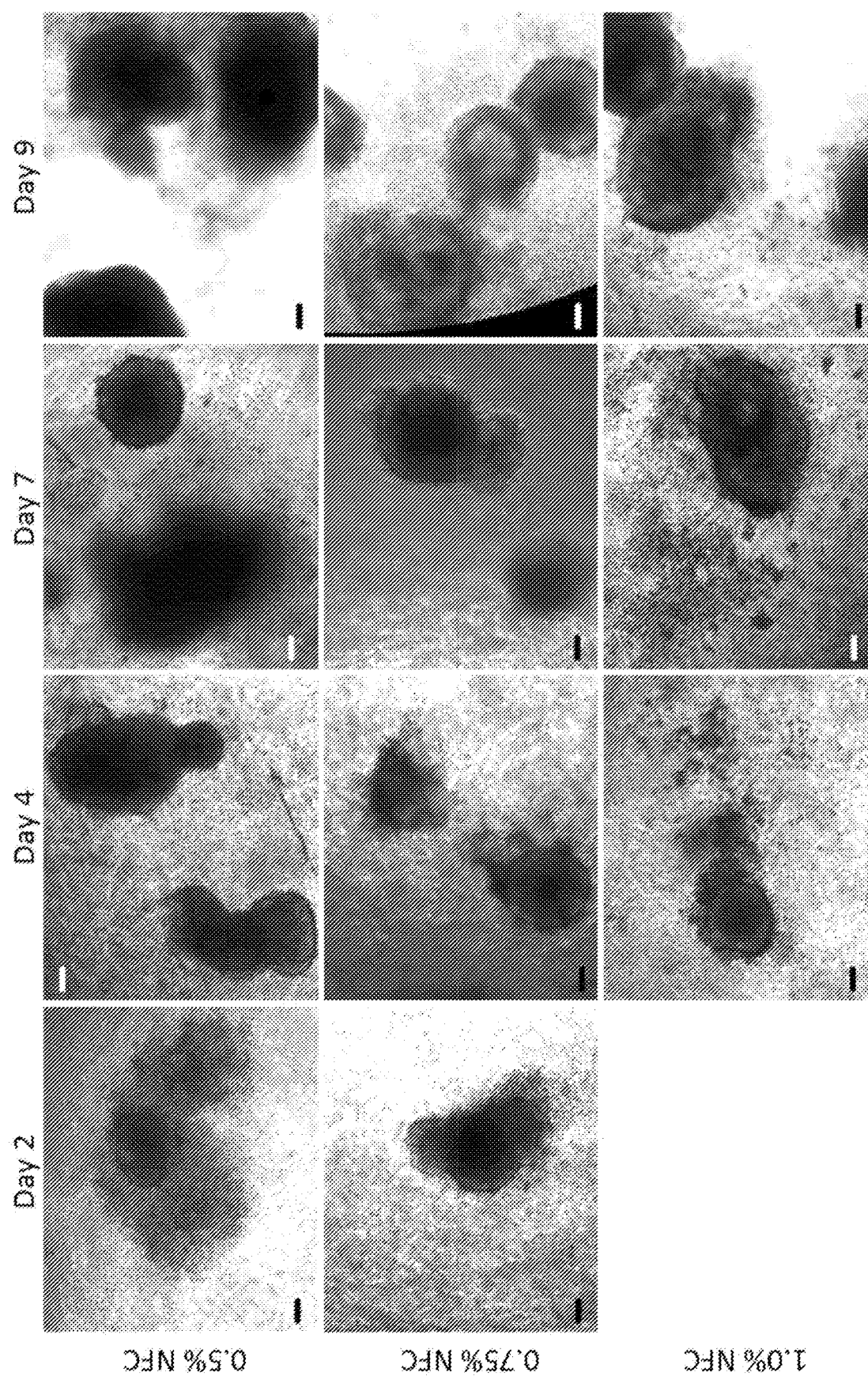
FIG. 6. Phase-contrast microscope images of cell spheroids in 3D differentiation culture from pluripotent stem cell spheroids into definitive endoderm (DE) spheroids.

Most of the spheroids were maintained during DE induction stage, although some went broken while mixing with new NFC hydrogel, especially with 1.0% concentration. During DE induction there was also cloudiness seen around many spheroids and spheroid morphology showed more variability compared to pluripotent spheroids, there were plenty of spheroids coalesced while growing. FIG. 6 shows phase-contrast microscope images of cell spheroids in three-dimensional differentiation culture from pluripotent stem cell spheroids into definitive endoderm (DE) spheroids in 0.5%, 0.75% or 1.0% NFC hydrogel. Images were taken 2, 4, 7 and 9 days after DE induction start. The scale bars are 100 µm. The phase-contrast images revealed spheroids diameter increasing during induction and there were also new spheroids forming even though growth was more slowly than during pluripotent culturing. Spheroids had diameters between 100-650 µm after seven days DE induction and 100-700 µm after nine days induction. There was no remarkable variability in size or morphology between spheroids grown in different NFC hydrogel concentrations.

Figure 7:
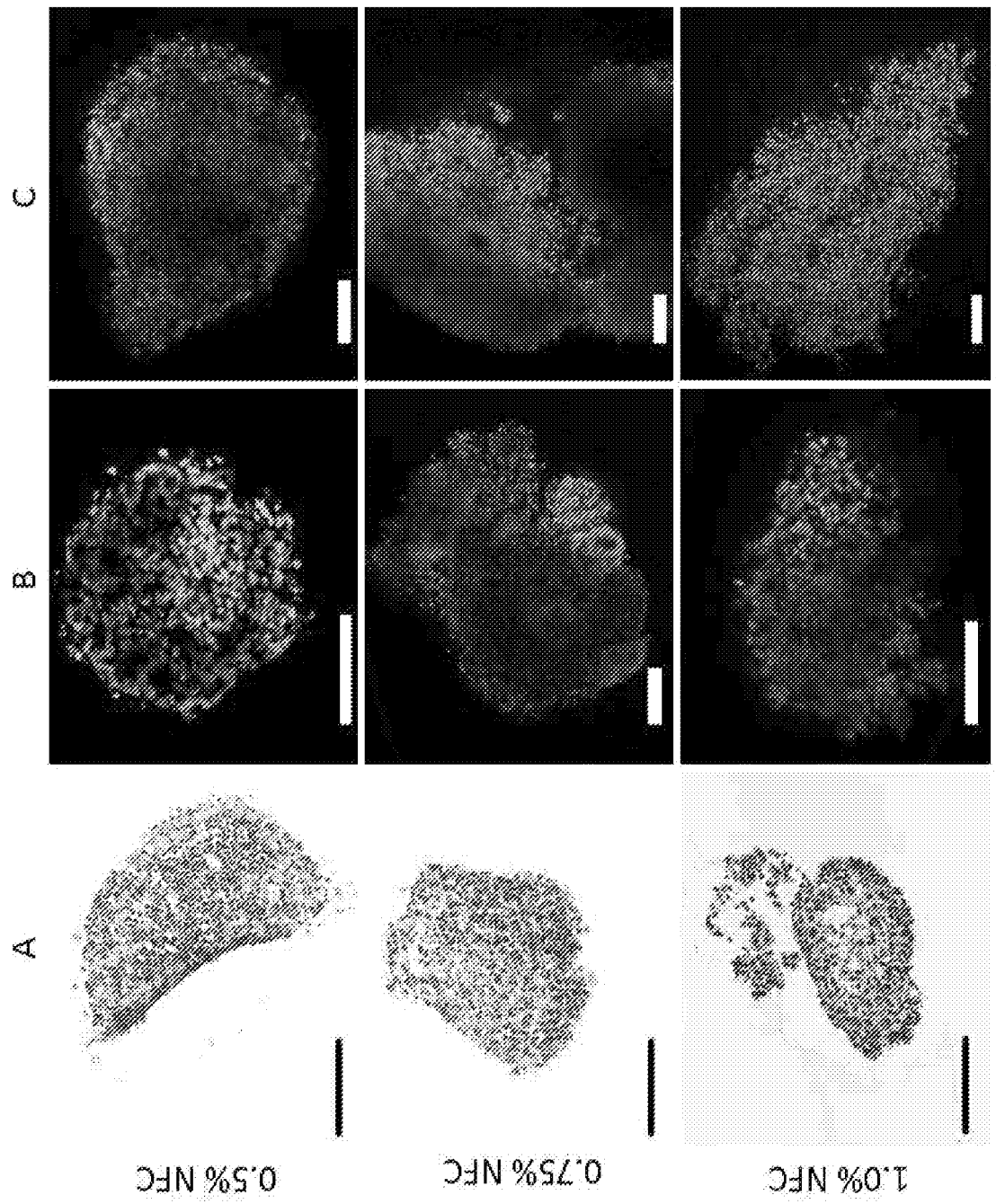
FIG. 7. Morphology inside the differentiated cell spheroids from pluripotent stage until definitive endoderm spheroids.
Figure 8:
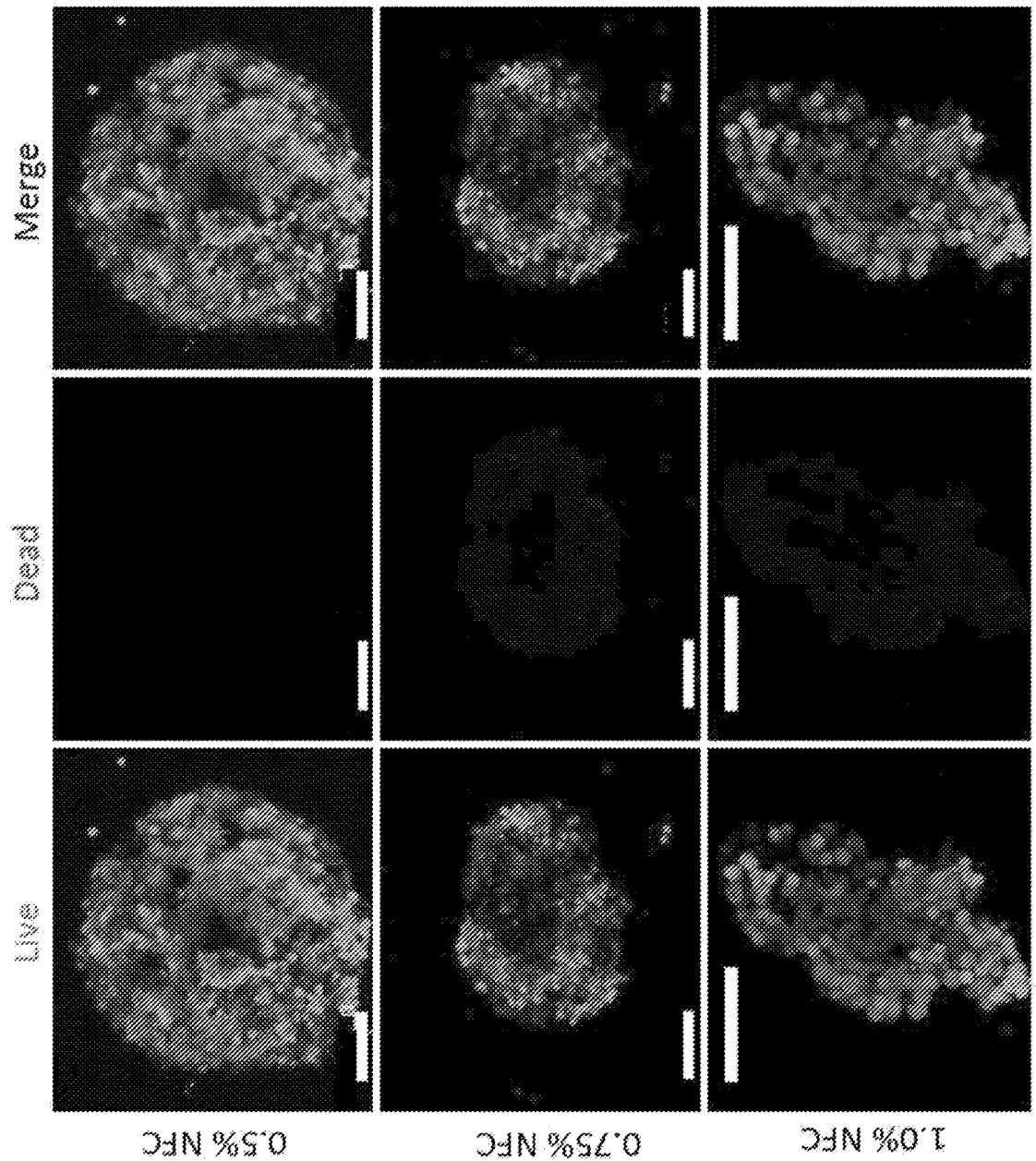
FIG. 8. Viability of the 3D cultured spheroids 7 days after the beginning of definitive endoderm induction based on live/dead viability testing.

FIG. 7 shows morphology inside the differentiated cell spheroids from pluripotent stage until definitive endoderm spheroids. Panel A presents phase-contrast microscope images from hematoxylin and eosin stained samples from histological sections. High content screening microscope images were taken after 6 (panel B) or 9 days (panel C) differentiation and cellulase treatment. Spheroids were grown in 0.5%, 0.75% or 1.0% NFC hydrogel. The scale bars are 100 µm. With paraffin section samples and high content screening microscope it is possible to see inside the spheroids and conclude that inside the spheroids are full of cells. FIG. 8 shows viability of the 3D cultured spheroids 7 days after the beginning of definitive endoderm induction based on live/dead viability testing. Culturing conditions were alternatively 0.5%, 0.75% or 1.0% NFC hydrogel. The scale bars are 100 m. There are seen small changes on the spheroid structure, very small cavities formed by cell organization which is typical for definitive endoderm structure. The cells in the spheroids remained alive during DE differentiation culture as seen from the results from live/dead viability assays at the seventh day after induction start.

Protein Expression in Whole Mount Spheroids

Figure 9:
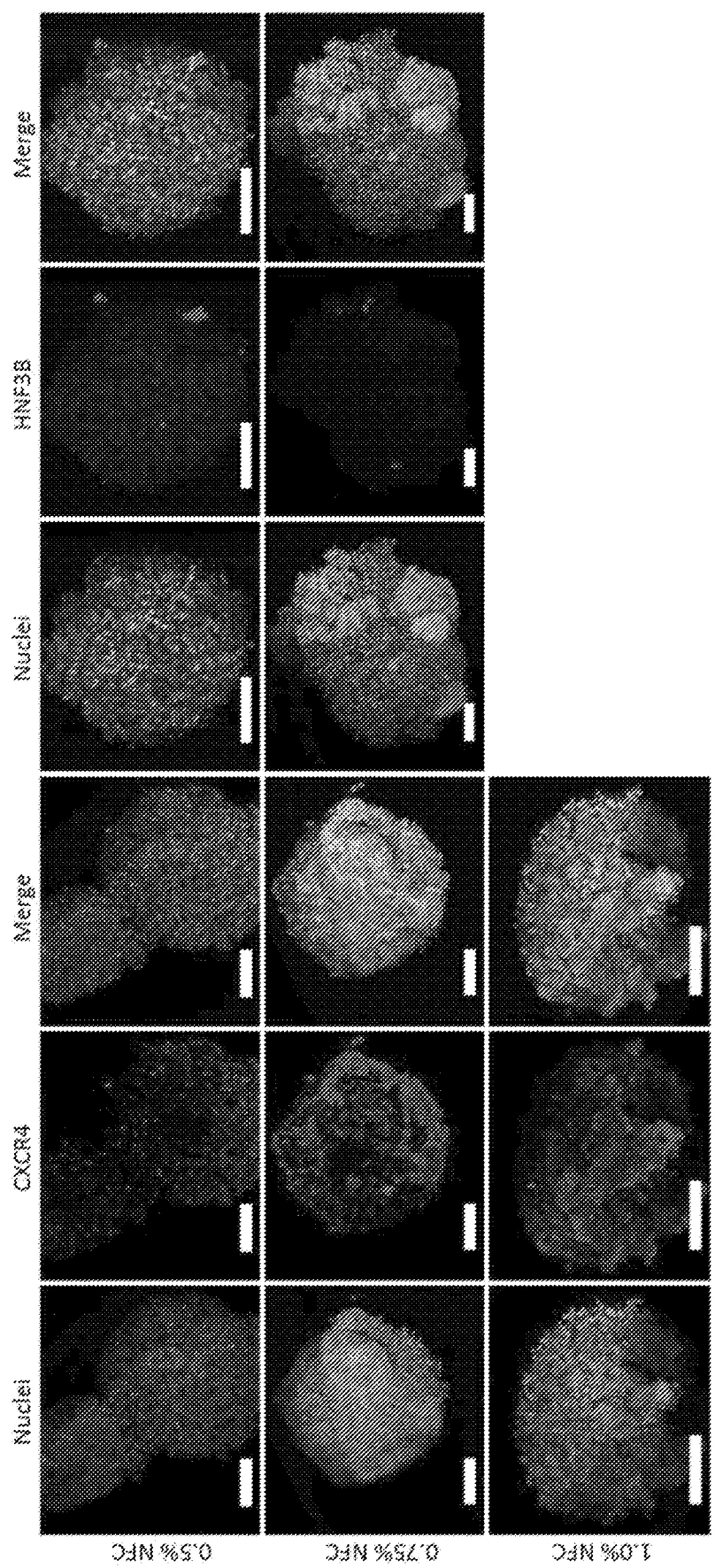
FIG. 9. Expression of definitive endoderm markers CXCR4 and HNF3B in 3D differentiated cell spheroids from pluripotent stage until definitive endoderm spheroids FIG. 10. Expression of (A) pluripotency markers OCT4 and NANOG and (B) early hepatocyte marker AFP in 3D cultured cell spheroids from pluripotent stage until definitive endoderm spheroids.

In order to see whether the cells were differentiated into definitive endoderm stage the cells were stained with DE markers. FIG. 9 shows expression of definitive endoderm markers CXCR4 and HNF3B in three-dimensionally differentiated cell spheroids from pluripotent stage until definitive endoderm spheroids. Culturing performed in 0.5%, 0.75% or 1.0% NFC hydrogel for 6 days. The scale bars are 100 µm. High content screening microscope images from the spheroids differentiated for 6 days before cellulase treatment show spheroids had positivity for DE marker CXCR4 especially with NFC hydrogel concentrations 0.75% and 1.0% (FIG. x). On the other hand only spheroids grown in 0.5% NFC hydrogel clearly expressed DE marker HNF3B.

Figure 10:
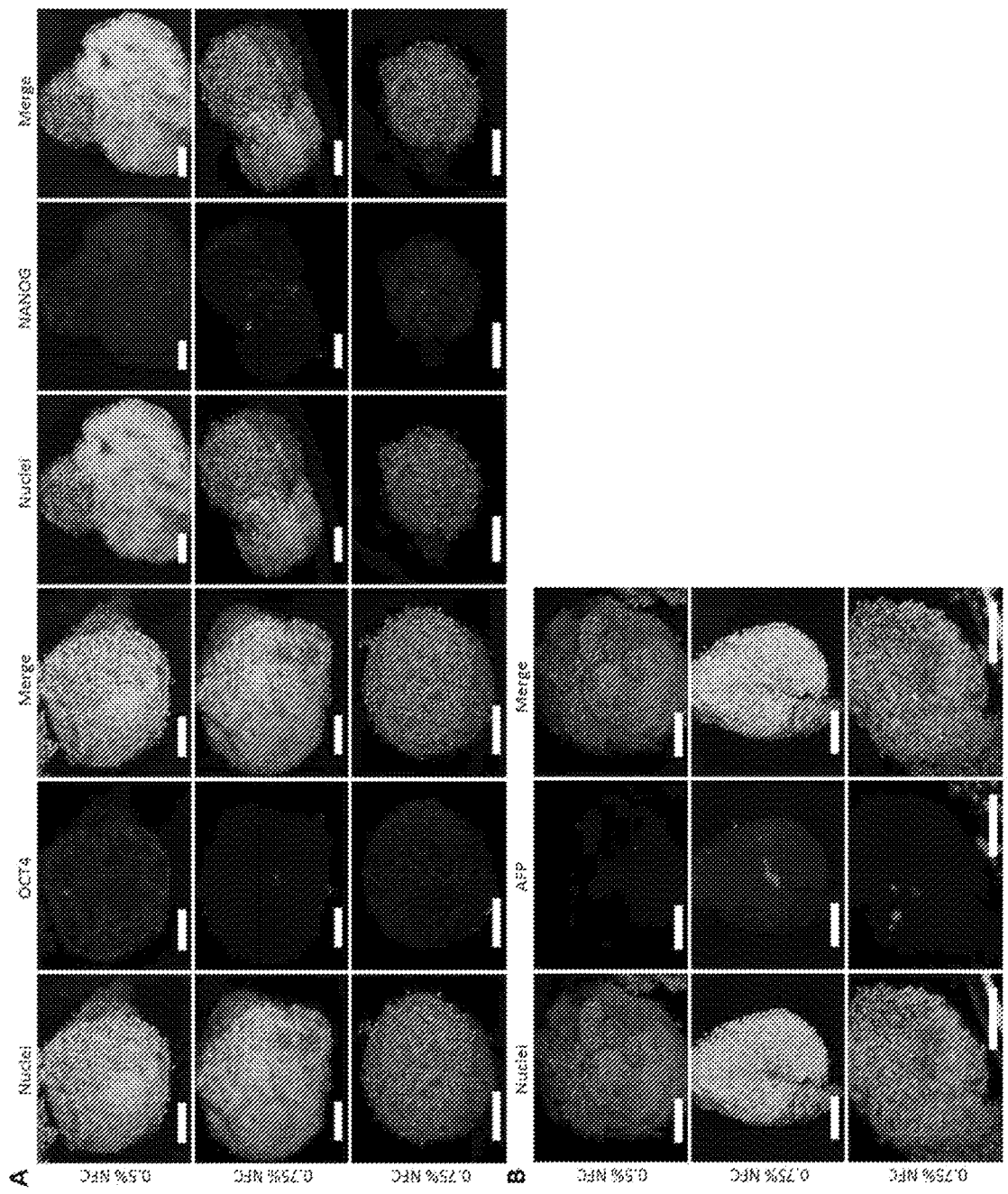

FIG. 10 shows expression of (A) pluripotency markers OCT4 and NANOG and (B) early hepatocyte marker AFP in 3D cultured cell spheroids from pluripotent stage until definitive endoderm spheroids. Differentiation performed in 0.5%, 0.75% or 1.0% NFC hydrogels for 6 days. The scale bars are 100 µm. There was some positivity seen for pluripotency markers OCT4 and NANOG in spheroids grown in 0.5% NFC hydrogel whereas spheroids from 0.75% hydrogel showed variability, there were both positive and negative spheroids for this marker (FIG. 10 A). Expression of early hepatocyte marker AFP on the spheroids is seen on FIG. 10 B. Spheroids from all NFC hydrogel concentrations were negative for this marker.

Figure 11:
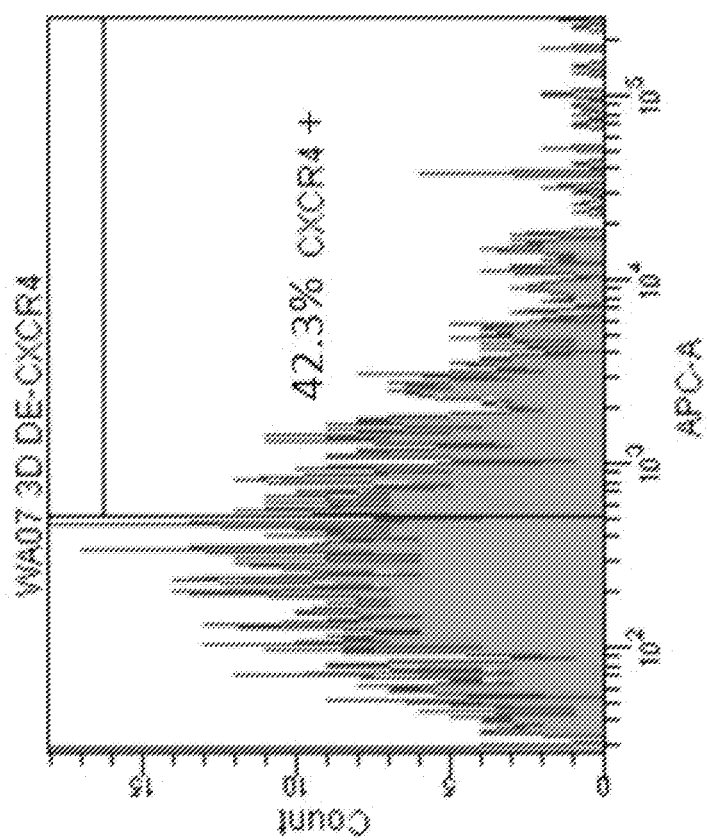
FIG. 11. Fraction of definitive endoderm (DE) marker CXCR4 positive cells after 3D DE induction in 0.5% nanofibrillar cellulose hydrogel for 6 days.
Figure 11:
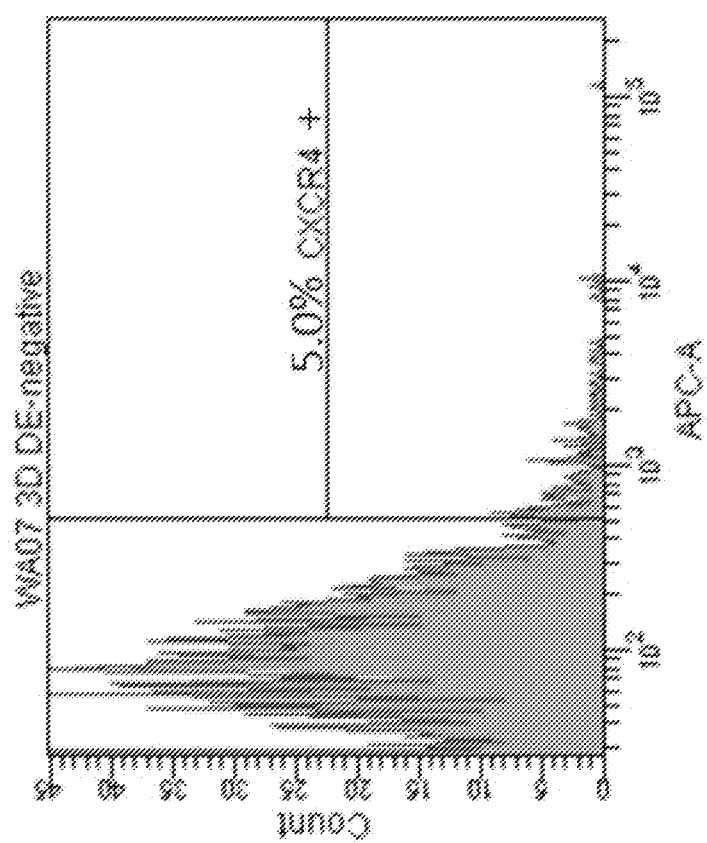

FIG. 11 shows fraction of definitive endoderm (DE) marker CXCR4 positive cells after three-dimensional DE induction in 0.5% NFC hydrogel for 6 days. Flow cytometry study reveals that only 42.3% of the cells from population of 2500 expressed DE marker CXCR4.

Figure 12:
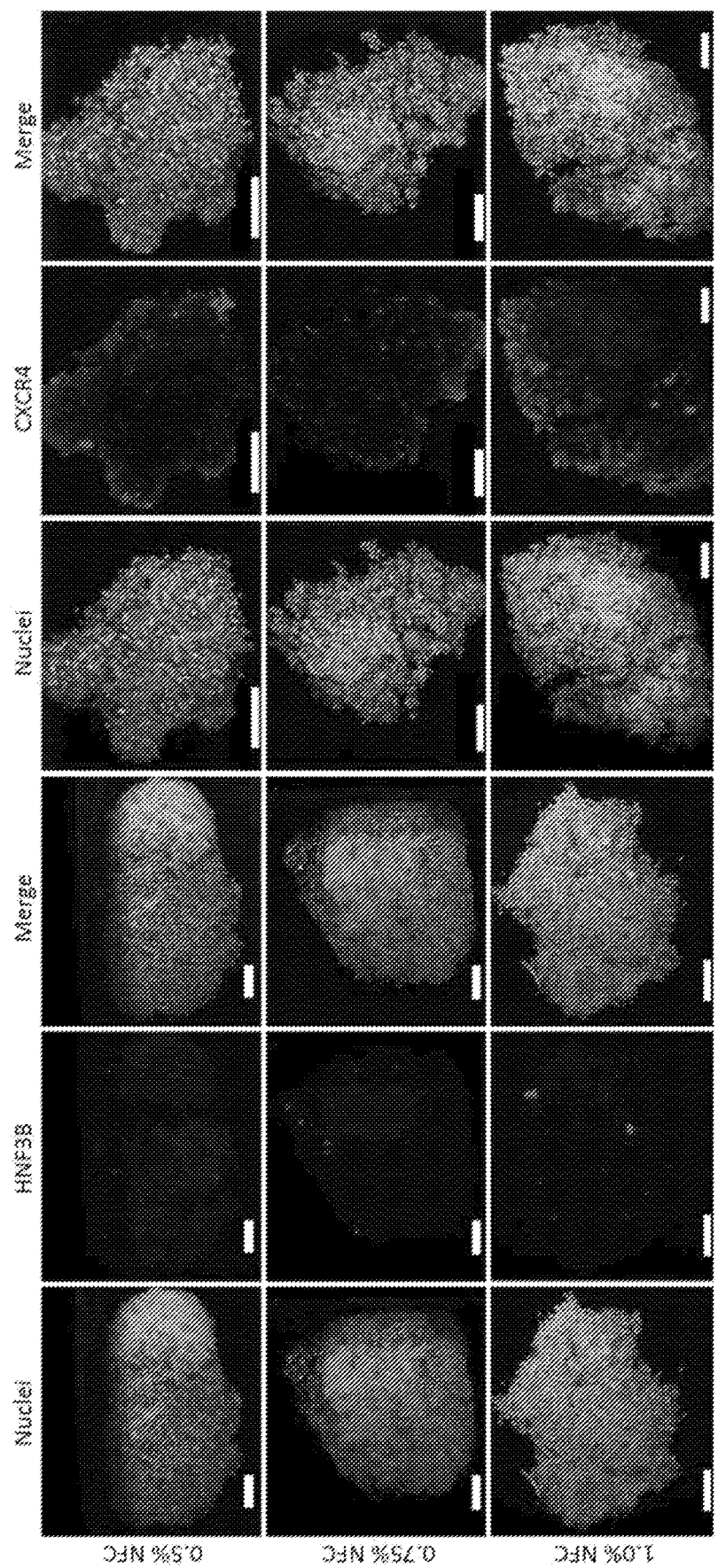
FIG. 12. Expression of definitive endoderm markers CXCR4 and HNF3B in spheroids cultured 3D from pluripotent stage until definitive endoderm spheroids.
Figure 13:
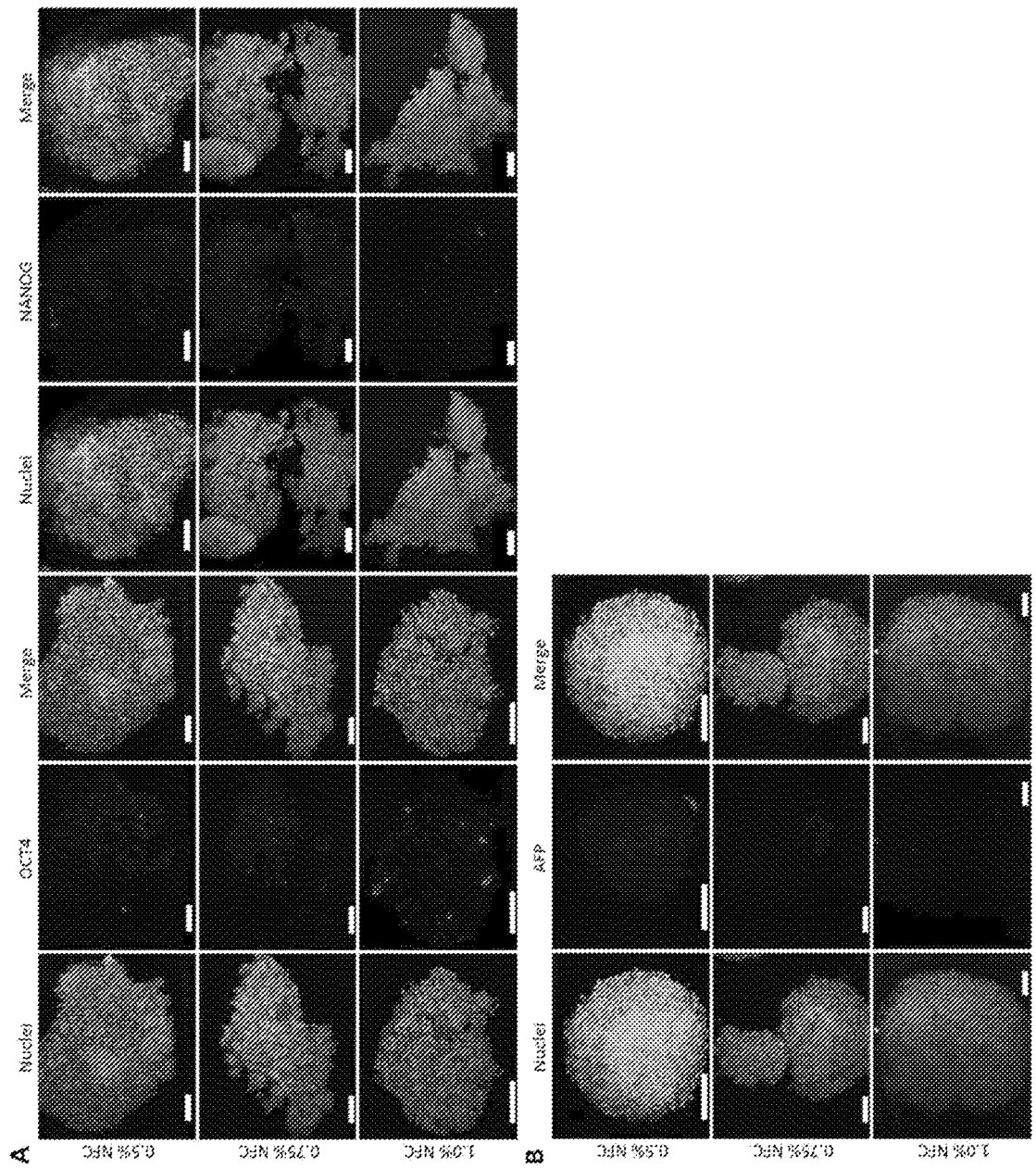
FIG. 13. Expression of (A) pluripotency markers OCT4 and NANOG and (B) early hepatocyte marker AFP in spheroids differentiated 3D from pluripotent stage until definitive endoderm stage.

FIG. 12 shows expression of definitive endoderm markers CXCR4 and HNF3B in spheroids cultured three-dimensionally from pluripotent stage until definitive endoderm spheroids. Differentiation performed in 0.5%, 0.75% or 1.0% NFC hydrogel for 9 days. The scale bars are 100 µm. After nine days of differentiation and cellulase treatment all spheroids showed little less positivity for DE markers HNF3B and CXCR4 than after six days differentiation. FIG. 13 shows expression of (A) pluripotency markers OCT4 and NANOG and (B) early hepatocyte marker AFP in spheroids differentiated three-dimensionally from pluripotent stage until definitive endoderm stage. Culturing performed in 0.5%, 0.75% or 1.0% NFC hydrogel for 9 days. The scale bars are 100 µm. Spheroids expressed less also pluripotency markers OCT4 and NANOG, however being still positive (FIG. 13 A). Early hepatocyte marker AFP expression was not present in any spheroids (FIG. 13 B).

FIG. 14 shows a summary of the protein expressions in differentiated spheroids studied by immunofluorescence (IF). Spheroids were differentiated for 6 or 9 days from pluripotent stem cell stage until definitive endoderm spheroids in 0.5%, 0.75% or 1.0/NFC hydrogels. The amount of expression is scaled from no expression (−) to high expression (+++), lack of result is presented with a question mark. The tables in FIG. 14 summarize all protein expressions studied by immunofluorescence for each type of culturing environment and period. Spheroids grown for nine days showed less positivity with DE cell markers than cells differentiated for six days. 0.5% NFC hydrogel showed less variation between the spheroids and higher expression with DE markers than 0.75%. Data for 1.0% NFC hydrogel not shown.

Protein Expression Inside the Spheroids

To determine whether the cells inside the spheroids were differentiated into definitive endoderm stage we performed IHC stainings with critical markers on histological section samples. All samples studied were differentiated for six days before releasing them from hydrogel with cellulase.

Figure 15:
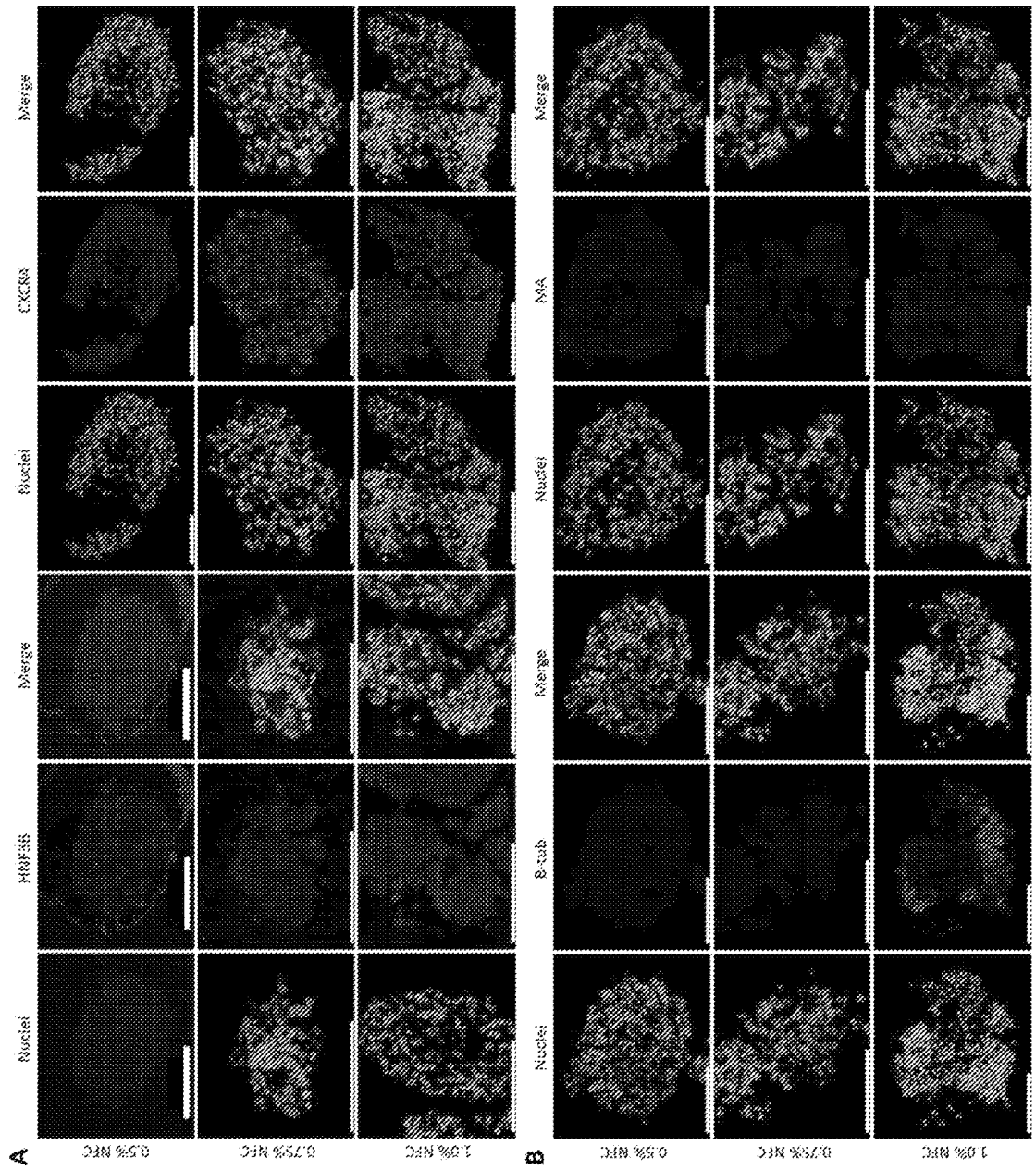
FIG. 15. Expression of (A) definitive endoderm markers HNF3B and CXCR4 and also (B) mesoderm cell marker muscle actin (MA) and ectoderm cell marker β-tubulin III (B-tub) in cells inside spheroids differentiated 3D from pluripotent until definitive endoderm stage.

FIG. 15 shows expression of (A) definitive endoderm markers HNF3B and CXCR4 and also (B) mesoderm cell marker muscle actin (MA) and ectoderm cell marker β-tubulin III (B-tub) in cells inside spheroids differentiated three-dimensionally from pluripotent until definitive endoderm stage. Differentiation performed in 0.5%, 0.75% or 1.0% NFC hydrogel for 6 days. The scale bars are 100 µm. All samples showed positivity for DE marker HNF3B (FIG. 15 A). DE marker CXCR4 expression was strong in cells cultured in 0.75% or 1.0% NFC hydrogel but positivity was little less with cells differentiated in 0.5% hydrogel. Mesoderm cell marker muscle actin in cells from all NFC concentrations and ectoderm cell marker β-tubulin III in cells grown in 0.5% and 0.75% NFC hydrogel were negative whereas β-tubulin expression was positive in cells from 1.0% hydrogel (FIG. 15 B).

FIG. 16 shows a summary of the protein expressions in differentiated cells inside spheroids studied by immunohistochemistry (IHC). Spheroids were differentiated for 6 days from pluripotent stem cell stage until definitive endoderm spheroids in 0.5%, 0.75% or 1.0% NFC hydrogels. The amount of expression is scaled from no expression (−) to high expression (+++).

6 day-DE induction in 0.5% NFC hydrogel was chosen in the next experiment to further differentiate DE spheroids to hepatic progenitor spheroids.

From Pluripotent Spheroids into Hepatic Progenitor Spheroids According to Example 3

Cell Morphology and Viability

Figure 17:
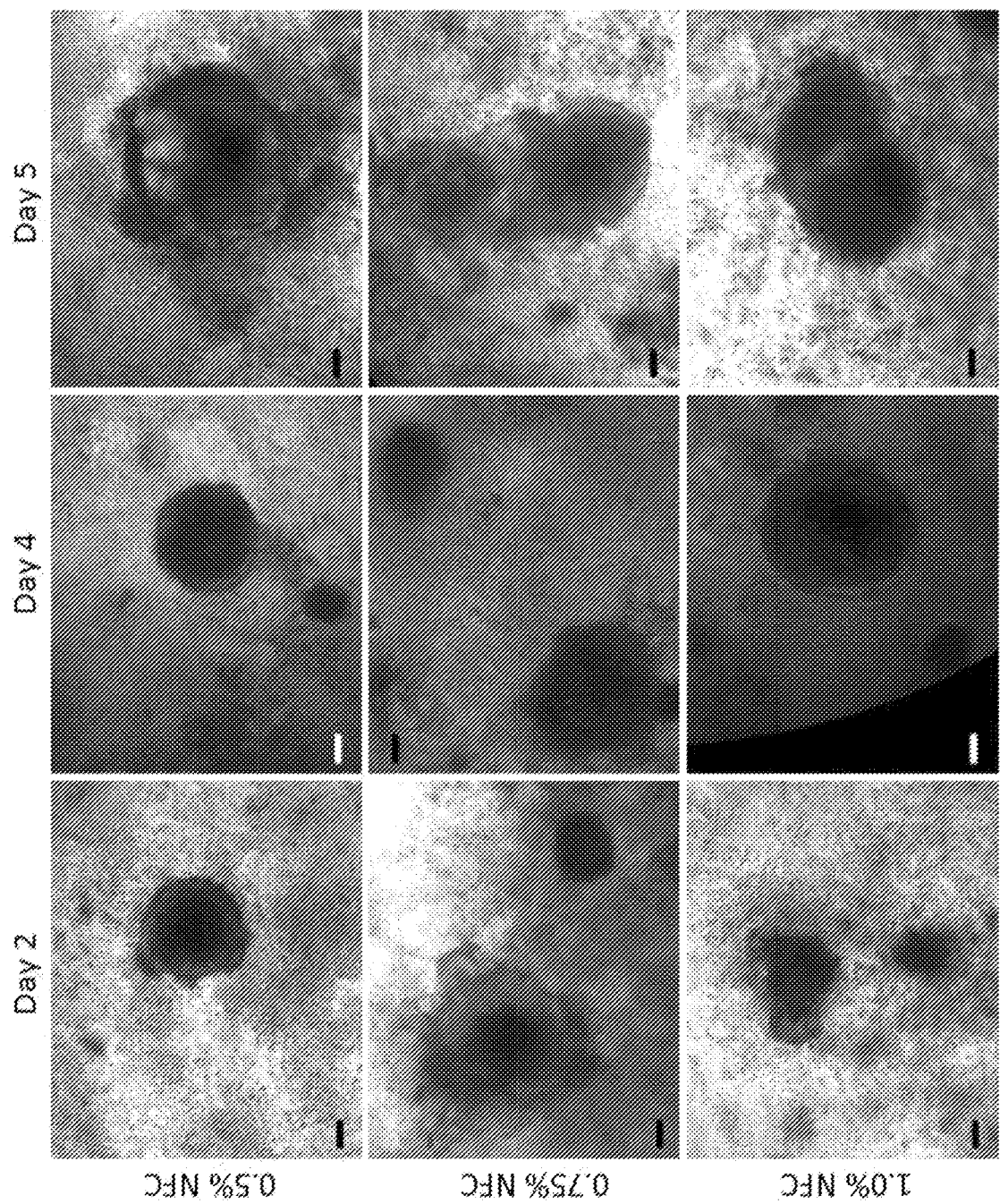
FIG. 17. Phase-contrast microscope images of cell spheroids in 3D culture differentiated from definitive endoderm stage into hepatic progenitor (HP) spheroids.

FIG. 17 shows phase-contrast microscope images of cell spheroids in three-dimensional culture differentiated from definitive endoderm stage into hepatic progenitor (HP) spheroids in 0.5%, 0.75% or 1.0% NFC hydrogel. Images were taken 2, 4 and 5 days after HP induction start. The scale bars are 100 µm. During differentiation from definitive endoderm to hepatic progenitor stage phase-contrast images showed spheroids were remained with increasing diameter even though the growth was slower than in DE stage. There were also seen some new and coalesced spheroids formed during this induction step. The cloudiness seen during DE phase increased and the shapes of spheroids became even more diverse.

Figure 18:
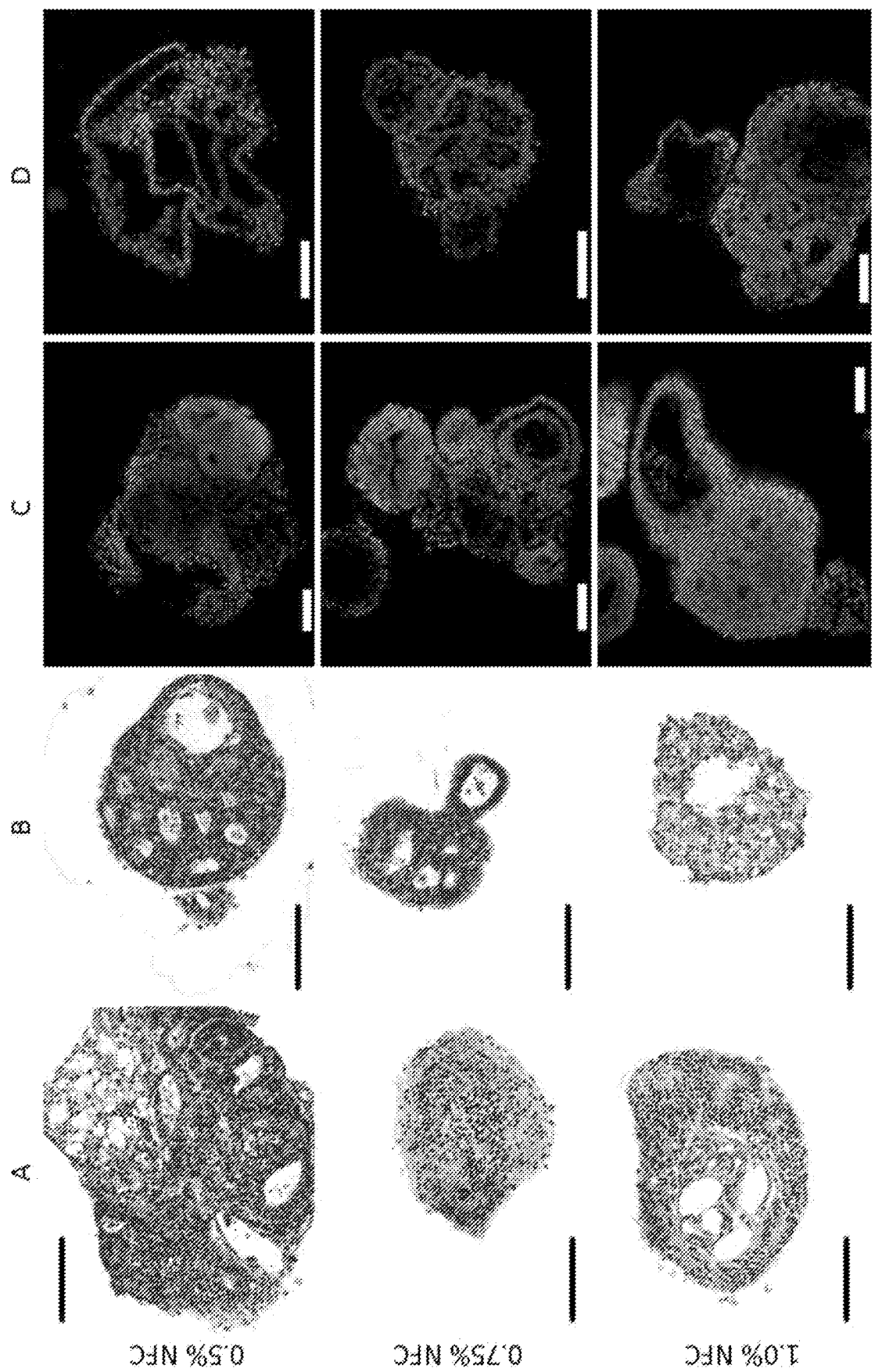
FIG. 18. Morphology inside the differentiated spheroids from definitive endoderm stage to hepatic progenitor spheroids.

FIG. 18 shows morphology inside the differentiated spheroids from definitive endoderm stage to hepatic progenitor spheroids. Panels A and B presents phase-contrast microscope images from hematoxylin and eosin stained samples from histological sections. High content screening microscope images are seen in panels C and D. Spheroids were differentiated in 0.5%, 0.75% or 1.0% NFC hydrogel for 4 days before cellulase treatment. The scale bars are 100 m. The phase contrast images from histological sections and confocal microscope images shows that inside the spheroids there were still cells but many spheroids had also big cavities caused by cell organization. At the inner surface the cavities cells were tightly aligned to each other to form a monolayer. These specific structures are characteristic of definitive endoderm-derived epithelia. There were also clear areas of higher cell density and lower cell density.

Protein Expression in Whole Mount Spheroids

Figure 19:
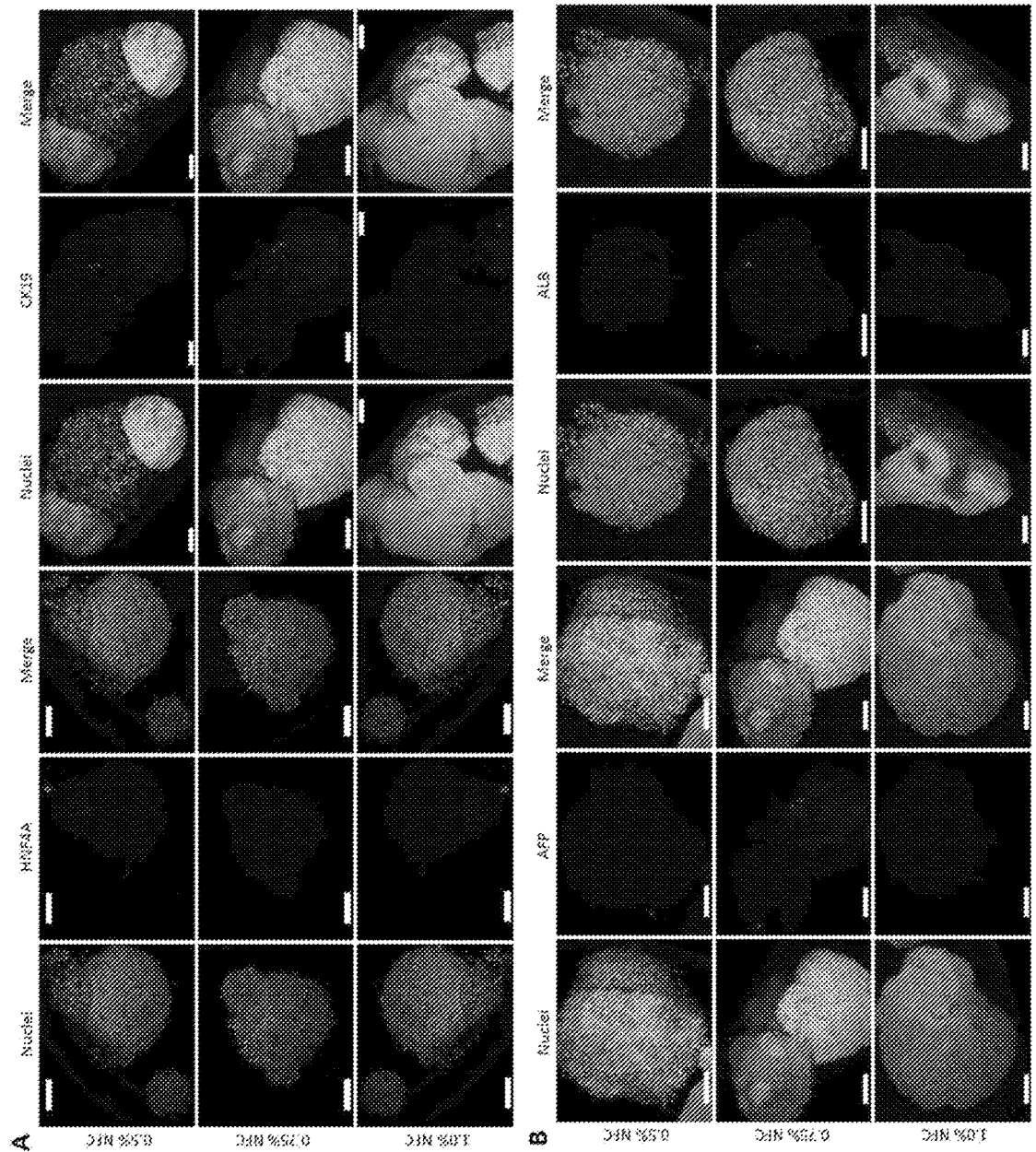
FIG. 19. Expression of (A) hepatic progenitor markers HNF4A and CK19 and also (B) early hepatocyte marker AFP and hepatocyte marker albumin (ALB) in spheroids differentiated three-dimensionally from pluripotent stage to hepatic progenitor (HP) stage.
Figure 20:
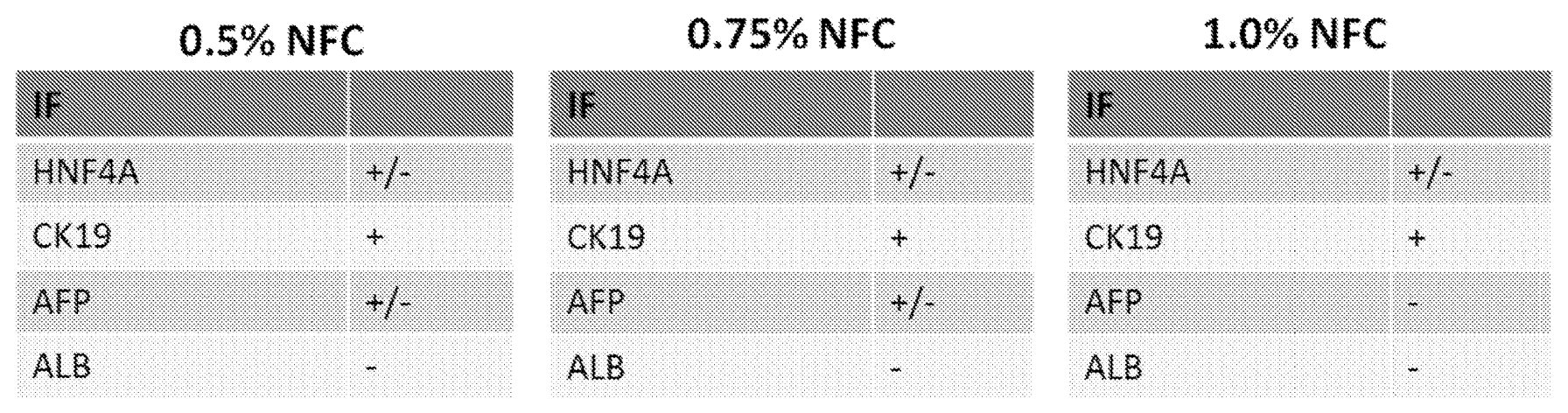

High content screening microscope images of spheroids stained with critical hepatic markers reveal whether the cells have differentiated into hepatic progenitor stage. FIG. 19 shows expression of (A) hepatic progenitor markers HNF4A and CK19 and also (B) early hepatocyte marker AFP and hepatocyte marker albumin (ALB) in spheroids differentiated three-dimensionally from pluripotent stage to hepatic progenitor (HP) stage. HP induction was performed in 0.5%, 0.75% or 1.0% NFC hydrogel for 5 days. The scale bars are 100 µm. Staining of hepatic progenitor markers HNF4A and CK19 showed only little or lack of expressions in all spheroids (FIG. 19 A). Similar expression was seen for early hepatocyte marker AFP in cells grown in 0.5% or 0.75% NFC hydrogel (FIG. 19 B). Albumin and AFP in spheroids from 1.0% hydrogel were negative. FIG. 20 shows a summary of protein expressions in differentiated spheroids from pluripotent until hepatic progenitor (HP) stage studied by immunofluorescence (IF). HP differentiation performed in 0.5%, 0.75% or 1.0% NFC hydrogel for 5 days. The amount of expression is scaled from no expression (−) to high expression (+++). From the summary tables it is easy to conclude that the expression of critical markers was very low in spheroids from all NFC concentrations.

Protein Expression Inside the Spheroids

Figure 21:
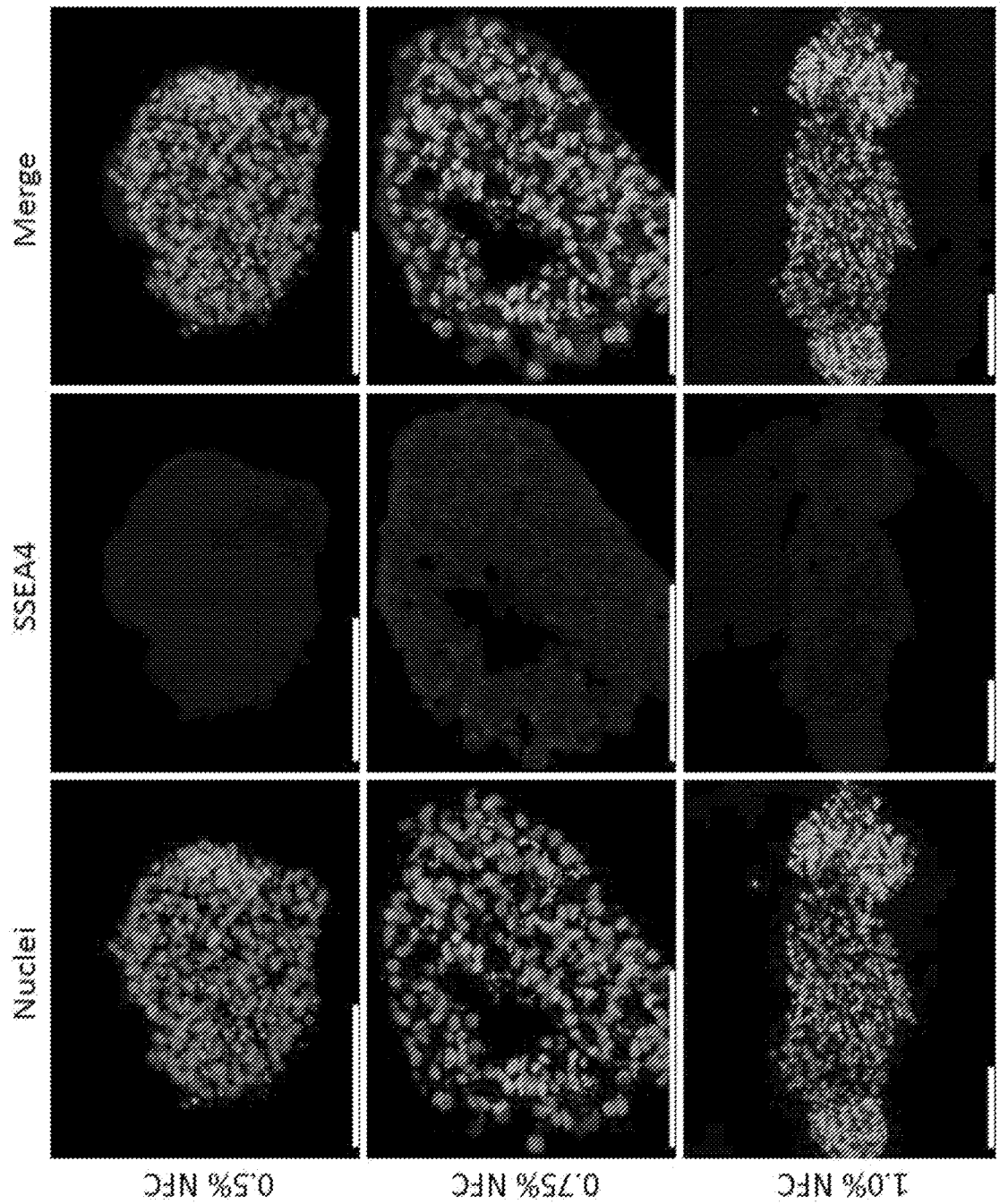
FIG. 21. Expression of pluripotency marker SSEA4 in cells inside spheroids differentiated three-dimensionally from pluripotent to hepatic progenitor (HP) stage.
Figure 22:
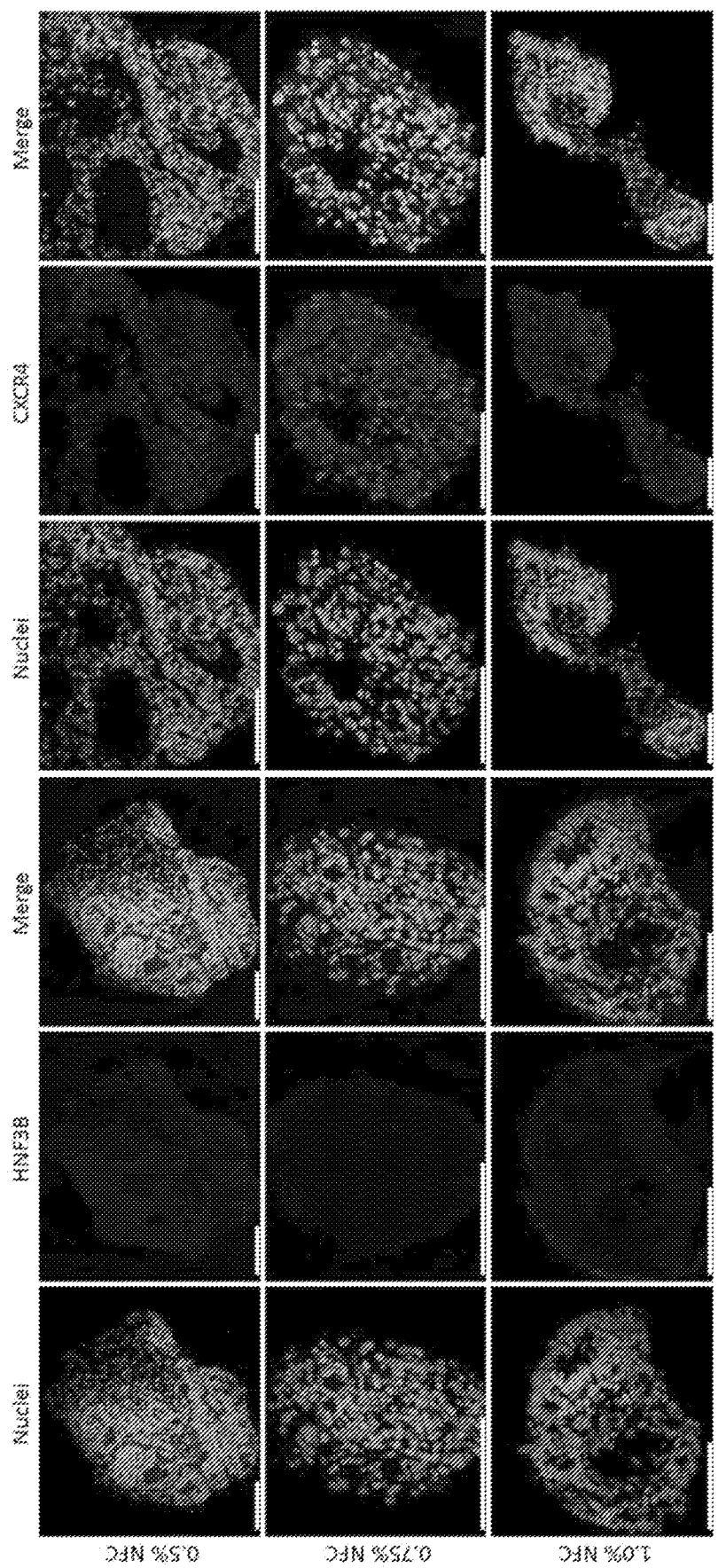
FIG. 22. Expression of definitive endoderm markers HNF3B and CXCR4 in cells inside spheroids differentiated 3D from pluripotent to hepatic progenitor (HP) stage.

Differentiation stage inside the spheroids was revealed by immunohistochemistry on a high content screening microscope. FIG. 21 shows expression of pluripotency marker SSEA4 in cells inside spheroids differentiated three-dimensionally from pluripotent to hepatic progenitor (HP) stage. HP differentiation performed in 0.5%, 0.75% or 1.0% NFC hydrogel for 5 days. The scale bars are 100 m. Pluripotency marker SSEA4 showed some positivity in cells differentiated in 0.75% NFC hydrogel, cells in other concentrations were negative. FIG. 22 shows expression of definitive endoderm markers HNF3B and CXCR4 in cells inside spheroids differentiated three-dimensionally from pluripotent to hepatic progenitor (HP) stage. HP differentiation performed in 0.5%, 0.75% or 1.0% NFC hydrogel for 5 days. The scale bars are 100 µm. DE marker HNF3B was negative in cells from all culturing conditions, and CXCR4 expression was positive especially with 0.75% NFC hydrogel.

Figure 23:
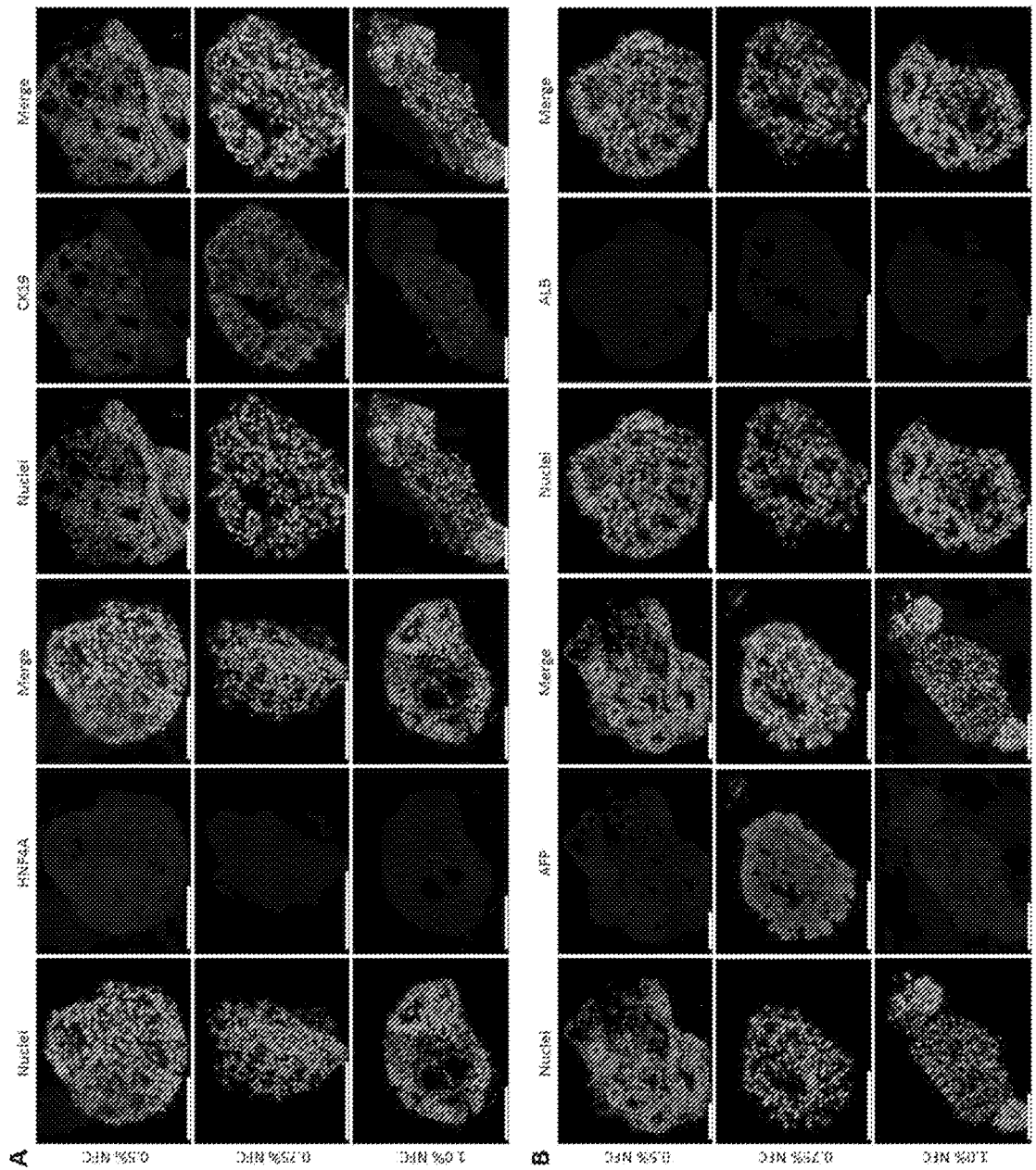
FIG. 23. Expression of (A) hepatic progenitor markers HNF4A and CK19 and also (B) early hepatocyte marker AFP and hepatocyte marker albumin (ALB) in cells inside spheroids differentiated 3D from pluripotent to hepatic progenitor (HP) stage.

FIG. 23 shows expression of (A) hepatic progenitor markers HNF4A and CK19 and also (B) early hepatocyte marker AFP and hepatocyte marker albumin (ALB) in cells inside spheroids differentiated three-dimensionally from pluripotent to hepatic progenitor (HP) stage. HP differentiation performed in 0.5%, 0.75% or 1.0% NFC hydrogel for 5 days. The scale bars are 100 m. Cells inside the spheroids showed no expression for HP marker HNF4A. In contrast, CK19 was highly positive in cells from 0.75% hydrogel and partially positive with spheroids from 0.5% and 1.0% NFC hydrogel (FIG. 23 A). Positive parts of these spheroids were from areas with lower cell density. Cells differentiated in 0.75% NFC hydrogel presented very high expression of early hepatocyte marker AFP, and also cells from 1.0% hydrogel showed weak positivity (FIG. 23 B). There was no AFP marker expression in cells differentiated in 0.5% NFC hydrogel nor albumin expression in any spheroids.

FIG. 24 shows a summary of the protein expressions in differentiated cells inside spheroids studied by immunohistochemistry (IHC). Spheroids were differentiated from pluripotent stem cell stage to definitive endoderm spheroids in 0.5% NFC hydrogel, and then 5 days from definitive endoderm to hepatic progenitor (HP) stage in 0.5%, 0.75% or 1.0% NFC hydrogels. The amount of expression is scaled from no expression (−) until high expression (+++). are shown in FIG. 24. Based on these results obtained from immunohistochemistry experiments for spheroids after HP differentiation, HP induction in 0.75% NFC hydrogel seems to be the best condition from the three chosen options.

Example 4

Extended Cell Viability and Repeated Dose Toxicity Experiments

Primary hepatocytes lose their metabolic competence and viability after 1-2 weeks in 2D culture. GrowDex® as a 3D matrix was evaluated for extended cell viability and repeated dose toxicity with cryopreserved primary hepatocytes.

Cells on 3D were plated on the top GrowDex® hydrogel (1% w/v) using Hepatocyte plating medium, CP medium (Bioreclamation IVT), including additives Torpedo antibiotic mix (Bioreclamation IVT) using 96-well Ultra Low Attachment Microplate (#3474, Corning). For comparison cells on 2D were plated using 96-well Flat Bottom Microplate (#655180, Greiner Bio-one). The GrowDex® hydrogel (UPM-Kymmene Corporation, Helsinki, Finland, lot 11649, exp date 1 Dec. 2015) was 1.65% (w/v) and further diluted to 1% (w/v) with hepatocyte cell culture medium (CP medium from Bioreclamation IVT). Water was prepared with a Direct-Q3 (Millipore Oy, Espoo, Finland) purification system and UP grade (ultra pure, 18.2 MW). The number of cells/well was 2×104 or 6×104/96-well for 3D/2D and the incubation volume was 100 µl of GrowDex® and 100 µl of cells.

Fresh medium was change every second or third day with CP medium (Bioreclamation IVT), including additives Torpedo antibiotic mix (Bioreclamation IVT) for viability assay. For repeated toxicity assay hepatocyte incubation medium, HI medium (Bioreclamation IVT) was used with Torpedo antibiotic mix, medium was replaced with fresh compound medium 3 days after first dosing. During medium changes GrowDex® hydrogel layer remained unaffected and based on monitoring by microscope cells formed clear aggregates on the matrix.

The duration of the cell viability assay test was in total 28 days. Medium samples were taken every other or third day on the 28th day after initiating the cell viability study, all medium samples collected during the study were pooled as follows: from days 1-7, 8-14, 15-21, 22-28. All medium was stored in −20° C. until the day of the assay.

The duration of the repeated toxicity assay test was in total 12 days. Primary hepatocytes were exposed to four selected compounds two times (on days 6 and 9). The compounds tested were propranolol (negative control); diclofenac (positive control); ciprofloxacin; and imipramine. Ciprofloxacin and imipramine are known to cause drug induced liver injury in clinic, but their toxicity is not identified by conventional 2D or sandwich 3D culture models. The first 6 days was used for 3D culture establishment after which a first dose was added at day 6 and a second dose at day 9 from plating, resulting in 6 day repeated toxicity assay, after which the study was terminated.

The compounds for the toxicity testing were chosen according to Khetani et al, table 1, with known susceptibility to drug-induced liver injury (DILI). Diclofenac displays clinical DILI and also shows toxicity in all tested 3D models (by Khetani et al. 2013). Propranolol does not display clinical DILI and it is not detected in the 3D liver models, i.e. it was used as negative control compound. Ciprofloxacin and imipramine both display clinical DILI, but toxicity is not detected in all 3D models tested (by Khetani et al. 2013). The concentrations of the compounds used were chosen based on their Cmax values, as well as solubility properties and these are presented in Table 7.

TABLE 7

The compounds chosen for toxicity study and their concentrations used

| Compound | $C_{max}$ value µM (by Khetani et al. 2013) | Used final concentration in incubation |
|---|---|---|
| Ciprofloxacin | 11.5 | 1x, 5x, 30x $C_{max}$, corresponds to 10, 50 and 300 µM |
| Imipramine | 0.087 | 1x, 35x, 115x $C_{max}$ corresponds to 0.1, 3 and 10 µM |
| Diclofenac | 8 | 0.6x, 20x, 60x $C_{max}$ corresponds to 5, 150 and 500 µM |
| Propranolol | 0.2 | 1x, 30x, 100x $C_{max}$ corresponds to 0.2, 6 and 20 µM |

Viability was analysed by measuring LDH (both for the viability and toxicity studies) using CytoTox-ONE® Homogenous Membrane Integrity Assay (Promega) from the cell culture medium sample (50 µl), followed by fluorescence measurement; 560 nm excitation, 600 nm emission.

For the toxicity test two different sample sets were collected for cell viability determination; medium samples after first exposure (LDH) and medium samples after second exposure (LDH).

Albumin and urea secretion were used as biomarkers for liver-like functions in the toxicity study. For the determination of albumin levels Albumin Human ELISA Kit (Abcam® ab108788) from the cell culture medium sample (50 µl), followed by absorbance measurement; 450 nm (wavelength correction at 570 nm) were used. Determination of urea was conducted using Urea Assay Kit (Abcam® ab83362) from the cell culture medium sample (10 µl), followed by absorbance measurement; 570 nm.

Results

For the long-term 3D culture of primary hepatocytes in GrowDex® viability was analysed by measuring LDH. The cells remained viable in GrowDex throughout the experiment (28 days), while 2D culture was not continued after 14 days. The results are presented in Table 8 as RFU LDH leakage. LDH leakage indicates cytotoxicity, high values suggests cell death.

TABLE 8

Cytotoxicity in the cell viability study using GrowDex ®
(relative mean and SD, n = 3).

| Sample | Cytotoxicity (LDH leakage) | |
|---|---|---|
| | average (RFU) | SD (RFU) |
| Medium | 11315 | 220 |
| 20 000 cells/3D GrowDex ® 1-7 days | 14750 | 911 |

TABLE 8-continued

Cytotoxicity in the cell viability study using GrowDex ®
(relative mean and SD, n = 3).

| Sample | Cytotoxicity (LDH leakage) | |
|---|---|---|
| | average (RFU) | SD (RFU) |
| 20 000 cells/3D GrowDex ® 8-14 days | 10325 | 403 |
| 20 000 cells/3D GrowDex ® 15-21 days | 11419 | 414 |
| 20 000 cells/3D GrowDex ® 22-28 days | 10574 | 86 |
| 60 000 cells/3D GrowDex ® 1-7 days | 33394 | 2129 |
| 60 000 cells/3D GrowDex ® 8-14 days | 9649 | 1788 |
| 60 000 cells/3D GrowDex ® 15-21 days | 13669 | 486 |
| 60 000 cells/3D GrowDex ® 22-28 days | 12240 | 599 |
| 20 000 cells/2D 1-7 days | 16798 | 597 |
| 20 000 cells/2D 8-14 days | 10928 | 797 |
| 60 000 cells/2D 1-7 days | 42668 | 3026 |
| 60 000 cells/2D 8-14 days | 14471 | 1411 |

Figure 25:
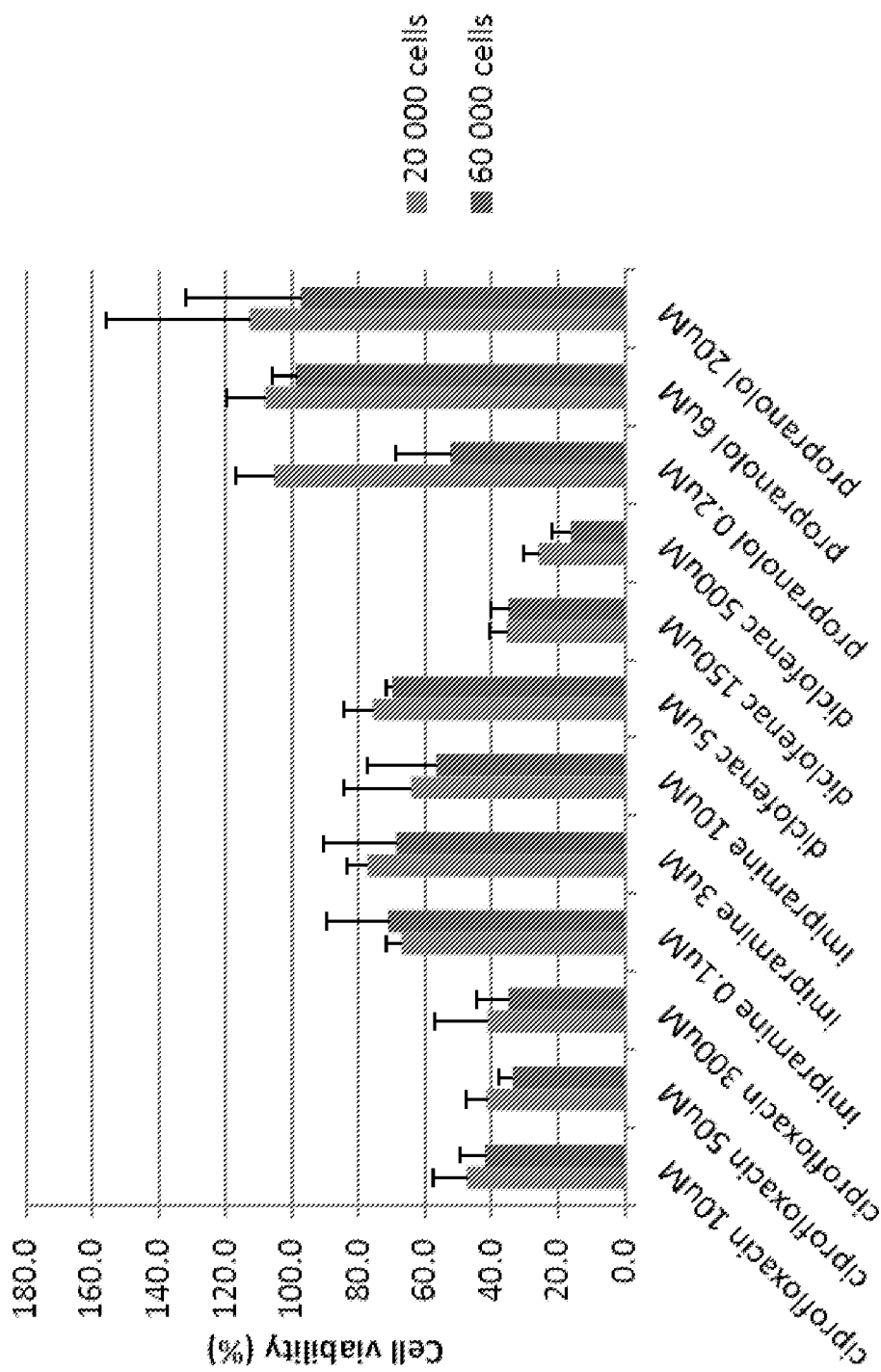
FIG. 25. Primary hepatocyte viability (LDH) after drug exposure.

For the repeated dose toxicity experiments a clear difference in cell viability (LDH) between propranolol and diclofenac was observed with both cell densities after first exposure (FIG. 25). A decrease in cell viability was observed also for both ciprofloxacin and imipramine. The observed cytotoxicity and cell viability are presented in Table 9. Lower cell viability than 100% suggests cytotoxicity.

TABLE 9

Relative cell viability in repeated dose toxicity study
(relative mean and SD, n = 3).
Results are normalized against 3D vehicle control set as 100% viability
(DMSO GrowDex ®).

| Sample | 1$^{st}$ exposure (LDH) | | 2$^{nd}$ exposure (LDH) | | 2$^{nd}$ exposure (ATP) | |
|---|---|---|---|---|---|---|
| | Average (%) | SD | Average (%) | SD | Average (%) | SD |
| 20000 cells | | | | | | |
| DMSO 2D | 59.6 | 8.6 | 119.7 | 13.3 | 434.1 | 21.4 |
| DMSO GrowDex ® | 100.0 | 14.1 | 100.0 | 14.1 | 100.0 | 17.6 |
| ciprofloxacin 10 uM | 47.5 | 10.3 | 73.3 | 8.8 | 45.8 | 5.0 |
| ciprofloxacin 50 uM | 41.4 | 6.3 | 72.6 | 1.9 | 75.5 | 2.6 |
| ciprofloxacin 300 uM | 41.2 | 16.1 | 71.9 | 16.3 | 91.5 | 28.0 |
| imipramine 0.1 uM | 67.2 | 4.6 | 76.3 | 9.1 | 87.8 | 10.0 |
| imipramine 3 uM | 77.5 | 6.1 | 80.8 | 7.8 | 109.6 | 16.0 |
| imipramine 10 uM | 64.3 | 19.9 | 73.3 | 10.8 | 93.3 | 5.6 |
| diclofenac 5 uM | 75.7 | 8.7 | 76.4 | 16.8 | 86.2 | 29.4 |
| diclofenac 150 uM | 35.5 | 5.0 | 59.4 | 3.0 | 101.4 | 20.7 |
| diclofenac 500 uM | 25.8 | 4.4 | 60.1 | 6.6 | 54.9 | 21.1 |
| propranolol 0.2 uM | 105.3 | 11.7 | 93.9 | 14.2 | 98.8 | 20.4 |
| propranolol 6 uM | 108.1 | 11.5 | 93.0 | 13.4 | 112.2 | 15.1 |
| propranolol 20 uM | 112.8 | 42.8 | 79.1 | 27.3 | 32.7 | 20.3 |
| 60000 cells | | | | | | |
| DMSO 2D | 47.0 | 12.2 | 106.1 | 4.6 | 165.8 | 4.8 |
| DMSO GrowDex ® | 100.0 | 1.0 | 100.0 | 16.9 | 100.0 | 21.5 |
| ciprofloxacin 10 uM | 42.0 | 7.8 | 70.9 | 11.4 | 49.7 | 8.2 |
| ciprofloxacin 50 uM | 33.7 | 4.0 | 75.3 | 5.9 | 74.1 | 15.2 |
| ciprofloxacin 300 uM | 34.9 | 9.7 | 69.6 | 9.5 | 71.5 | 17.6 |
| imipramine 0.1 uM | 71.1 | 18.2 | 83.8 | 13.7 | 85.6 | 12.6 |
| imipramine 3 uM | 68.8 | 21.5 | 87.5 | 21.0 | 87.1 | 8.9 |
| imipramine 10 uM | 56.7 | 20.6 | 84.3 | 5.0 | 96.7 | 22.7 |
| diclofenac 5 uM | 69.9 | 2.1 | 80.9 | 12.2 | 72.2 | 12.5 |
| diclofenac 150 uM | 34.9 | 5.2 | 62.8 | 11.5 | 83.6 | 13.4 |
| diclofenac 500 uM | 16.3 | 5.4 | 55.0 | 14.7 | 42.4 | 18.7 |

TABLE 9-continued

Relative cell viability in repeated dose toxicity study
(relative mean and SD, n = 3).
Results are normalized against 3D vehicle control set as 100% viability
(DMSO GrowDex ®).

| Sample | 1$^{st}$ exposure (LDH) Average (%) | SD | 2$^{nd}$ exposure (LDH) Average (%) | SD | 2$^{nd}$ exposure (ATP) Average (%) | SD |
|---|---|---|---|---|---|---|
| propranolol 0.2 uM | 52.4 | 16.6 | 93.0 | 8.8 | 94.6 | 15.3 |
| propranolol 6 uM | 99.0 | 6.9 | 103.3 | 12.9 | 127.0 | 16.4 |
| propranolol 20 uM | 97.4 | 34.6 | 82.9 | 25.4 | 40.4 | 28.8 |

The albumin secretion was supporting the cell viability results. The cells exposed to propranolol resulted in the highest albumin levels and albumin secretion was significantly diminished in all other samples. The results are shown in Table 10. High secretion suggests liver-like function of the sample and lowered secretion suggests cytotoxicity and/or non-liver like properties. The same trend was observed for urea secretion, but the differences between the non-toxic and toxic samples were lower. The results are shown in Table 11. High production suggests liver-like function of the sample and lowered secretion suggests cytotoxicity and/or non-liver like properties.

TABLE 10

Albumin secretion in repeated dose toxicity study
(relative mean and SD, n = 3). Results are
presented as ng/ml human albumin.

| Sample | 20 000 cells Average (ng/ml) | SD | 60 000 cells Average (ng/ml) | SD |
|---|---|---|---|---|
| DMSO 2D | 458.7 | 355.2 | 1864.1 | 227.1 |
| DMSO GrowDex ® | 71.5 | 15.2 | 557.9 | 435.5 |
| ciprofloxacin 50 uM | 47.2 | 11.6 | 147.7 | 49.2 |
| ciprofloxacin 300 uM | 50.8 | 13.7 | 134.6 | 7.0 |
| imipramine 0.1 uM | 61.0 | 13.5 | 183.1 | 27.1 |
| imipramine 3 uM | 56.5 | 8.8 | 113.3 | 11.2 |
| imipramine 10 uM | 72.6 | 13.5 | 197.2 | 51.8 |
| diclofenac 5 uM | 74.9 | 33.3 | 260.1 | 97.4 |
| diclofenac 150 uM | 53.6 | 19.7 | 250.9 | 231.2 |
| diclofenac 500 uM | 41.2 | 3.5 | 129.7 | 74.1 |
| propranolol 0.2 uM | 84.9 | 31.9 | 380.0 | 84.3 |
| propranolol 6 uM | 93.2 | 47.0 | 713.5 | 2.7 |
| propranolol 20 uM | 71.3 | 30.6 | 499.3 | 194.9 |

TABLE 11

Urea secretion in repeated dose toxicity study (relative mean and
SD, n = 3). Results are presented as μM urea production.

| Sample | 20 000 cells Average (μM) | SD | 60 000 cells Average (μM) | SD |
|---|---|---|---|---|
| DMSO 2D | ND | ND | ND | ND |
| DMSO GrowDex ® | 114.0 | 48.4 | 110.5 | 21.9 |
| ciprofloxacin 10 uM | 378.5 | 105.0 | 244.5 | 101.1 |
| ciprofloxacin 50 uM | 97.5 | 122.0 | 87.3 | 60.7 |
| ciprofloxacin 300 uM | 82.1 | 4.2 | 78.7 | 65.9 |
| imipramine 0.1 uM | 58.3 | 25.1 | 87.0 | 47.0 |
| imipramine 3 uM | 103.0 | 6.7 | 131.8 | 34.0 |
| imipramine 10 uM | 57.7 | 9.3 | 97.6 | 16.2 |
| diclofenac 5 uM | 67.3 | 38.0 | 64.5 | 55.5 |
| diclofenac 150 uM | 74.9 | 69.2 | 80.8 | 37.4 |
| diclofenac 500 uM | 116.3 | 36.5 | 102.1 | 33.7 |

TABLE 11-continued

Urea secretion in repeated dose toxicity study (relative mean and
SD, n = 3). Results are presented as μM urea production.

| Sample | 20 000 cells Average (μM) | SD | 60 000 cells Average (μM) | SD |
|---|---|---|---|---|
| propranolol 0.2 uM | 58.9 | 35.2 | 78.3 | 14.0 |
| propranolol 6 uM | 76.7 | 28.7 | 173.2 | 42.3 |
| propranolol 20 uM | 53.3 | 48.0 | 165.1 | 7.1 |

ND = not detected

For the removal of GrowDex® hydrogel cellulase enzyme treatment is used. The grown 3D cell structures are retained. Cell culture medium on top of GrowDex is replaced with fresh medium containing cellulase enzyme, and incubated at 37 C until the hydrogel is degraded. 300 mg/g cellulase enzyme/cellulose with an incubation time of 24 h is used to fully degrade the GrowDex® hydrogel containing the cultured cells. A further cell viability analysis with ATP using cell lysate is made after the enzyme breakdown of Grow-Dex®.

The present invention has been described herein with reference to specific embodiments. It is, however clear to those skilled in the art that the invention may be varied within the scope of the claims.

REFERENCES

Khetani S & Bhatia S (2008) Microscale culture of human liver cells for drug development. Nature Biotechnology 26(1):120-126.

The invention claimed is:
1. A method for culturing and chemical testing of in vivo like cells, the method comprising:
a) culturing cells on or in a first plant-derived nanofibrillar cellulose (NFC) hydrogel to obtain in vivo like cells;
b) exposing the in vivo like cells to a test chemical within a second plant-derived NFC hydrogel after removing at least some of the first NFC hydrogel, the first and second NFC hydrogel having a number average diameter of about 1-20 nm, the second hydrogel having a different NFC concentration than the first NFC hydrogel;
c) incubating the exposed in vivo like cells; and
d) detecting, during or after the incubation, a qualitative and/or quantitative impact of the test chemical on the in vivo like cells, by at least one detection technique, the at least one detection technique selected from the group consisting of chromatography, spectroscopy, microscopy, photometry, laser or flow-cytometry, high-throughput screening, or any combination thereof.

2. The method according to claim 1, wherein the removing the at least some of the first plant-derived NFC hydrogel comprises physical removing, mechanical removing, chemical removing, or any combination thereof.

3. The method according to claim 1, further comprising removing the second plant-derived NFC hydrogel between b) and d).

4. The method of claim 1, further comprising:
e) removing the second NFC hydrogel to separate the second NFC hydrogel from the in vivo like cells at any stage after b) and before the at least one detection technique according to d).

5. The method of claim 4, wherein, during e), the second plant-derived NFC hydrogel is treated enzymatically with a cellulase for a time sufficient to at least partly release the cells.

6. The method according to claim 5, wherein the cellulase is a cellulolytic enzyme mixture.

7. The method of claim 6, wherein the cellulase comprises hemicellulases, a commercial cellulase, a partially purified cellulase, or a purified cellulase.

8. The method according to claim 1, wherein the second hydrogel has different properties than the first NFC hydrogel, the properties selected from the group consisting of one or more of size distribution, length, diameter, chemical composition, or rheological properties.

9. The method according to claim 1, wherein the second NFC hydrogel has different properties than the first NFC hydrogel, the different properties being selected from the group consisting of stiffness of NFC hydrogel, shear-zero viscosity of NFC hydrogel, charge of NFC, and transparency of NFC hydrogel.

10. The method according to claim 1, wherein said chemical testing comprises toxicity testing; safety testing; drug candidate testing; drug screening; or pro-drug candidate testing.

11. The method of claim 1, wherein the chemical testing is for genotoxicity, carcinogenicity, neurotoxicity, mitochondrial toxicity, cardiotoxicity, hepatotoxicity, hematopoietic toxicity, nephrotoxicity, safety testing, causing reproductive toxicity, skin irritation, eye irritation, or any combination thereof.

12. The method according claim 1, wherein said test chemical is selected from the group consisting of drugs, drug candidates, pro-drugs, pro-drug candidates, nanoparticles, cell regulatory agents, food or food additives, household products, industrial chemicals, packing materials, air freshener, plant growth regulatory agents, environmental toxins, pesticides, personal care products, or their chemical ingredients.

13. The method according to claim 1, wherein said in vivo like cells are stem cells, primary cells, secondary cells, or any combinations thereof.

14. The method according to claim 1, wherein the first NFC hydrogel is provided onto a support before cells for culturing are seeded onto or into the first NFC hydrogel or after cells for culturing are seeded into the first NFC hydrogel.

15. The method according to claim 1, wherein the detection of the impact of the test chemical on the in vivo like cells further comprises transplantation of the exposed in vivo like cells into test animals.

16. The method of claim 1, wherein, during the incubating, the exposed in vivo like cells absorb, bind to, or otherwise react with the test chemical.

17. The method according to claim 1, wherein said first or second NFC hydrogel includes from 0.05 to 10 wt % of nanofibrillar cellulose.

18. The method according to claim 1, wherein said first or second NFC hydrogel comprises native nanofibrillar cellulose.

19. The method according to claim 1, wherein said first or second NFC hydrogel comprises nanofibrillar cellulose including cellulose I.

20. The method according to claim 1, wherein said first or second NFC hydrogel has a stiffness of at least 4 Pa.

21. The method of claim 1, wherein at least one of the first or second NFC hydrogel is anionic.

22. The method of claim 1, wherein at least one of the first or second NFC hydrogels has a turbidity of about 80 NTU or less.

23. The method according to claim 1, wherein the detection technique is chromatography, the chromatography selected from the group consisting of Gas Chromatography (GC), High Performance Liquid Chromatography (HPLC), affinity chromatography, displacement chromatography, ion-exchange chromatography, size exclusion chromatography, gel-filtration chromatography, fast protein liquid chromatography, paper chromatography, thin-layer chromatography, electrochromatography, or any combination thereof.

24. The method of claim 23, wherein the electrochromatography is selected from the group consisting of gel-electrophoresis, 2D gel-electrophoresis, isoelectric focusing, or any combination thereof.

25. The method of claim 1, wherein the detection technique is spectroscopy, the spectroscopy selected from the group consisting of nuclear magnetic resonance (NMR) spectroscopy, Raman spectroscopy, Infrared spectroscopy (IR), Ultraviolet spectroscopy (UV), visible light spectroscopy, fluorescence spectroscopy, mass spectrometry (MS), or any combination thereof.

26. The method of claim 1, wherein the detection technique is microscopy, the microscopy selected from the group consisting of optical microscopy, electron microscopy, scanning-probe microscopy, or any combination thereof.

27. The method of claim 26, wherein the optical microscopy is selected from the group consisting of phase contrast microscopy, reverse phase contrast microscopy, confocal microscopy, fluorescence microscopy, or any combination thereof.

28. The method of claim 26, wherein the electron microscopy is selected from the group consisting of Transmission Electron Microscopy (TEM), Scanning Electron Microscopy (SEM), or any combination thereof.

29. The method of claim 26, wherein the scanning probe microscopy is Atomic Force Microscopy (AFM).

* * * * *